US009555097B2

(12) United States Patent
Rybicki et al.

(10) Patent No.: US 9,555,097 B2
(45) Date of Patent: Jan. 31, 2017

(54) RECOMBINANT PROTEIN BODIES AS IMMUNOGEN-SPECIFIC ADJUVANTS

(75) Inventors: Edward Peter Rybicki, Pinelands (ZA); Ann Elizabeth Meyers, Plumstead (ZA); François Devesa, Launaguet (FR); Pablo Marzábal Luna, Barcelona (ES); Inga Isabel Hitzeroth, Cape Town (ZA); Peter Öhlschläger, Constance (DE)

(73) Assignee: ERA BIOTECH, S.A., Cerdanyola del Vallès, Barcelona (ES)

( * ) Notice: Subject to any disclaimer, the term of this patent is extended or adjusted under 35 U.S.C. 154(b) by 90 days.

(21) Appl. No.: 13/123,510

(22) PCT Filed: Oct. 9, 2009

(86) PCT No.: PCT/EP2009/063223
§ 371 (c)(1),
(2), (4) Date: Jul. 5, 2011

(87) PCT Pub. No.: WO2010/040847
PCT Pub. Date: Apr. 15, 2010

(65) Prior Publication Data
US 2011/0262478 A1 Oct. 27, 2011
US 2016/0243213 A9 Aug. 25, 2016

Related U.S. Application Data

(63) Continuation-in-part of application No. 11/709,527, filed on Feb. 22, 2007, now Pat. No. 8,163,880.

(60) Provisional application No. 60/776,391, filed on Feb. 23, 2006, provisional application No. 61/104,403, filed on Oct. 10, 2008.

(51) Int. Cl.
| | |
|---|---|
| *A61K 39/21* | (2006.01) |
| *C07K 14/005* | (2006.01) |
| *C07K 14/415* | (2006.01) |
| *C07K 14/425* | (2006.01) |
| *C12N 7/00* | (2006.01) |
| *C12N 15/62* | (2006.01) |
| *C12N 15/82* | (2006.01) |
| *A61K 39/12* | (2006.01) |
| *A61K 39/385* | (2006.01) |
| *A61K 39/00* | (2006.01) |

(52) U.S. Cl.
CPC ........... *A61K 39/21* (2013.01); *A61K 39/0011* (2013.01); *A61K 39/12* (2013.01); *A61K 39/385* (2013.01); *C07K 14/005* (2013.01); *C07K 14/415* (2013.01); *C07K 14/425* (2013.01); *C12N 7/00* (2013.01); *C12N 15/625* (2013.01); *C12N 15/8216* (2013.01); *C12N 15/8218* (2013.01); *C12N 15/8257* (2013.01); *C12N 15/8258* (2013.01); *A61K 2039/5258* (2013.01); *A61K 2039/53* (2013.01); *A61K 2039/54* (2013.01); *A61K 2039/55516* (2013.01); *A61K 2039/572* (2013.01); *A61K 2039/575* (2013.01); *A61K 2039/585* (2013.01); *A61K 2039/6031* (2013.01); *C07K 2319/04* (2013.01); *C12N 2710/20022* (2013.01); *C12N 2710/20034* (2013.01); *C12N 2710/20071* (2013.01); *C12N 2740/16022* (2013.01); *C12N 2740/16034* (2013.01); *C12N 2740/16122* (2013.01); *C12N 2740/16222* (2013.01); *C12N 2740/16234* (2013.01); *C12N 2740/16322* (2013.01)

(58) Field of Classification Search
None
See application file for complete search history.

(56) References Cited

U.S. PATENT DOCUMENTS

| | | | |
|---|---|---|---|
| 4,215,040 A | 7/1980 | Hager | |
| 4,882,145 A | 11/1989 | Thornton et al. | |
| 4,886,782 A | 12/1989 | Good et al. | |
| 5,215,912 A | 6/1993 | Hoffman | |
| 5,478,726 A | 12/1995 | Shinnick et al. | |
| 5,589,616 A | 12/1996 | Hoffman | |
| 5,639,854 A | 6/1997 | Sia et al. | |

(Continued)

FOREIGN PATENT DOCUMENTS

| | | |
|---|---|---|
| EP | 0 399 001 B1 | 7/1994 |
| EP | 2 418 284 A1 | 2/2012 |

(Continued)

OTHER PUBLICATIONS

Ackerman, A.L. and Cresswell, P., "Cellular mechanisms governing cross-presentation of exogenous antigens," *Nature Immunology* 5(7):678-684, Nature America Inc., United States (2004).
Alexander, J., et al., "Development of High Potency Universal DR-Restricted Helper Epitopes by Modification of High Affinity DR-Blocking Peptides," *Immunity* 1:751-761, Cell Press, United States (1994).
Altschuler, Y., et al., "The N- and C-Terminal Regions Regulate the Transport of Wheat γ-Gliadin through the Endoplasmic Reticulum in Xenopus Oocytes," *The Plant Cell* 5:443-450, American Society of Plant Physiologists, United States (1993).

(Continued)

*Primary Examiner* — Yunsoo Kim
(74) *Attorney, Agent, or Firm* — Tristan A. Fuierer; Moore & Van Allen, PLLC

(57) ABSTRACT

An immunogen-specific is adjuvant for a vaccine or inoculum is disclosed. The adjuvant is comprised of particulate recombinant protein body-like assemblies (RPBLAs) that contain a recombinant fusion protein that contains two portions peptide-linked together. A first portion is a protein body-inducing sequence (PBIS) and a second portion is a T-cell stimulating immunogenic polypeptide whose sequence is that of a pathogenic polypeptide sequence present in or induced by a vaccine or inoculum. The adjuvant, when used as an inoculum in a host animal without a prior priming vaccination or inoculation, does not induce production of antibodies or T cell activation to the pathogenic sequence.

**11 Cla

(56) References Cited

U.S. PATENT DOCUMENTS

| | | |
|---|---|---|
| 5,948,682 A | 9/1999 | Moloney |
| 5,990,384 A | 11/1999 | Bagga et al. |
| 6,642,437 B1 | 11/2003 | Lemaux et al. |
| 6,942,866 B2 | 9/2005 | Birkett |
| 7,329,498 B2 | 2/2008 | Harding et al. |
| 7,575,898 B2 | 8/2009 | Ludevid Mugica et al. |
| 7,732,569 B2 | 6/2010 | Decarolis et al. |
| 8,163,880 B2 | 4/2012 | Heifetz et al. |
| 8,337,817 B2 | 12/2012 | Nagata et al. |
| 2002/0061309 A1 | 5/2002 | Garger et al. |
| 2004/0005660 A1 | 1/2004 | Ludevid Mugica et al. |
| 2005/0244924 A1 | 11/2005 | Wagner et al. |
| 2006/0121573 A1 | 6/2006 | Torrent et al. |
| 2006/0123509 A1 | 6/2006 | Torrent et al. |
| 2006/0182763 A1 | 8/2006 | Kim et al. |
| 2007/0243198 A1 | 10/2007 | Heifetz et al. |
| 2010/0083403 A1 | 4/2010 | Ludevid Mugica et al. |
| 2011/0305718 A1 | 12/2011 | Ludevid Mgica et al. |

FOREIGN PATENT DOCUMENTS

| | | | |
|---|---|---|---|
| WO | WO 96/21029 A1 | | 7/1996 |
| WO | WO 00/40738 A1 | | 7/2000 |
| WO | WO 02/086077 A2 | | 10/2002 |
| WO | WO 03/072731 A2 | | 9/2003 |
| WO | WO 2004/003207 A1 | | 1/2004 |
| WO | WO 2005/113775 A1 | | 12/2005 |
| WO | WO 2006/056483 A1 | | 6/2006 |
| WO | WO 2006/056484 A1 | | 6/2006 |
| WO | WO 2007/096192 | * | 8/2007 |
| WO | WO 2007/096192 A2 | | 8/2007 |
| WO | WO 2011/147995 A1 | | 12/2011 |

OTHER PUBLICATIONS

Arcalis, E., et al., "Unexpected Deposition Patterns of Recombinant Proteins in Post-Endoplasmic Reticulum Compartments of Wheat Endosperm," *Plant Physiology* 136:3457-3466, American Society of Plant Biologists, United States (2004).

Bagga, S., et al., "Accumulation of 15-Kilodalton Zein in Novel Protein Bodies in Transgenic Tobacco," *Plant Physiol.* 107:13-23, American Society of Plant Physiologists, United States (1995).

Bagga, S., et al., "Coexpression of the Maize δ-Zein and β-Zein Genes Results in Stable Accumulation of δ-Zein in Endoplasmic Reticulum-Derived Protein Bodies Formed by β-Zein," *The Plant Cell* 9:1683-1696, American Society of Plant Physiologists, United States (1997).

Bicudo, T.C., et al., "γ-Zein Secondary Structure in Solution by Circular Dichroism." *Biopolymers* 89(3):175-178, Wiley Periodicals, Inc., United States (2007).

Blander, J.M. and Medzhitov, R., "On regulation of phagosome maturation and antigen presentation," *Nature Immunology* 7(10):1029-1035, Nature America Inc., United States (2006).

Bochicchio, B. and Tamburro, A.M., "Polyproline II Structure in Proteins: Identification by Chiroptical Spectroscopies, Stability, and Functions," *Chirality* 14:782-792, Wiley-Liss, Inc., United States (2002).

Bockenstedt, L.K., et al., "Identification of a *Borrelia burgdorferi* OspA T Cell Epitope That Promotes Anti-OspA IgG in Mice," *The Journal of Immunology* 15(12):5496-5502, The American Association of Immunologists, United States (1996).

Boes, M., et al., "T-cell engagement of dendritic cells rapidly rearranges MHC class II transport," *Nature* 418:983-988, Nature Publishing Group, England (2002).

Bosch, F.X., et al., "Prevalence of Human Papollomavirus in Cervical Cancer: a Worldwide Perspective," *Journal of the National Cancer Institute* 87(11):796-802, Oxford University Press, England (1995).

Boyer, J.D., et al., "DNA Vaccination as Anti-Human Immunodeficiency Virus Immunotherapy in Infected Chimpanzees," *The Journal of Infectious Diseases* 176:1501-1509, The University of Chicago, United States (1997).

Brett, S.J., et al., "Human T Cell Recognition of Influenza A Nucleoprotein: Specificity and Genetic Restriction of Immunodominant T Helper Cell Epitopes," *The Journal of Immunology* 147(3):984-991, The American Association of Immunologists, United States (1991).

Brown, L.E., et al., "Conservation of Determinants for Class II-Restricted T Cells within Site E of Influenza Virus Hemagglutinin and Factors Influencing Their Expression," *Journal of Virology* 67(5):2887-2893, American Society for Microbiology, United States (1993).

Brumeanu, T.-D., et al., "Engineering of doubly antigenized immunoglobulins expressing T and B viral epitopes," *Immunotechnology* 2:85-95, Elsevier Science B.V., Netherlands (1996).

Bukrinsky, M.I., et al., "A nuclear localization signal within HIV-1 matrix protein that governs infection of non-dividing cells," *Nature* 365:666-669, Nature Publishing Group, England (1993).

Burgers, W.A., et al., "Construction, Characterization, and Immunogenicity of a Multigene Modified Vaccinia Ankara (MVA) Vaccine Based on HIV Type 1 Subtype C," *AIDS Research and Human Retroviruses* 24(2):195-206, Mary Ann Liebert, Inc. United States (2008).

Calarota, S., et al., "Cellular cytotoxic response induced by DNA vaccination in HIV-1-infected patients," *The Lancet* 351:1320-1325, Lancet Publishing Group, England (1998).

Caldwell, J.W., et al., "Theoretical π-π* Absorption, Circular Dichroic, and Linear Dichroic Spectra of Collagen Triple Helices," *Biopolymers* 23:1891-1904, John Wiley & Sons, Inc., United States (1984).

Calvo-Calle, J.M., et al., "Binding of Malaria T Cell Epitopes to DR and DQ Molecules In Vitro Correlates with Immunogenicity In Vivo: Identification of a Universal T Cell Epitope in the *Plasmodium falciparum* Circumsporozoite Protein," *The Journal of Immunology* 159:1362-1373, The American Association of Immunologists, United States (1997).

Casimiro, D.R., et al., "Vaccine-Induced Immunity in Baboons by Using DNA and Replication-Incompetent Adenovirus Type 5 Vectors Expressing a Human Immunodeficiency Virus Type 1 gag Gene," *Journal of Virology* 77(13):7663-7668, American Society for Microbiology, United States (2003).

Chege, G.K., et al., "HIV-1 subtype C Pr55$^{gag}$ virus-like particle vaccine efficiently boosts baboons primed with a matched DNA vaccine," *Journal of General Virology* 89:2214-2227, SGM, England (2008).

Cherpelis, S., et al., "DNA-immunization with a V2 deleted HIV-1 envelope elicits protective antibodies in macaques," *Immunology Letters* 79:47-55, Elsevier Science B.V, Netherlands (2001).

Coleman, C.E., et al., "The Maize δ-Zein Sequesters α-Zein and Stabilizes Its Accumulation in Protein Bodies of Transgenic Tobacco Endosperm," *The Plant Cell* 8:2335-2345, American Society of Plant Physiologists, United States (1996).

Conrad, U. and Fiedler, U., "Compartment-specific accumulation of recombinant immunoglobulins in plant cells: an essential tool for antibody production and immunomodulation of physiological functions and pathogen activity," *Plant Molecular Biology* 38:101-109, Kluwer Academic Publishers, Netherlands, (1998).

Dalcol, I., et al., "Convergent Synthesis of Repeating Peptides (Val-X-Leu-Pro-Pro-Pro)$_8$ Adopting a Polyproline II Conformation," *J. Org. Chem.* 61(20):6775-6782, American Chemical Society, United States (1996).

Dela Cruz, C.S., et al., "Creating HIV-1 reverse transcriptase cytotoxic T lymphocyte target structures by HLA-A2 heavy chain modifications," *International Immunology* 12(9):1293-1302, The Japanese Society for Immunology, Japan (2000).

Deml, L., et al., "Recombinant Human Immunodeficiency Pr55$^{gag}$ Virus-like Particles Presenting Chimeric Envelope Glycoproteins Induce Cytotoxic T-Cells and Neutralizing Antibodies," *Virology* 235:26-39, Academic Press, United States (1997).

Deml, L., et al., "Virus-like Particles: A Novel Tool for the Induction and Monitoring of Both T-Helper and Cytotoxic T-Lymphocyte Activity," *Methods in Molecular Medicine* 94:133-157, Humana Press Inc., United States (2004).

(56) References Cited

OTHER PUBLICATIONS

Doan, L.X., et al., "Virus-like particles as HIV-1 vaccines," *Rev. Med. Virol.* 15:75-88, John Wiley & Sons, Ltd., United States (2004).

Doan, T., et al., "Peripheral Tolerance to Human Papillomavirus E7 Oncoprotein Occurs by Cross-Tolerization, Is Largely Th-2-independent, and Is Broken by Dendritic Cell Immunization," *Cancer Research* 60:2810-2815, American Association for Cancer Research, United States (2000).

Dorfman, T., et al., "Functional Domains of the Capsid Protein of Human Immunodeficiency Virus Type 1," *Journal of Virology* 68(12):8180-8187, American Society for Microbiology, United States (1994).

Drakakaki, G., et al., "The Intracellular Fate of a Recombinant Protein Is Tissue Dependent," *Plant Physiology* 141:578-586, American Society of Plant Biologists, United States (2006).

Dyson, N., et al., "The Papilloma Virus-16 E7 Oncoprotein Is Able to Bind to The Retinoblastoma Gene Product," *Science* 243:934-937, American Association for the Advancement of Science, United States (1989).

Edmonds, C. and Vousden, K.H., "A Point Mutational Analysis of Human Papillomavirus Type 16 E7 Protein," *Journal of Virology* 63(6):2650-2656, American Society for Microbiology, United States (1989).

Eisenberg, D., et al., "Analysis of Membrane and Surface Protein Sequences with the Hydrophobic Moment Plot," *J. Mol. Biol.* 179:125-142, Academic Press Inc. (London) Ltd., England (1984).

Estcourt, M.J., et al., "DNA vaccines against human immunodeficiency virus type 1," *Immunological Reviews* 199:144-155, Blackwell Munksgaard, England (2004).

Efangelista, R.L., et al., "Process and Economics Evaluation of the Extraction and Purification of Recombinant β-Glucuronidase from Transgenic Corn," *Biotechnol. Prog.* 14:607-614, American Chemical Society and American Institute of Chemical Engineers, United States (1998).

Galili, G., et al., "Assembly and transport of seed storage proteins," *Trends in Cell Biology* 3:437-443, Elsevier Science Publishers Ltd, England (1993).

Gatta, G., et al., "Survival of European Women with Gynaecological Tumours, During the Period 1978-1989," *Eur J Cancer* 34(14):2218-2225, Elsevier Science Ltd, England (1998).

Geli, M.I., et al., "Two Structural Domains Mediate Two Sequential Events in the γ-Zein Targeting: Protein Endoplasmic Reticulum Retention and Protein Body Formation" *The Plant Cell* 6:1911-1922, American Society of Plant Physiologists, United States (1994).

Halsey, R.J., et al., "Chimaeric HIV-1 subtype C Gag molecules with large in-frame C-terminal polypeptide fusions form virus-like particles," *Virus Research* 133:259-268, Elsevier B.V., Netherlands (2008).

Hennegan, K., et al., "Improvement of human lysozyme expression in transgenic rice grain by combining wheat (*Triticum aestivum*) puroindoline b and rice (*Oryza sativa*) Gt1 promoters and signal peptides," *Transgenic Research* 14:583-592, Springer, Germany (2005).

Herman, E.M. and Larkins, B.A., "Protein Storage Bodies and Vacuoles," *The Plant Cell* 11:601-613, American Society of Plant Physiologists, United States (1999).

Horn, M.E., et al., "Plant molecular farming: systems and products," *Plant Cell Rep* 22:711-720, Springer-Verlag, Germany (2004).

Hurkman, W.J., et al., "Subcellular Compartmentalization of Maize Storage Proteins in Xenopus Oocytes Injected with Zein Messenger RNAs," *The Journal of Cell Biology* 89:292-299, The Rockefeller University Press, United States (1981).

Jaffray, A., et al., "Human immunodeficiency virus type 1 subtype C Gag virus-like particle boost substantially improves the immune response to a subtype C gag DNA vaccine in mice," *Journal of General Virology* 85:409-413, SGM, England (2004).

Jutras, I. and Desjardins, M., "Phagocytosis: At the Crossroads of Innate and Adaptive Immunity," *Annu. Rev. Cell Dev. Biol.* 21:511-527, Annual Review, United States (2005).

Kahn, S.J. and Wleklinski, M., "The Surface Glycoproteins of *Trypanosoma cruzi* Encode a Superfamily of Variant T Cell Epitopes," *The Journal of Immunology* 159:4444-4451, American Association of Immunologists, United States (1997).

Kaufmann, S.H.E. and Schaible, U.E., "Antigen presentation and recognition in bacterial infections," *Current Opinion in Immunology* 17:79-87, Elsevier Ltd., England (2005).

Kelly, M.A., et al., "Host-Guest Study of Left-Handed Polyproline II Helix Formation," *Biochemistry* 40(48):14376-14383, American Chemical Society, United States (2001).

Kent, S.B.H. et al., "Precise Location of a Continuous Epitope in the Pre-S-gene-coded Envelope Proteins of Hepatitis-B Virus," *Vaccines* 86:365-369, Cold Spring Harbor Laboratory, United States (1986).

Kim, C.S., et al., "Zein Protein Interactions, Rather Than the Asymmetric Distribution of Zein mRNAs on Endoplasmic Reticulum Membranes, Influence Protein Body Formation in Maize Endosperm," *The Plant Cell* 14:655-672, American Society of Plant Biologists, United States (2002).

Von Knebel Doeberitz, M., et al., "Reversible Repression of Papillomavirus Oncogene Expression in Cervical Carcinoma Cells: Consequences for the Phenotype and E6-p53 and E7-pRB Interactions," *Journal of Virology* 68(5):2811-2821, American Society for Microbiology, United States (1994).

Knighton, D.R. et al., "Structure of a Peptide Inhibitor Bound to the Catalytic Subunit of Cyclic Adenosine Monophosphate-Dependent Protein Kinase," *Science* 253:414-420, American Association for the Advancement of Science, United States (1991).

Kogan, M.J., et al., "Exploring the Interaction of the Surfactant N-Terminal Domain of γ-Zein with Soybean Phosphatidylcholine Liposomes," *Biopolymers* 73:258-268, Wiley Periodicals, Inc., United States (2003).

Kogan, M.J., et al., "Self-assembly of the Amphipathic Helix (VHLPPP)$_8$. A Mechanism for Zein Protein Body Formation," *J. Mol. Biol.* 312:907-913, Academic Press, United States (2001).

Kogan, M.J., et al., "Supramolecular Properties of the Proline Rich γ-Zein N-Terminal Domain," *Biophysical Journal* 83:1194-1204, Biophysical Society, United States (2002).

Lau, A.H. and Thomson, A.W., "Dendritic cells and immune regulation in the liver," *Gut* 52:307-314, British Medical Association, England (2003).

Letvin, N.L., et al., "Potent, protective anti-HIV immune responses generated by bimodal HIV envelope DNA plus protein vaccination," *Proc. Natl. Acad. Sci.* 94:9378-9383, The National Academy of Sciences, United States (1997)

Leung, L., "Immunogenicity of HIV-1 Env and Gag in baboons using a DNA prime/protein boost regimen," *AIDS* 18(7):991-1001, Lippincott Williams & Wilkins, England (2004).

Lim, W.A., et al., "Structural determinants of peptide-binding orientation and of sequence specificity in SH3 domains," *Nature* 372:375-379, Nature Publishing Group, England (1994).

Ludevid, M.D., et al., "Subcellular localization of glutelin-2 in maize (*Zea mays* L.) endosperm," *Plant Molecular Biology* 3:227-234, Martinus Nijhoff/Dr W. Junk Publishers, Netherlands (1984).

Ma, J.K.-C., et al., "Generation and Assembly of Secretory Antibodies in Plants," *Science* 268:716-719, American Association for the Advancement of Science, United States (1995).

Ma, K., et al., "Polyproline II Helix Is a Key Structural Motif of the Elastic PEVK Segment of Titin," *Biochemistry* 40:3427-3438, American Chemical Society, United States (2001).

Mainieri, D., et al., "Zeolin. A New Recombinant Storage Protein Constructed Using Maize γ-Zein and Bean Phaseolin," *Plant Physiology* 136:3447-3456, American Society of Plant Biologists, United States (2004)

Matsushima, R., et al., "A novel ER-derived compartment, the ER body, selectively accumulates a β-glucosidase with an β-retention signal in Arabidopsis," *The Plant Journal* 33:493-502, Blackwell Publishing Ltd, England (2003).

(56) References Cited

OTHER PUBLICATIONS

Menkhaus, T.J., et al., "Considerations for the Recovery of Recombinant Proteins from Plants," *Biotechnol Prog.* 20:1001-1014, American Chemical Society and American Institute of Chemical Engineers, United States (2004).
Mergener, K., et al., "Analysis of HIV Particle Formation Using Transient Expression of Subviral Constructs in Mammalian Cells," *Virology* 186:25-39, Academic Press, Inc., United States (1992).
Michel, N., et al., "Enhanced Immunogenicity of HPV 16 E7 Fusion Proteins in DNA Vaccination," *Virology* 294:47-59, Elsevier Science, United States (2002).
Milich, D.R., et al., "An Immune Response to the Pre-S1 Region Can Bypass Nonresponse to the Pre-S2 and S Regions of HBsAg," *Vaccines* 87:50-55, Cold Spring Harbor Laboratory, United States (1987).
Montefiori, D.C., et al., "Neutralizing Antibodies Associated with Viremia Control in a Subset of Individuals after Treatment of Acute Human Immunodeficiency Virus Type 1 Infection," *Journal of Virology* 75(21):10200-10207, American Society for Microbiology, United States (2001).
Münger, K., et al., "Interactions of HPV E6 and E7 Oncoproteins with Tumour Suppressor Gene Products," *Cancer Surveys* 12:197-217, Imperial Cancer Research Fund, England (1992).
Muñoz, N., et al., "Epidemiologic Classification of Human Papillomavirus Types Associated with Cervical Cancer," *N Engl J Med* 348(6):518-527, Massachusetts Medical Society, United States (2003).
Neurath, A.R., et al., "Immune Response to Hepatitis-B Virus Determinants Coded by the Pre-S Gene," *Vaccines* 85:185-189, Cold Spring Harbor Laboratory, United States (1986).
Novitsky, V., et al., "Magnitude and Frequency of Cytotoxic T-Lymphocyte Responses: Identification of Immunodominant Regions of Human Immunodeficiency Virus Type 1 Subtype C," *Journal of Virology* 76(20):10155-10168, American Society for Microbiology, United States (2002).
Öhlschläger, P., et al., "An improved rearranged Human Papillomavirus Type 16 E7 DNA vaccine candidate (HPV-16 E7SH) induces an E7 wildtype-specific T cell response," *Vaccine* 24:2880-2893, Elsevier Ltd., United States (2006).
Ohta, N., et al., "Epitope Analysis of Human T-Cell Response to MSP-1 of *Plasmodium falciparum* in Malaria-Nonexposed Individuals," *Int Arch Allergy Immunol* 114:15-22, S. Karger AG, Basel, Switzerland (1997).
Okita, T.W. and Rogers, J.C., "Compartmentation of Proteins in the Endomembrane System of Plant Cells," *Annu. Rev. Plant Physiol. Plant Mol. Biol.* 47:327-350, Annual Reviews Inc., United States (1996).
Osen, W., et al., "A DNA vaccine based on a shuffled E7 oncogene of the human papillomavirus type 16 (HPV 16) induces E7-specific cytotoxic T cells but lacks transforming activity," *Vaccine* 19:4276-4286, Elsevier Science Ltd., England (2001).
Pal, R., et al., "Immunization of rhesus macaques with a polyvalent DNA prime/protein boost human immunodeficiency virus type 1 vaccine elicits protective antibody response against simian human immunodeficiency virus of R5 phenotype," *Virology* 348:341-353, Elsevier Inc., United States (2006).
Paliard, X., et al, "Priming of Strong, Broad, and Long-Lived HIV Type 1 p55gag-Specific CD8+ Cytotoxic T Cells after Administration of a Virus-Like Particle Vaccine in Rhesus Macaques," *AIDS Research and Human Retroviruses* 16(3):273- 282, Mary Ann Liebert, Inc., United States (2000).
Petruccelli, S., et al., "A KDEL-tagged monoclonal antibody is efficiently retained in the endoplasmic reticulum in leaves, but is both partially secreted and sorted to protein storage vacuoles in seeds," *Plant Biotechnology* 4: 511-527, Blackwell Publishing Ltd., England (2006).
Pompa, A. and Vitale, A., "Retention of a Bean Phaseolin/Maize γ-Zein Fusion in the Endoplasmic Reticulum Depends on Disulfide Bond Formation," *The Plant Cell* 18:2608-2621, American Society of Plant Biologists, United States (2006).

Rabanal, F., et al., "CD of Proline-Rich Polypeptides: Application to the Study of the Repetitive Domain of Maize Glutelin-2," *Biopolymers* 33:1019-1028, John Wiley & Sons, Inc., United States (1993).
Rafalski, J.A., et al., "Developmentally regulated plant genes: the nucleotide sequence of a wheat gliadin genomic clone," *The EMBO Journal* 3(6):1409-1415, IRL Press Limited, Oxford, England (1984).
Randall, J., et al., "A modified 10 kD zein protein produces two morphologically distinct protein bodies in transgenic tobacco," *Plant Science* 150:21-28, Elsevier Science Ireland Ltd., Ireland (2000).
Renzoni, D.A., et al., "Structural and Thermodynamic Characterization of the Interaction of the SH3 Domain from Fyn with the Proline-Rich Binding Site on the p85 Subunit of PI3-Kinase," *Biochemistry* 35:15646-15653, American Chemical Society, United States (1996).
Richter, L.Z., et al., "Production of hepatitis B surface antigen in transgenic plants for oral immunization," *Nature Biotechnology* 18:1167-1171, Nature Publishing Company, United States (2000).
Robinson, H.L., "DNA vaccines: Basic mechanism and immune responses (Review)," *International Journal of Molecular Medicine* 4:549-555, Spandidos, Greece (1999).
Van Rooijen, G.J.H. and Moloney, M.M., "Plant Seed Oil-bodies as Carriers for Foreign Proteins," *Bio/Technology* 13:72-77, Nature Pub. Co., United States (1995).
Rosenberg, N., et al., "Wheat (*Triticum aestivum* L.) γ-Gliadin Accumulates in Dense Protein Bodies within the Endoplasmic Reticulum of Yeast," *Plant Physiol.* 102:61-69, American Society of Plant Biologists, United States (1993).
Rucker, A.L., et al., "Host-Guest Scale of Left-Handed Polyproline II Helix Formation," *Proteins: Structure, Function and Genetics* 52:68-75, Wiley-Liss, INC., United States (2003).
Sakuragi, S., et al., "HIV type 1 Gag virus-like particle budding from spheroplasts of *Saccaromyces cerevisiae*," *PNAS* 99(12):7956-7961, National Academy of Sciences, United States (2002).
Sanderfoot, A.A. and Raikhel, N.V., "The Specificity of Vesicle Trafficking: Coat Proteins and SNAREs," *The Plant Cell* 11:629-641, American Society of Plant Physiologists, United States (1999).
Saron, M.F., et al., "Anti-viral protection conferred by recombinant adenylate cyclase toxins from *Bordetella pertussis* carrying a CD8+ T cell epitope from lymphocytic choriomeningitis virus," *Proc. Natl. Acad. Sci.* 94:3314-3319, The National Academy of Sciences of the USA, United States (1997).
Scheerlinck, J-P. Y. and Greenwood, D.L.V., "Particulate delivery systems for animal vaccines," *Methods* 40:118-124, Elsevier Inc., United States (2006).
Shewry, P.R. and Halford, N.G., "Cereal seed storage proteins: structures, properties and role in grain utilization," *Journal of Experimental Botany* 53(370):947-958, Society for Experimental Biology, England (2002).
Shewry, P.R. and Tatham, A.S., "The prolamin storage proteins of cereal seeds: structure and evolution," *Biochem. J.* 264:1-12, Portland Press, Great Britain (1990).
Shewry, P.R., et al., "Seed Storage Proteins: Structures and Biosynthesis," *The Plant Cell* 7:945-956, American Society of Plant Physiologists, United States (1995).
Shi, W., et al., "Human Papillomavirus Type 16 E7 DNA Vaccine: Mutation in the Open Reading Frame of E7 Enhances Specific Cytotoxic T-Lymphocyte Induction and Antitumor Activity," *Journal of Virology* 9(73):7877-7881, American Society for Microbiology, United States (1999).
Shi, Z., et al., "Polyproline II propensities from GGXGG peptides reveal an anticorrelation with β-sheet scales," *PNAS* 102(50):17964-17968, National Academy of Sciences, United States (2005).
Šmahel., M., et al., "Modified HPV16 E7 Genes as DNA Vaccine against E7-Containing Oncogenic Cells," *Virology* 281:231-238, Academic Press, United States (2001).
Smyth, E., et al., "Solution Structure Of Native Proteins With Irregular Folds From Raman Optical Activity," *Biopolymers* 58:138-151, John Wiley & Sons, Inc., United States (2001).

(56) References Cited

OTHER PUBLICATIONS

Spencer, D.I.R., et al., "Structure/ Activity Studies of the Anti-MUC1 Monoclonal Antibody C595 and Synthetic MUC1 Mucin-Core-Related Peptides and Glycopeptides," *Biospectroscopy* 5:79-91, John Wiley & Sons, Inc., United States (1999).

Staffileno, L.K., et al., "Cloning of the Amino Terminal Nucleotides of the Antigen I/II of *Streptococcus sobrinus* and the Immune Responses to the Corresponding Synthetic Peptides," *Archs oral Biol.* 35:45s-52s, Pergamon Press plc, Great Britain (1990).

Sugiyama, T., et al., "The Nucleotide Sequence of a Wheat γ-Gliadin Genomic Clone," *Plant Science* 44:205-209, Elsevier Scientific Publishers Ireland Ltd., Ireland (1986).

Suh, Y.S., et al., "Reduction of viral loads by multigenic DNA priming and adenovirus boosting in the SIVmac-macaque model," *Vaccine* 24:1811-1820, Elsevier Ltd., England (2006).

Tackaberry, E.S., et al., "Development of pharmaceuticals in plant expression systems, cloning, expressions, and immunological reactivity of human cytomegalovirus glycoprotein B (UL55) in seeds of transgenic tobacco," *Vaccine* 17:3020-3029, Elsevier Science Ltd., Netherlands (1999).

Torrent, M., et al., "In maize, glutelin-2 and low molecular weight zeins are synthesized by membranebound polyribosomes and translocated into microsomal membranes," *Plant Molecular Biology* 7:393-403, Martinus Nijhoff Publishers, Netherlands (1986).

Torrent, M., et al., "Lysine-rich modified γ-zeins accumulate in protein bodies of transiently transformed maize endosperms," *Plant Molecular Biology* 34:139-149, Kluwer Academic Publishers, Belgium (1997).

Torrent, M., et al., "Role of Structural domains for maize γ-zein retention in Xenopus oocytes," *Planta* 192:512-518, Springer-Verlag, Germany (1994).

Twyman, R.M., et al., "Molecular farming in plants: host system and expressions technology," *TRENDS in Biotechnology* 21(12):570-578, Elsevier Ltd., England (2003).

Velders, M.P., et al., "Defined Flanking Spacers and Enhanced Proteolysis Is Essential for Eradication of Established Tumors by an Epitope String DNA Vaccine," *The Journal of Immunology* 166(9):5366-5373, The American Association of Immunologists, United States (2001).

Vergne., I., et al., "Phagosomal pH Determination by Dual Fluorescence Flow Cytomety," *Analytical Biochemistry* 255:127-132, Academic Press, United States (1998).

De Villiers, E-M., et al., "Classification of papillomaviruses," *Virology* 324:17-27, Elsevier Inc., United States (2004).

Wagner, R., et al., "Construction, Expression, and Immunogenicity of Chimeric of HIV-1 Virus-like Particles," *Virology* 220:128-140, Academic Press, Inc., United States (1996).

Wagner, R., et al., "Induction of a MHC Class 1-Restricted, CD8 Positive Cytolytic T-Cell Response by Chimeric HIV-1 Virus-Like Particles in Vivo: Implications on HIV Vaccine Development," *Behring Inst. Mitt.* 95:23-34, Marburg/Lahn: Behringwerke AG, German (1994).

Walboomers, J.M.M., et al., "Human Papillovirus is a Necessary Cause of Invasive Cervical Cancer Worldwide," *J. Pathol.* 189:12-19, John Wiley & Sons, Ltd., United States (1999).

Watanabe, S., et al., "Mutational Analysis of Human Papillomavirus Type 16 E7 Functions," *Journal of Virology* 64(1):207-214, American Society for Microbiology, United States (1990).

Wright, K.E., et al., "Sorting of glycoprotein B from human cytomegalovirus to protein storage vesicles in seeds of transgenic tobacco," *Transgenic Research* 10:177-181, Kluwer Academic Researchers, Netherlands (2001).

Yang, C., et al., "Induction of protective antibodies in Saimiri monkeys by immunization with a multiple antigen construct (MAC) containing the *Plasmodium vivax* circumsporozoite protein repeat region and a universal T helper epitope of tetanus toxin," *Vaccine* 15(4):377-386, Elsevier Science Ltd., Great Britain (1997).

Yang, D., et al., "Expression and localization of human lysozyme in the endosperm of transgenic rice," *Planta* 216:597-603, Springer-Verlag, Germany (2003).

Yasutomi, Y., et al., "Simian Immunodeficiency Virus-Specific Cytotoxic T-Lymphocyte Induction through DNA Vaccination of Rhesus Monkeys," *Journal of Virology* 70(1):678-681, American Society for Microbiology, United States (1996).

Zhong, W., et al., "Plasmid DNA and a protein vaccination of mice to the outer surface protein A of *Borrelia burgdorferi* leads to induction of T helper cells with specificity for a major epitope and augmentation of protective IgG antibodies in vivo," *Eur. J Immunol.* 26:2749-2757, VCH Verlagsgesellschaft mbH, Weinheim, Germany (1996).

Syme, C.D., et al., "A Raman optical activity study of rheomorphism in caseins, synucleins and tau: New insight into the structure and behavior of natively unfolded proteins," *Eur. J. Biochem.* 269:148-156, FEBS, England (2002).

International Search Report for International Application No. PCT/EP2009/063223, European Patent Office, The Hague, Netherlands, mailed on Jun. 11, 2010 International Search Report for International Application No. PCT/EP2011/058864.

International Search Report for International Application No. PCT/EP2011/058864, European Patent Office, The Hague, Netherlands, mailed on Nov. 15, 2011.

Alvarez, I., et al., "Lysine rich γ-zeins are secreted in transgenic Arabidopsis plants," *Planta* 205:420-427, Springer-Verlag, Germany (1998).

Cameron-Mills, V., "The Structure and Composition of Protein Bodies Purified From Barley Endosperm by Silica Sol Density Gradients," *Carlsberg Res. Commun.* 45:557-576, Springer-Verlag, Germany (1980).

Ems-McClung, S.C., et al., "Mutational analysis of the maize gamma zein C-terminal cysteine residues," *Plant Science* 162:131-141, Elsevier Science Ireland Ltd., Ireland (2002).

Richard, G., et al., "Transport and deposition of cereal prolamins," *Plant Physiol. Biochem.* 34(2):237-243, Gauthier-Villars, France (1996).

Miflin, B.J., et al., "The Development of Protein Bodies in the Storage Tissues of Seeds: Subcellular Separations of Homogenates of Barley, Maize, and Wheat Endosperms and of Pea Cotyledons," *Journal of Experimental Botany* 32(126):199-219, Oxford University Press, England (1981).

Philip, R., et al., "Localization of β-glucuronidase in protein bodies of transgenic tobacco seed by fusion to an amino terminal sequence of the soybean lectin gene," *Plant Science* 137:191-204, Elsevier Science Ireland Ltd., Ireland (1998).

Sojikul, P., et al., "A plant signal peptide-hepatitis B surface antigen fusion protein with enhanced stability and immunogenicity expressed in plant cells," *PNAS* 100(5):2209-2214, National Academy of Sciences, United States (2003).

Takagi, H., et al., "A rice-based edible vaccine expressing multiple T cell epitopes induces oral tolerance for inhibition of Th2-mediated IgE responses," *PNAS* 102(48):17525-17530, National Academy of Sciences, United States (2005).

Baccanari, D., et al., "Purification and Properties of *Escherichia coli* Dihydrofolate Reductase," *Biochemistry* 14(24):5267-5273, American Chemical Society, United States (1975).

Barteri, M., et al., "Low Frequency ultrasound induces aggregation of porcine fumarase by free radicals production," *Biophysical Chemistry* 111:35-42, Elsevier B.V., Netherlands (2004).

Castellanos, U., et al., "Encapsulation-induced aggregation and loss in activity of γ-chymotrypsin and their prevention," *Journal of Controlled Release* 81:307-319, Elsevier Science B.V., Netherlands (2002).

Greenberg, S. and Grinstein, S., "Phagocytosis and innate immunity," *Curr. Opin. Immunol.* 14:136-145, Elsevier Science Ltd., England (2002).

Llop-Tous, I., et al., "The Expression of a Xylanase Targeted to ER-Protein Bodies Provides a Simple Strategy to Produce Active Insoluble Enzyme Polymers in Tobacco Plants," *PLoS ONE* 6(4):e19474, 11 pages, Public Library of Science, United States (2011).

Llop-Tous, I., et al., "Relevant Elements of a Maize γ-Zein Domain Involved in Protein Body Biogenesis," *The Journal of Biological Chemistry* 285(46):35633-35644, The American Society for Biochemistry and Molecular Biology, Inc., United States (2010).

(56) References Cited

OTHER PUBLICATIONS

Torrent, M., el al., "Eukaryotic protein production in designed storage organelles," *BMC Biology* 7(5),14 pages, BioMed Central Ltd., England (2009).

Tsumoto, K., et al., "Solubilization of active green fluorescent protein from insoluble particles by guanidine and arginine," *Biochemical and Biophysical Research Communications* 312:1383-1386, Elsevier Inc., United States (2003).

Zupan, A.L., et al., "High expression of green fluorescent protein in *Pichia pastoris* leads to formation of fluorescent particles," *Journal of Biotechnology* 109:115-122, Elsevier B.V., Netherlands (2004).

Anderson, W.F., "Human gene therapy," *Nature* 392(6679 Suppl):25-30, Nature Publishing Group, England (Apr. 1998).

Cramer, C.L., et al., "Transgenic Plants for Therapeutic Proteins: Linking Upstream and Downstream Strategies," *Curr. Top. Microbial. Immunol.* 240:95-118, Springer-Verlag, Germany (1999).

Ems-McClung, S.C. and Hainline, B.E., "Expression of Maize Gamma Zein C-Terminus in *Escherichia coli*," *Protein Expression and Purification* 13:1-8, Academic Press, United States (1998).

Engelhard, E., et al., "The insect tracheal system: A conduit for the systemic spread of *Autographa californica* M Nuclear polyhedrosis virus," *Proc Natl Acad Sci, USA* 91: 3224-3227, National Academy of Science, US (1994).

Fernández-Carneado, J., et al., "Potential Peptide Carriers: Amphipathic Proline-Rich Peptides Derived from the N-Terminal Domain of γ-Zein," *Angewandte Chemie* 43:1811-1814, Wiley-VCH Verlag GmbH & Co., Germany (2004).

Goytia, E., et al., "Production of plum pox virus HC-Pro functionally active for aphid transmission in a transient-expression system," *J Gen Virol* 37: 3413-3423, SGM, GB (2006).
Haq, T. A., et al., "Oral Immunization with a Recombinant Bacterial Antigen Produced in Transgenic Plants," *Science* 268:714-716, American Association for the Advancement of Science , United States (May 1995).
Luckow, V., et al., "Efficient Generation of Infectious Recombinant Baculoviruses by Site-Specific Transposon-Mediated Insertion of Foreign Genes into a Baculovirus Genome Propagated in *Escherichia coli*," *J Virol* 67(8): 5466-4579, American Society for Microbioloy, US (1993).
Odell, J., et al, "Identification of DNA sequences required for activity of the cauliflower mosaic virus 35S promoter," *Nature* 313: 810-812, Nature Publishing Group, UK (1985).
Thompson, S., et al., "High-Level Expression of a Wheat LMW Glutenin Subunit Using a Baculovirus System," *J. Agric. Food Chem.* 42:426-431, America Chemical Society, United States (1994).
Verma, I.M. and Somia, N., "Gene therapy—promises, problems and prospects," *Nature* 389(6648):239-42, Nature Publishing Group, England (Sep. 1997).
Wallace, J., et al., "Aggregation of Lysine-Containing Zeins into Protein Bodies in Xenopus Oocytes," *Science* 240: 662-664, American Association for the Advancement of Science, US (1988).

* cited by examiner

RX3-p24 antigen

RX3-p41 antigen

RX3-RT antigen

RECOMBINANT PROTEIN BODIES AS IMMUNOGEN-SPECIFIC ADJUVANTS

CROSS-REFERENCE TO RELATED APPLICATIONS

This is a U.S. National Phase of International Appl. No. PCT/EP2009/063223, filed on Oct. 9, 2009, which claims benefit of priority of U.S. application Ser. No. 61/104,403 filed on October 2008, each of which is hereby incorporated by reference in its entirety and is a Continuation-in-Part of copending U.S. patent application Ser. No. 11/709,527 filed on Feb. 22, 2007, now U.S. Pat. No. 8,163,880 issued on Apr. 24, 2012, which claims priority to Provisional Application No. 60/776,391 filed on Feb. 23, 2006.

REFERENCE TO A SEQUENCE LISTING SUBMITTED ELECTRONICALLY VIA EFS-WEB

The content of the electronically submitted sequence listing (Name: sequencelisting_ascii.txt, Size: 103,230 bytes; and Date of Creation: Jul. 5, 2011) is herein incorporated by reference in its entirety.

TECHNICAL FIELD

The present invention provides an immunogen-specific adjuvant for a vaccine or inoculum. More specifically, the invention provides a vaccine or inoculum adjuvant comprising recombinant protein body-like assemblies (RPBLAs) that contain a recombinant fusion protein. The recombinant fusion protein contains two sequences that are peptide-linked together in which one sequence is a protein body-inducing sequence (PBIS) and the other is a T-cell stimulatory polypeptide that corresponds to a portion of a pathogenic polypeptide sequence present in or encoded by a vaccine or inoculum.

BACKGROUND ART

Protein bodies (PBs) are subcellular organelles (or large vesicles, about 1-3 microns in diameter, surrounded by a membrane) that specialize in protein accumulation. They are naturally formed in some specific plant tissues, like seeds, and serve as principal source of amino acids for germination and seedling growth.

The storage proteins are co-translationally inserted into the lumen of the endoplasmic reticulum (ER) via a signal peptide to be packaged either in the ER or into the vacuoles (Galili et al., 1993 *Trends Cell Biol.* 3:437-443) and assembled into multimeric units inside these subcellular compartments, developing specific organelles called (ER)-derived protein bodies (PBs) or protein storage vacuoles (PSV) (Okita and Rogers, 1996 *Annu. Rev. Plant Physiol Mol. Biol.* 47:327-350; Herman and Larkins, 1999 *Plant Cell* 11:601-613; Sanderfoot and Raikel, 1999 *Plant Cell* 11:629-642).

The storage proteins dicotiledoneous plants are primarily soluble proteins such as the 7S globulin or vicilin type, 11S globulins or legumin-type proteins and are sequestered in PSVs together with other proteins (i.e., protease inhibitors, proteolytic enzymes, lectins and the like), sugars and salts.

In contrast to PSVs, PBs (1-3 microns) sequester predominantly prolamins, which are highly hydrophobic storage proteins of cereals (such as zeins of maize and gliadins of wheat), and lack of other auxiliary proteins (Herman et al., 1999 *Plant Cell* 11:601-613).

At present, no PBs have been found in tissues other than plant seeds, with the exception of the ER bodies. The ER bodies are small in size (0.2-0.4 micrometers) and are formed in *Arabidopsis* leaves only by wounding and chewing by insects but do not develop under normal conditions (Matsushima et al., 2003 *Plant J.* 33:493-502).

Genetic engineering approaches have been used to study plant PBs formation, storage protein assembly and targeting. It has been shown that when recombinant proteins, predominantly plant storage proteins are expressed and packaged in *Arabidopsis* and tobacco, plant tissues that did not contain PBs (as vegetative tissues), develop these organelles "de novo" (Bagga et al., 1997 *Plant Cell* 9:1683-1696 and Bagga et al., 1995 *Plant Physiol.* 107:13-23, and U.S. Pat. No. 5,990,384, U.S. Pat. No. 5,215,912, and U.S. Pat. No. 5,589,616; and Geli et al., 1994 *Plant Cell* 6:1911-1922).

Maize beta-zein when expressed in transgenic tobacco plants was correctly targeted in new formed ER-derived PBs in leaf cells (Bagga et al., 1995 *Plant Physiol.* 107:13-23). Maize gamma-zein and, truncated gamma-zein cDNAs expressed in *Arabidopsis* plants also accumulate in a novel ER-derived PBs in leaves (Geli et al., 1994 *Plant Cell* 6:1911-1922). Lysine-rich gamma-zeins expressed in maize endosperms (Torrent et al. 1997 *Plant Mol. Biol.* 34(1):139-149) accumulate in maize PBs and co-localized with endogenous zeins. Transgenic tobacco plants expressing alpha-zein gene demonstrated that alpha-zein was not able to form PBs. However, when alpha- and gamma-zein were co-expressed, the stability of alpha-zein increased and both proteins co-localized in ER-derived protein bodies (Coleman et al., 1996 *Plant Cell* 8:2335-2345). Formation of novel PBs has been also described in transgenic soybean transformed with methionine-rich 10 kDa delta-zein (Bagga et al., 2000 *Plant Sci.* 150:21-28).

Recombinant storage proteins are also assembled in PBs-like organelles about 100 to about 400 nm in diameter in a non-plant host system such as *Xenopus oocytes* and in yeast. Rosenberg et al., 1993 *Plant Physiol* 102:61-69 reported the expression of wheat gamma-gliadin in yeast. The gene expressed correctly and the protein was accumulated in ER-derived PBs. In *Xenopus oocytes*, Torrent et al., 1994 Planta 192:512-518 demonstrated that gamma zein also accumulates in PB-like organelles when transcripts encoding the protein were microinjected into oocytes. Hurkman et al., 1981 *J. Cell Biol.* 87:292-299 with alfa-zeins and Altschuler et al., 1993 *Plant Cell* 5:443-450 with gamma-gliadins had similar results in *Xenopus oocytes*.

One of the fundamental achievements of the field of the biotechnology (genetic engineering) is the ability to genetically manipulate an organism to produce a protein for therapeutic, nutraceutical or industrial uses. Methods are provided for producing and recovering recombinant proteins from fermentation broth of bacteria, yeast, crop plants and mammalian cell cultures. Different approaches for protein expression in host cells have been described. The essential objectives of these approaches are: protein expression level, protein stability and protein recovery (Menkhaus et al., 2004 *Biotechnol. Prog.* 20: 1001-1014; Evangelista et al., 1998 *Biotechnol. Prog.* 14:607-614).

One strategy that can solve a problem with protein recovery is secretion. However, secretion involves some times poor expression levels and product instability. Another strategy is the accumulation of the recombinant protein in the most beneficial location in the cell. This strategy has been extensively used by directing recombinant proteins to the ER by engineering C-terminal extension of a tetrapeptide (HDEL/KDEL) (Conrad and Fiedler, 1998 *Plant Mol. Biol.* 38:101-109).

Fusion proteins containing a plant storage protein or storage protein domains fused to the heterologous protein have been an alternative approach to direct recombinant proteins to the ER (WO 2004003207). One interesting fusion strategy is the production of recombinant proteins fused to oleosins, constitutive protein of plant oil bodies. The specific characteristics of oil bodies benefit of the easy recovery of proteins using a two-phase system (van Rooijen and Moloney, 1995 *Bio/Technology* 13:72-77).

Heterologous proteins have been successfully expressed in plant cells (reviews Horn et al., 2004 *Plant Cell Rep.* 22:711-720; Twyman et al., 2003, *Trends in Biotechnology* 21:570-578; Ma et al., 1995, *Science* 268: 716-719; Richter et al., 2000 *Nat. Biotechnol.* 18:1167-1171), and in some, the expression of the recombinant protein has been directed to ER-derived PB or PSV (PSV). Yang et al., 2003 Planta 216:597-603, expressed human lysozyme in rice seeds using the seed-specific promoters of glutelin and globulin storage proteins. Immunocytochemistry results indicated that the recombinant protein was located in ER-PBs and accumulated with endogenous rice globulins and glutelins. The expression of glycoprotein B of the human cytomegalovirus (hCMV) in transgenic tobacco plants has been carried out using a glutelin promoter of rice. Tackaberry et al., 1999 *Vaccine* 17:3020-3029. Recently, Arcalis et al., 2004 *Plant Physiology* 136:1-10 expressed human serum albumin (HSA) with a C-terminal extension (KDEL) in rice seeds. The recombinant HSA accumulated in PSVs with the endogenous rice storage proteins.

One obstacle for the application of plants as biofactories is the need for more research regarding the downstream processing. Protein purification from plants is a difficult task due to the complexity of the plant system. Plant solids of the extract are large, dense and relative elevated (9-20 percent by weight) (see review Menkhaus et al., 2004 *Biotechnol. Prog.* 20:1001-1014). At present, recombinant protein purification techniques include clarification of the extracts, treatment with solvents to remove lipids and pigments and protein or peptides purification by several ion-exchange and gel-filtration chromatography columns. The existing protocols rely upon the use of specific solvents or aqueous solutions for each plant-host system and recombinant protein. There is a need in the art for efficient and general procedures for recombinant protein recovery from transformed hosts. This need is especially relevant in cases where recombinant proteins produced in plant hosts must to be isolated. The diversity of hosts and proteins and the different physical-chemical traits between them required an efficient method to concentrate and recover recombinant products.

Immunologic adjuvants are agents that enhance specific immune responses to vaccines and inocula. An immunologic adjuvant can be defined as any substance or formulation that, when incorporated into a vaccine or inoculum, acts generally or specifically to accelerate, prolong, or enhance the quality of specific immune responses to the immunogenic materials in the preparation.

The word adjuvant is derived from the Latin verb adjuvare, which means to help or aid. Adjuvant mechanisms of action include the following: (1) increasing the biological or immunologic half-life of vaccine or inoculum immunogens; (2) improving immunogen delivery to antigen (immunogen)-presenting cells (APCs), as well as antigen (immunogen) processing and presentation by the APCs; and (3) inducing the production of immunomodulatory cytokines.

Possession of biological activity that resembles an activity of a natural pathogen or other agent is particularly relevant for vaccines or inocula, which must induce a correct immune response in an immunized human or other animal to be effective. Several new vaccines and inocula are composed of synthetic, recombinant, or highly purified subunit immunogens (antigens) that are thought to be safer than whole-inactivated or live-attenuated vaccines. However, pathogen-related immunomodulatory adjuvant components that are typically associated with attenuated or killed pathogen vaccines are absent from such synthetic, recombinant, or highly purified subunit immunogens, which often results in weaker immunogenicity for such preparations.

Phagocytosis involves the entry of large particles, such us apoptotic cells or whole microbes, into another cell. The capacity of the cells to engulf large particles likely appeared as a nutritional function in unicellular organisms; however complex organisms have taken advantage of the phagocytic machinery to fulfill additional functions. For instance, the phagocytosis of immunogens undertaken by the macrophages, the B-cells or the dendritic cells represents a key process in innate and adaptive immunity. Indeed, phagocytosis and the subsequent killing of microbes in phagosomes form the basis of an organism's innate defense against intracellular pathogens. Furthermore, the degradation of pathogens in the phagosome lumen and the production of antigenic peptides, which are presented by phagocytic cells to activate specific lymphocytes, also link phagocytosis to adaptive immunity (Jutras et al., 2005 *Annual Review in Cell Development Biology.* 21:511-527).

The proteins present on and in engulfed particles encounter an array of degrading proteases in phagosomes. Yet, this destructive environment generates peptides that are capable of binding to MHC class II molecules. Newly formed immunogen-MHC class II complexes are delivered to the cell surface for presentation to CD4+ T cells (Boes et al., 2002 *Nature* 418:983-988). The activation of these cells induces the Th2 subset of cytokines such as IL-4 and IL-5 that help B cells to proliferate and differentiate, and is associated with humoral-type immune response.

A large body of evidence indicates that, in addition to the clear involvement of the MHC class II pathway in the immune response against phagocytosed pathogens, immunogens from pathogens, including mycobacteria, *Salmonella*, *Brucella*, and *Leishmania*, can elicit an immunogen cross-presentation. That is to say, the presentation of an engulfed immunogen by phagocytosis by the MHC class I-dependent response promotes the proliferation of CD8+ cytotoxic T cells (Ackerman et al., 2004 *Nature Immunology* 5(7):678-684; Kaufmann et al., 2005 *Current Opinions in Immunology* 17(1):79-87).

Dendritic cells play a central immunogen presentation role to induce the immune system (Blander et al., *Nature Immunology* 2006 10:1029-1035). Although rare, dendritic cells are the most highly specialized APC, with ability both to instigate and regulate immune reactivity (Lau et al. 2003 *Gut* 52:307-314). Although dendritic cells are important in presenting immunogens, particularly to initiate primary immune responses, macrophages are the APC type most prominent in inflammatory sites and specialized for clearing necrotic and apoptotic material. Macrophages can act not only as APC, but can also perform either pro- or anti-inflammatory roles, dependent on the means by which they are activated.

Considering that APCs play a central role in the induction and regulation of the adaptive immunity (humoral and cellular), the recognition and phagocytosis of the immunogen by those cells can be considered a key step in the immunization process. A wide variety of techniques based on the uptake of fluorescent particles have been developed to study phagocytosis by the macrophages (Vergne et al., 1998 *Analytical Biochemistry* 255:127-132).

An important aspect in veterinary vaccines is the genetic diversity of the species being considered and the requirement for generic systems that work across different species. To a large degree, this diversity limits the use of molecular targeting techniques to cell surface markers and immune modulators such as cytokines, because for many species including wildlife, only minimal knowledge of these molecules is available. Thus, adjuvants that rely on universal activation signals of the innate immune response (i.e. that are identical in different species) are to be preferred. Taking these requirements into consideration, particulate vaccine delivery systems are well suited for veterinary and wildlife vaccine strategies (Scheerlinck et al., 2004 *Methods* 40:118-124).

In Third World countries, cervical cancer (cc) is one of the major causes of cancer-related deaths. About 80% of women dying from this disease originate from low-budget countries where screening programs for early detection and the medical infrastructure for treatment are not available. In contrast, in the more developed world the mortality was reduced (by 70% in the US) during the last 50 years as a consequence of cytological screening programs [American Cancer Society, Cancer facts and figures 2004. Atlanta, Ga.] Treatment of cc patients by surgery, radiotherapy or chemotherapy results in a significant loss of quality of life. Even when optimal treatment is available about 40% of all cc patients die of this disease [Gatta et al., 1998 *Eur J Cancer* 34(14 Spec. No.):2218-2225]. Therefore, the development of an effective and save therapeutic vaccine is needed.

A necessary event for the development of premalignancies like cervical intraepithelial neoplasia (CIN) and cc is infection by hr-HPVs [Walboomers et al., 1999 *J Pathol* 189(1):12-19]. So far over 120 HPV types are identified [de Villiers et al., 2004 *Virology* 324(1):17-27], 18 of which were found to be associated with cc [Munoz et al., 2003 *N Engl J Med* 348(6):518-527].

HPV-16 is responsible for about 50% of the cases [Bosch et al., 1995 *J Natl Cancer Inst* 87(11):796-802]. Due to the fact that the oncoprotein E7 of the hr-HPVs is exclusively and consistently expressed by HPV-infected tumor cells [von Knebel Doeberitz et al., 1994 *J Virol* 68(5):2811-2821], that protein represents a specific target for an immune therapy directed against cc and its premalignant dysplasia. The E7 protein, however, is an oncoprotein with transforming activity that operates by interfering with the cell cycle control. The E7 alters cell growth regulation by inactivating the pRB (retinoblastoma) tumor suppressor protein [Dyson et al., 1989 Science 243(4893):934-937; Munger et al., 1992 *Cancer Surv* 12:197-217] and contains two metal-binding motifs (C-XX-C) [Edmonds et al., 1989 *J Virol* 63(6):2650-2656; Watanabe et al., 1990 *J Virol* 64(1):207-214].

For safety reasons a functional oncogene cannot be applied to humans. Therefore, efforts were made to inactivate the oncogenic properties of the HPV-16 E7. Some investigators have introduced point mutations into the sites of the E7-oncogene that are associated with transforming potential [Shi et al., 1999 *J Virol* 73(9):7877-7881; Smahel et al., 2001 *Virology* 281(2):231-238], whereas others have used HLA- (human leukocyte antigen) restricted singular epitopes [Doan et al., 2000 Cancer Res 60(11):2810-2815; Velders et al., 2001 *J Immunol* 166(9):5366-5373]. These approaches, however, can lead to an unwanted loss of a naturally occurring epitope that is potentially associated with a decrease in vaccine efficacy.

An aim of the present inventors was to supply several to all potential naturally occurring T cell epitopes, covering the broad range of MHC restriction. In consequence, prior knowledge of the patient's HLA-haplotype is not required. This is especially important in the outbred human population.

In addition, a more potent immune response may be induced, involving all occurring HLA-restriction elements in the vaccine. A "proof-of-principle" was generated in a study using an artificial HPV-16 E7 gene (HPV-16 E7SH) of the first generation [Osen et al., 2001 *Vaccine* 19(30):4276-4286]. It was shown in that study that an oncoprotein with a rearranged primary sequence still induces E7WT-specific CTLs in mice but is devoid of transforming properties. That study took advantage of the earlier finding that fusion with the VP22 gene of Herpes Simplex Virus Type 1 strongly enhances the CTL response in mice [Michel et al., 2002 *Virology* 294(1):47-59].

The HIV-1 virus is comprised of several layers of proteins and glycoproteins that surround its RNA, and its associated proteins integrase and reverse transcriptase. The RNA is encapsidated by a capsid protein (CA), p24. The capsid environment also contains other viral proteins such as integrase and reverse transcriptase. The capsid is in turn encapsidated by a layer of matrix protein (MA), p17. This matrix protein is associated with a lipid bilayer or envelope.

The great diversity among human immunodeficiency virus type 1 (HIV-1) subtypes, which are prevalent in various regions of the world, is a major impediment to the development of broad-based prophylactic HIV-1 vaccines. Thus, it may be necessary to develop vaccines that match local epidemics more closely (Morris et al., 2001). In southern Africa, subtype C infections predominate (UN-AIDS, 2006), and isolates of this subtype have been selected for the development of a DNA vaccine in South Africa (Williamson et al., 2003). This candidate vaccine has been constructed and characterized (van Harmelen et al., 2003) and is scheduled to be evaluated in clinical trials shortly.

DNA vaccines encoding HIV or simian immunodeficiency virus (SIV)/simian-human immunodeficiency virus (SHIV) antigens have been studied extensively and shown to induce both humoral and cellular immune responses in animal models as well as in humans [Boyer et al., 1997 *J Infect Dis.* 176(6):1501-1509; Calarota et al., 1998 *Lancet* 351(9112):1320-1325; Estcourt et al., *Immunol. Rev.* 2004 199:144-155; Letvin et al., 1997 Proc Natl Acad Sci USA. 94(17):9378-9383; Yasutomi et al., 1996 *J Virol.* 70(1):678-681]. However, although DNA vaccines have been shown to be safe, immunization generates low and transient levels of immune responses. Various approaches to augment DNA vaccines have been tested [Barouch et al., 2000 *Intervirology* 43(4-6):282-287; Hemmi et al., 2003 *J Immunol* 170 (6):3059-3064; Raviprakash et al., 2003 *Virology.* 315(2): 345-352], including their use in heterologous prime-boost immunization regimens [Casimiro et al., 2003 *J. Virol.* 77(13):7663-7668; Cherpelis et al., 2001 *Immunol Lett.* 79(1-2):47-55; Leung et al., 2004 *AIDS* 18(7):991-1001; Pal et al., 2006 *Virology* 348(2):341-353; Robinson et al., 1999 *Int J Mol. Med.* 4(5):549-555; Suh et al., 2006 *Vaccine* 24(11):1811-1820. Epub 2005 Oct. 25].

The HIV-1 Gag gene encodes the precursor protein Pr55 Gag, which is the major protein that makes up the structure of the HIV viral particle. On maturation of the viral particle, Gag is cleaved by the viral protease into several smaller proteins that include the capsid (CA) protein p24, the matrix protein p17, as well as proteins p7 and p6.

HIV-1 Pr55$^{gag}$ precursor protein possesses an ability to self-assemble into non-replicating and non-infectious virus-like particles (VLPs) [Deml et al., 1997 Virology 235(1): 26-39; Mergener et al., 1992 Virology 186(1):25-39; Sakuragi et al., 2002 Proc Natl Acad Sci USA 99(12):7956-7961; Wagner et al., 1994 Behring Inst Mitt (95):23-34; Wagner et al., 1996 Virology 220(1):128-140], and elicits strong humoral and cellular immune responses in animals [Deml et al., 1997 Virology 235(1):26-39; Deml et al., 2004 Methods Mol Med 94:133-157; Jaffray et al., 2004 J Gen Virol. 85(Pt 2):409-413], including non-human primates (NHPs) (Montefiori et al., 2001 J. Virol. 75(21):10200-10207; Paliard et al., 2000 AIDS Res Hum Retroviruses 16(3):273-282]. Recently, Chege et al., J Gen Virol 2008 89:2214-2227 have shown that subtype C Pr55$^{gag}$ VLPs can very efficiently boost baboons primed with a matched DNA vaccine.

In addition, HIV-1 Pr55$^{gag}$ VLPs are safe, easy to produce and have the potential of including chimeric immunogens (Doan et al., 2005; Halsey et al., 2008). Their particulate nature and size, which approximates that of HIV-1, make HIV-1 Pr55$^{gag}$ VLPs more likely to stimulate the immune system better than non-particulate immunogens.

As above, the p24 protein forms the outer capsid layer of the viral particle. This protein has a high density of cytotoxic T-lymphocyte (CTL) epitopes compared to other parts of the HIV proteome (Novitsky et al., J. Virol. 2002 76(20):10155-10168), which make it more effective in inducing a broad immune response when used as a vaccine candidate. It has also been shown that the risk of AIDS is greatly increased in individuals with falling titres of p24 antibodies. This suggests that high anti-p24 antibody titres might be necessary to maintain a disease-free state.

In addition, HIV-1 Pr55$^{gag}$ VLPs are safe, easy to produce and have the potential of including chimeric immunogens [Doan et al., 2005 Rev Med. Virol. 15(2):75-88; Halsey et al., 2008 Virus Res. 2008 133(2):259-268. Epub 2008 Mar. 10]. Their particulate nature and size, which approximates that of HIV-1, make HIV-1 Pr55$^{gag}$ VLPs more likely to stimulate the immune system better than non-particulate immunogens.

As above, the p24 protein forms the outer capsid layer of the viral particle. This protein has a high density of cytotoxic T-lymphocyte (CTL) epitopes compared to other parts of the HIV proteome (Novitsky et al., J. Virol. 2002 76(20):10155-10168), which make it more effective in inducing a broad immune response when used as a vaccine candidate. It has also been shown that the risk of AIDS is greatly increased in individuals with falling titres of p24 antibodies. This suggests that high anti-p24 antibody titres might be necessary to maintain a disease-free state.

The matrix protein, p17, facilitates the intra-membrane associations that are required for viral assembly and release (Dorfman et al., 1994 J Virol 68(12):8180-8187]. Protein p17 is also involved in the transport of the viral pre-integration complex into the nucleus (Burkinsky et al., 1993). Fused together with p24, this p17/p24 (p41) complex contains the highest density of CTL epitopes in the HIV-1 genome (Novitsky et al., J. Virol. 2002 76(20):10155-10168).

HIV-1 reverse transcriptase (RT) is an RNA-dependent DNA polymerase that makes DNA templates and synthesises DNA from RNA. It is essential for viral replication. HIV-1 RT is cleaved from the Pr160$^{gag-pol}$ polyprotein by the HIV-1 protease (PR). Several CTL epitopes against HIV-1 have been identified in RT, although they appear to be subdominant to Gag-specific epitopes [Dela Cruz et al., 2000 Int Immunol 12(9):1293-1302].

Several studies have indicated that enhanced immune responses can be achieved by heterologous prime-boost inoculation regimens. It has been shown that a HIV-1 DNA vaccine denominated pTHGagC used as a prime inoculation of mice is boosted effectively by Pr55$^{Gag}$ virus-like particles (VLPs) (Chege et al., J. Gen. Virol. 2008 89:2214-2227). Because p24 has the highest density of cytotoxic T-lymphocyte (CTL) epitopes compared to other parts of the HIV proteome it was thought that the particulate nature of protein bodies containing p24 may have a similar boosting effect to expand immune responses after the immune system has been primed. It has also been thought that the use of combinations of protein bodies containing different HIV-1 antigens such as p41 and RT, may broaden the immune response such as has been shown in the use of the multigene DNA vaccine "grttn" (Burgers et al., AIDS Research and Human Retroviruses 2008 24(2):195-206) that contains five AIDS genes, the gag, reverse transcriptase, tat and nef genes that are expressed as a polyprotein and a truncated env gene (gp150).

BRIEF SUMMARY OF THE INVENTION

The present invention contemplates an immunogen-specific adjuvant for a vaccine or inoculum. The adjuvant is comprised of particulate recombinant protein body-like assemblies (RPBLAs) that contain a recombinant fusion protein. The recombinant fusion protein contains two sequences peptide-linked together in which one sequence is a protein body-inducing sequence (PBIS) such as a prolamin sequence and the other is a T-cell stimulating immunogenic polypeptide whose sequence is that of a pathogenic polypeptide sequence present in or induced by a vaccine or inoculum. The adjuvant when used in an inoculum without a prior priming vaccination or inoculation does not induce production of antibodies or T cell activation to the pathogenic sequence. A contemplated adjuvant is typically used in an adjuvant-effective amount dissolved or dispersed in a pharmaceutically acceptable diluent.

BRIEF DESCRIPTION OF THE DRAWINGS

In the drawings forming a part of this disclosure,

FIG. 10 in two parts as FIG. 10A and FIG. 10B illustrate growth of C3 tumors in C57BL/6 mice after immunization with: (i) 100 μg empty plasmid (pTHamp), (ii) 100 μg plasmid expressing E7SH (pTHamp-E7SH), (iii) 5 μg of RPBLAs containing RX3-Gfp fusion protein (RX3-Gfp), (iv) 5 μg of RPBLAs containing RX3-E7SH fusion protein (RX3-E7SH) or (v) 5 μg of RPBLAs containing RX3-E7SH fusion protein and 100 μl of IFA (RX3-E7SH/IFA). Data shown provide the surface area tumor size from days 0 to 14. FIG. 10A illustrates a comparison of DNA vs RPBLAs immunization effect on tumor regression, whereas

DEFINITIONS

Figure 1A:
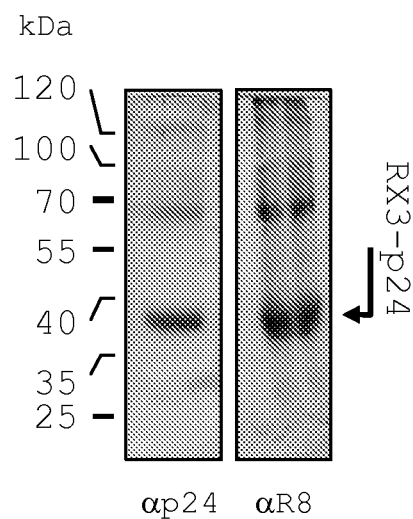
FIG. 1 in three panels (FIG. 1A, FIG. 1B and FIG. 1C) shows the analysis by western blot of RPBLA fractions isolated from tobacco plants agroinfiltrated with RX3-p24, RX3-p41 and RX3-RT. The presence of full length RX3 fusion proteins in the corresponding RPBLA fraction preparation was checked by using the following antibodies: (i) αR8 which recognizes RX3, (ii) αp24 which recognizes p41 and p24 antigens and (iii) αRT which recognizes RT antigen.

The word "antigen" has been used historically to designate an entity that is bound by an antibody or receptor, and also to designate the entity that induces the production of the antibody or cellular response such as that of a CD4+ T cell. More current usage limits the meaning of antigen to that entity bound by an antibody or receptor, whereas the word "immunogen" is used for the entity that induces antibody production or cellular response. Where an entity discussed herein is both immunogenic and antigenic, reference to it as either an immunogen or antigen is typically made according to its intended utility.

"Antigenic determinant" refers to the actual structural portion of the antigen that is immunologically bound by an antibody combining site or T-cell receptor. The term is also used interchangeably with "epitope".

As used herein, the term "fusion protein" designates a polypeptide that contains at least two amino acid residue sequences not normally found linked together in nature that are operatively linked together end-to-end (head-to-tail) by a peptide bond between their respective carboxy- and amino-terminal amino acid residues. A fusion protein of the present invention is a chimer of a protein body-inducing sequence (PBIS) linked to a second sequence that is a T-cell stimulating polypeptide (e.g., peptide or protein) that is present in the pathogen (target) at which the vaccine or inoculum is directed.

The term "immunogen-specific" is used herein to distinguish the adjuvanticity of a contemplated recombinant adjuvant and a more general adjuvant. More particularly, a contemplated immunogen-specific adjuvant enhances the cellular (T-cell) immune response toward an immunogen that includes an amino acid residue sequence of the adjuvant and does not generally activate the immune system. Thus, the vaccine or inoculum shares an amino acid residue sequence or encodes a shared sequence with the adjuvant.

An "inoculum" is a composition that comprises an immunogenically effective amount of immunogenic chimer particles dissolved or dispersed in a pharmaceutically acceptable diluent composition that typically also contains water. When administered to a host animal in need of immunization or in which antibodies or activated T cells are desired to be induced such as a mammal (e.g., a mouse, dog, goat, sheep, horse, bovine, monkey, ape, or human) or bird (e.g., a chicken, turkey, duck or goose), an inoculum induces a B cell and/or T cell response (stimulation) in an inoculated host animal such as production of antibodies that immunoreact with the immunogen of the chimer and/or induces T cells that respond to the immunogen. A "vaccine" is a type of inoculum in which the vaccine-induced antibodies not only immunoreact with the immunogen or activated T cells respond to that immunogen, but also immunoreact with the pathogen from which the immunogen is derived in vivo, and provide protection from that disease state.

The expression "T-Cell-mediated immunity" refers to an immune response that does not involve antibodies or complement but rather involves the activation of macrophages, natural killer cells (NK), antigen-specific cytotoxic T-lymphocytes, and the release of various cytokines in response to an antigen. Historically, the immune system was separated into two branches: humoral immunity, for which the protective function of immunization could be found in the humor (cell-free bodily fluid or serum) and cellular immunity, for which the protective function of immunization was associated with cells. CD4 cells or helper T cells provide protection against different pathogens. T-Cell-mediated immunity is an immune response produced when T cells, especially cytotoxic T cells, that are sensitized to foreign antigens attack and lyse target cells. In addition to direct cytotoxicity, T cells can stimulate the production of lymphokines that activate macrophages. Cell-mediated immune responses are important in defense against pathogens, autoimmune diseases, some acquired allergies, viral infection, some tumors and other immune reactions.

DETAILED DESCRIPTION OF PREFERRED EMBODIMENTS

The present invention contemplates an immunogen-specific adjuvant for a vaccine or inoculum. The adjuvant is comprised of particulate recombinant protein body-like assemblies (RPBLAs) that contain a recombinant fusion protein. The recombinant fusion protein contains two sequences peptide-linked together in which one sequence is a protein body-inducing sequence (PBIS) such as a preferred prolamin sequence and the other is a T-cell stimulating immunogenic polypeptide whose sequence (a) is present in a pathogenic polypeptide sequence present in a polypeptide-containing vaccine or inoculum or (b) is encoded by a nucleic acid vaccine or inoculum. The adjuvant, at the concentration used in an inoculum in a host animal without a prior priming by vaccination or inoculation of a host animal or additional immunogen, does not induce production of antibodies in that host animal that immunoreact with or induce T cell activation to the pathogenic sequence.

The invention also contemplates a method for inducing an T-cell mediated immune response in a subject in need thereof against an immunogenic peptide which comprises the administration to a subject in need thereof of a vaccine selected from the group of
(i) a particulate recombinant protein body-like assemblies (RPBLAs) that contain a recombinant fusion protein, said recombinant fusion protein containing two portions peptide-linked together in which a first portion is a protein body-inducing sequence (PBIS) and a second portion is a immunogenic polypeptide and
(ii) a nucleic acid molecule that encodes a fusion protein, said recombinant fusion protein containing two portions peptide-linked together in which a first portion is a protein body-inducing sequence (PBIS) and a second portion is a immunogenic polypeptide.

In a preferred embodiment, the method of the invention is carried out using a RPBLA wherein the PBIS forming part of the first portion includes a prolamin sequence. In a still more preferred embodiment, the prolamin sequence is present in a prolamin selected from the group consisting of gamma-zein, alpha-zein, delta-zein, beta-zein, rice prolamin and gamma-gliadin.

In a preferred embodiment, the PBIS sequence further includes a signal peptide sequence that directs a protein towards the endoplasmic reticulum (ER) of the RPBLA-expressing cell.

In a preferred embodiment, the immunogenic peptide used in fusion protein forming the RPBLA is a peptide capable of stimulating the T-cell immune response.

In another preferred embodiment, the method of the invention is carried out using a RPBLA comprising a second portion wherein the immunogenic polypeptide sequence is selected from the group of
(i) a polypeptide encoded by the HPV E7 gene,
(ii) a polypeptide encoded by the HIV-1 gag gene and
(iii) a polypeptide encoded by the HIV-1 pol gene In a preferred embodiment, the method of the invention is carried out using a particulate recombinant protein body-like assemblies (RPBLAs) are assembled in vitro from the purified recombinant fusion protein.

In a more preferred embodiment, the administration step of the method of the invention is preceded by a priming vaccination or inoculation step using a composition comprising immunogenic polypeptide or a nucleic acid encoding said immunogenic polypeptide.

In a still more preferred embodiment, the composition comprising the immunogenic polypeptide used in the priming vaccination or stimulation step is selected from the group of
(i) a particulate recombinant protein body-like assemblies (RPBLAs) that contain a recombinant fusion protein, said recombinant fusion protein containing two portions peptide-linked together in which a first portion is a protein body-inducing sequence (PBIS) and a second portion is the T-cell stimulating immunogenic polypeptide,
(ii) a nucleic acid molecule that encodes the immunogenic polypeptide and
(iii) a nucleic acid molecule that encodes a fusion protein, said recombinant fusion protein containing two portions peptide-linked together in which a first portion is a protein body-inducing sequence (PBIS) and a second portion is the immunogenic polypeptide.

In a preferred embodiment, the immunogenic peptide used in fusion protein forming the RPBLA is a peptide capable of stimulating the T-cell immune response.

In a more preferred embodiment, the vaccine is administered intramuscularly.

In another aspect, the invention relates to vaccine for use in a method for inducing an T-cell mediated immune response in a subject in need thereof against an immunogenic peptide wherein the vaccine is selected from the group of
(i) a particulate recombinant protein body-like assemblies (RPBLAs) that contain a recombinant fusion protein, said recombinant fusion protein containing two portions peptide-linked together in which a first portion is a protein body-inducing sequence (PBIS) and a second portion is a immunogenic polypeptide and
(ii) a nucleic acid molecule that encodes a fusion protein, said recombinant fusion protein containing two portions peptide-linked together in which a first portion is a protein body-inducing sequence (PBIS) and a second portion is a immunogenic polypeptide.

A contemplated adjuvant can be administered along with or separately as a boost to an anti-pathogen vaccine or inoculum. Such a vaccine or inoculum can contain an attenuated live or killed pathogen such as a bacterium or virus, a subunit vaccine or inoculum that contains only a protein portion of a pathogen, or a vaccine or inoculum that contains an immunogen that is comprised of a polypeptide linked to a carrier, wherein the immunogenic portion of the vaccine or inoculum contains a polypeptide sequence that is also present in the adjuvant. Where the vaccine or inoculum is a nucleic acid preparation such as a DNA or RNA vaccine, the nucleic acid encodes an immunogenic amino acid sequence that is also present in the adjuvant. Nucleic acid vaccines and inocula are themselves well known.

A contemplated adjuvant can be administered as a preparation of expressed RPBLAs, or as a nucleic acid preparation, such as a single or double stranded DNA sequence, that encodes the RPBLAs. In the latter circumstance, the RPBLAs are expressed in vivo in the host animal. In either situation, media in which the expressed RPBLAs or nucleic acids are dissolved or dispersed to form adjuvant compositions are also well known.

Illustrative nucleic acid sequences are provided hereinafter that encode specific portions of the RPBLAs. As is well known in the art, particular codons are preferred for encoding amino acid residues in different animals, and as a consequence the skilled worker can revise specific nucleic acid sequences to provide desired degrees of expression. In addition, several vectors are well known for expressing foreign nucleic acids and their encoded proteins in animal hosts, including humans. On expression, the polypeptides encoded self-assemble in vivo to form RPBLAs.

T-cell stimulating immunogenic polypeptide portions of a number of illustrative adjuvants are discussed hereinafter that relate to the HIV-1 virus. In those adjuvants, a DNA vaccine that comprises all of parts of the gag gene is utilized. The HIV-1 gag gene encodes four proteins: the P24 capsid (CA), P17 matrix (MA), and two nucleocapsid proteins (NC) P6 and P9. Illustrative adjuvants' fusion proteins contain the gag-encoded P24 sequence or the P41 sequence that results from fusion of the P24 and P17 sequences, and the reverse transcriptase (RT) that is encoded by the HIV-1 pol gene.

Analogously, a vaccine or inoculum against hepatitis B virus (HBV) the utilizes one or more of the surface (HBsAg) proteins as immunogen can utilize an adjuvant whose T-cell stimulating immunogenic polypeptide portion includes a sequence illustrated of a surface protein that includes a PreS1 and/or PreS2 portions of the surface protein in the table of T Cell Epitopes that follows. One such vaccine is that sold under the name RECOMBIVAX HB® hepatitis B vaccine that is a non-infectious subunit viral vaccine derived from the hepatitis B surface antigen (HBsAg) produced in yeast cells and developed in the Merck Research Laboratories. Similarly, the HBV core-based vaccine of U.S. Pat. No. 7,351,413, can be provided an adjuvant by utilization of one or more core sequences set out in the table of T Cell Epitopes that follows. Additional adjuvants can be prepared as discussed herein using the sequences in that following table or other T cell epitopes obtained from the literature.

A contemplated adjuvant is typically used in an adjuvant-effective amount dissolved or dispersed in a pharmaceutically acceptable diluent as an adjuvant composition. The amount utilized can vary widely in different host animals, with the T-cell stimulating immunogenic polypeptide portion used, and the construct used. Typical amounts are about 1 microgram (μg) of RPBLAs per kilogram (kg) of host body weight (μg/kg) to about 1 milligram (mg) of RPBLAs per kilogram of host body weight (mg/kg). More usual amounts are about 5 μg/kg of host body weight to about 0.5 mg/kg host body weight.

The diluent is typically aqueous-based and can include one or more additional adjuvants, buffers, salts and viscosity enhancing agents. The ingredients of the diluent are those materials that are often present in a vaccine or inoculum as are discussed hereinafter.

Protein Bodies and Protein Body-Inducing Sequences

Inasmuch as protein bodies (PBs) are appropriately so-named only in seeds, similar structures produced in other plant organs and in non-higher plants are referred to generally as synthetic PBs or "recombinant protein body-like assemblies" (RPBLAs). Such RPBLAs are membrane-enclosed fusion proteins that are found associated with the endoplasmic reticulum (ER) of a cell.

"Purified RPBLAs" are membrane free preparations of RPBLAs in which the membrane has been removed, usually by chemical reduction as with a mercaptan-containing reagent, and the fusion protein purified as by chromatographic means to free the fusion protein from the membrane and other expression-associated impurities. The resulting purified protein is then reassembled in vitro to form purified RPBLA particles. That reformation of particles typically takes place in an aqueous composition in the presence of salts and an oxidizing environment. The formation of such purified RPBLAs is illustrated hereinafter.

A contemplated RPBLA is a recombinantly prepared fusion protein (polypeptide) that is expressed in a cell foreign to the nucleic acids used to transform the cell. The cell(s) in which the polypeptide is expressed is a host cell(s), and can be a cell preparation or cells of an intact organism. The intact organism can itself be a group of single celled organisms such as bacteria or fungi, or multi-celled plants or animals, including humans. When a human is the host, the person is the recipient of a nucleic acid-encoded form of the adjuvant and the adjuvant is administered as part of a treatment regimen.

In living organisms, the amino acid residue sequence of a protein or polypeptide is directly related via the genetic code to the deoxyribonucleic acid (DNA) sequence of the gene that codes for the protein. Thus, through the well-known degeneracy of the genetic code additional DNAs and corresponding RNA sequences (nucleic acids) can be prepared as desired that encode the same fusion protein amino acid residue sequences, but are sufficiently different from a before-discussed gene sequence that the two sequences do not hybridize at high stringency, but do hybridize at moderate stringency.

High stringency conditions can be defined as comprising hybridization at a temperature of about 50°-55° C. in 6×SSC and a final wash at a temperature of 68° C. in 1-3×SSC. Moderate stringency conditions comprise hybridization at a temperature of about 50° C. to about 65° C. in 0.2 to 0.3 M NaCl, followed by washing at about 50° C. to about 55° C. in 0.2×SSC, 0.1% SDS (sodium dodecyl sulfate).

A nucleic sequence (DNA sequence or an RNA sequence) that (1) itself encodes, or its complement encodes, a fusion protein containing a protein body-inducing sequence (PBIS) and a polypeptide of interest is also contemplated herein. As is well-known, a nucleic acid sequence such as a contemplated nucleic acid sequence is expressed when operatively linked to an appropriate promoter in an appropriate expression system as discussed elsewhere herein.

Different hosts often have preferences for a particular codon to be used for encoding a particular amino acid residue. Such codon preferences are well known and a DNA sequence encoding a desired fusion protein sequence can be altered, using in vitro mutagenesis for example, so that host-preferred codons are utilized for a particular host in which the fusion protein is to be expressed.

The RPBLAs are usually present in a generally spherical form having a diameter of about 0.5 to about 3 microns (µ) and usually about 1µ. In some instances, RPBLAs are amorphous in shape and can vary widely in dimensions, but are still found associated with the ER.

The density of RPBLAs is typically greater than that of substantially all of the endogenous host cell proteins, and is typically about 1.1 to about 1.35 g/ml. The high density of contemplated RPBLAs is due to the general ability of the recombinant fusion proteins to assemble as multimers and accumulate.

A contemplated RPBLA used as an adjuvant need not be expressed in a plant. Rather, as disclosed in published US application 20060121573, RPBLAs can be expressed in other transformed eukaryotes, particularly in transformed mammalian cells.

A fusion protein of the adjuvant RPBLAs contains two proteinaceous sequences linked together by a peptide bond as is found in a naturally occurring protein or in a polypeptide expressed by a genetically engineered nucleic acid. In a contemplated fusion protein, one sequence is a protein body-inducing sequence (PBIS) such as that of a prolamin, and the other is a biologically active immunogenic polypeptide. Either of the two portions can be at the N-terminus of the fusion protein. However, it is preferred to have the PBIS at the N-terminus.

A contemplated protein body-inducing sequence (PBIS) is preferably in whole or part from a higher plant. Illustrative, non-limiting examples of PBIS include storage proteins or modified storage proteins, as for instance, prolamins or modified prolamins, prolamin domains or modified prolamin domains. Prolamins are reviewed in Shewry et al., 2002 J. Exp. Bot. 53(370):947-958. A preferred PBIS sequence is present in a prolamin compound sequence such as gamma-zein, alpha-zein, delta-zein, beta-zein, rice prolamin and gamma-gliadin that are discussed hereinafter.

A PBIS includes a sequence that directs a protein towards the endoplasmic reticulum (ER) of the RPBLA-expressing cell. That sequence often referred to as a leader sequence or signal peptide can be from the same plant as the remainder of the PBIS or from a different plant or an animal or fungus. Illustrative signal peptides are the 19 residue gamma-zein signal peptide sequence shown in WO 2004003207 (US 20040005660), the 19 residue signal peptide sequence of alpha-gliadin or 21 residue gamma-gliadin signal peptide sequence (see, Altschuler et al., 1993 Plant Cell 5:443-450; Sugiyama et al., 1986 Plant Sci. 44:205-209; and Rafalski et al., 1984 EMBO J. 3(6):1409-11415 and the citations therein). The pathogenesis-related protein of PR10 class includes a 25 residue signal peptide sequence that is also useful herein. Similarly functioning signal peptides from other plants and animals are also reported in the literature.

The characteristics of the signal peptides responsible for directing the protein to the ER have been extensively studied (von Heijne et al., 2001 Biochim. Biophys. Acta December 12 1541(1-2):114-119). The signal peptides do not share homology at a primary structure, but have a common tripartite structure: a central hydrophobic h-region and hydrophilic N- and C-terminal flanking regions. These similarities, and the fact that proteins are translocated through the ER membrane using apparently common pathways, permits interchange of the signal peptides between different proteins or even from different organisms belonging to different phyla (See, Martoglio et al., 1998 Trends Cell Biol. October; 8(10):410-415). Thus, a PBIS can include a signal peptide of a protein from a phylum different from higher plants.

It is to be understood that an entire prolamin sequence is not required to be used. Rather, as is discussed hereinafter, only portions are needed although an entire prolamin sequence can be used.

Gamma-Zein, a maize storage protein whose DNA and amino acid residue sequences are shown hereinafter, is one of the four maize prolamins and represents 10-15 percent of the total protein in the maize endosperm. As other cereal prolamins, alpha- and gamma-zeins are biosynthesized in membrane-bound polysomes at the cytoplasmic side of the rough ER, assembled within the lumen and then sequestered into ER-derived protein bodies (Herman et al., 1999 Plant Cell 11:601-613; Ludevid et al., 1984 Plant Mol. Biol. 3:277-234; Torrent et al., 1986 Plant Mol. Biol. 7:93-403).

Gamma-Zein is composed of four characteristic domains: i) a peptide signal of 19 amino acids, ii) the repeat domain containing eight units of the hexapeptide PPPVHL (SEQ ID NO:2) [(53 amino acid residues (aa)], iii) the ProX domain where proline residues alternate with other amino acids (29 aa) and iv) the hydrophobic cysteine rich C-terminal domain (111 aa).

The ability of gamma-zein to assemble in ER-derived RPBLAs is not restricted to seeds. In fact, when gamma-zein-gene was constitutively expressed in transgenic Arabidopsis plants, the storage protein accumulated within ER-derived PBLS in leaf mesophyl cells (Geli et al., 1994 Plant Cell 6:1911-1922). Looking for a signal responsible for the gamma-zein deposition into the ER-derived protein bodies (prolamins do not have KDEL signal for ER-retention), it has been demonstrated that the proline-rich N-terminal domain including the tandem repeat domain was necessary for ER retention. In this work, it was also suggested that the C-terminal domain could be involved in protein body formation, however, recent data (WO2004003207A1) demonstrate that the proline-rich N-terminal domain is necessary and sufficient to retain in the ER and to induce the protein body formation. However, the mechanisms by which these domains promote the protein body assembly are still unknown, but evidence from in vitro studies suggests that the N-terminal portion of gamma-zein is able to self-assemble into ordered structures.

It is preferred that a gamma-zein-based PBIS include at least one repeat and the amino-terminal nine residues of the ProX domain, and more preferably the entire Pro-X domain. The C-terminal portion of gamma-zein is not needed, but can be present. Those sequences are shown in US 20040005660 and designated as RX3 and P4, respectively, and are noted hereinafter.

Zeins are of four distinct types: alpha, beta, delta, and gamma. They accumulate in a sequential manner in the ER-derived protein bodies during endosperm development. Beta-zein and delta-zein do not accumulate in large amount in maize PBs, but they were stable in the vegetative tissues and were deposited in ER-derived protein body-like structures when expressed in tobacco plants (Bagga et al., 1997 *Plant Cell* September 9(9):1683-1696). This result indicates that beta-zein, as well as delta-zein, can induce ER retention and PB formation.

The wheat prolamin storage proteins, gliadins, are a group of K/HDEL-less proteins whose transport via the ER appears to be complex. These proteins sequester in to the ER where they are either retained and packaged into dense protein bodies, or are transported from the ER via the Golgi into vacuoles. (Altschuler et al., 1993 *Plant Cell* 5:443-450.)

The gliadins appear to be natural chimeras, containing two separately folded autonomous regions. The N-terminus is composed of about 7 to about 16 tandem repeats rich in glutamine and proline. The sequence of the tandem repeats varies among the different gliadins, but are based on one or the other consensus sequences PQQPFPQ (SEQ ID NO:3), PQQQPPFS (SEQ ID NO:4) and PQQPQ (SEQ ID NO:5). The C-terminal region of the protein contains six to eight cysteines that form intramolecular disulfide bonds. The work of the Altschuler et al. indicates that the N-terminal region and consensus sequences are responsible for PB formation in the ER from gamma-gliadin. (Altschuler et al., 1993 *Plant Cell* 5:443-450.)

Illustrative useful prolamin-type sequences are shown in the Table below along with their GenBank identifiers.

| PROTEIN NAME | GENBANK ID |
|---|---|
| α-Zein (22 kD) | M86591 |
| Albumin (32 kD) | X70153 |
| γ-Zein (27 kD) | X53514 |
| γ-Zein (50 kD) | AF371263 |
| δ-Zein (18 kD) | AF371265 |
| 7S Globulin or Vicilin type | NM_113163 |
| 11S Globulin or Legumin type | DQ256294 |
| Prolamin 13 kD | AB016504 |
| Prolamin 16 kD | AY427574 |
| Prolamin 10 kD | AF294580 |
| γ-Gliadin | M36999 |
| γ-Gliadin precursor | AAA34272 |

Further useful sequences are obtained by carrying out a BLAST search in the all non-redundant GenBank CDS translations+PDB+SwissProt+PIR+PRF (excluding environmental samples) data base as described in Altschul et al., 1997 *Nucleic Acids Res.* 25:3389-3402 using a query such as those shown below:

RX3 Query

SEQ ID NO: 6
PPPPVHLPPPVHLPPPVHLPPPVHLPPPVHLPPPVHLPPPVHVPPPVHL
PPPP

Alpha-Zein

SEQ ID NO: 7
QQQQQFLPALSQLDVVNPVAYLQQQLLASNPLALANVAAYQQQQQLQQF

LPALSQLAMVNPAAYL

Rice Prolamin Query

SEQ ID NO: 8
QQVLSPYNEFVRQQYGIAASPFLQSATFQLRNNQVWQQLALVAQQSHCQ

DINIVQAIAQQLQLQQFGDLY

An illustrative modified prolamin includes (a) a signal peptide sequence, (b) a sequence of one or more copies of the repeat domain hexapeptide PPPVHL (SEQ ID NO: 2) of the protein gamma-zein, the entire domain containing eight hexapeptide units; and (c) a sequence of all or part of the ProX domain of gamma-zein. Illustrative specific modified prolamins include the polypeptides identified below as R3, RX3 and P4 whose DNA and amino acid residue sequences are also shown below.

Particularly preferred prolamins include gamma-zein and its component portions as disclosed in published application WO2004003207, the rice rP13 protein and the 22 kDa maize alpha-zein and its N-terminal fragment. The DNA and amino acid residue sequences of the gamma-zein, rice and alpha-zein proteins are shown below.

Gamma-Zein of 27 kD

DNA Sequence:

SEQ ID NO: 9
```
atgagggtgt tgctcgttgc cctcgctctc ctggctctcg    40
ctgcgagcgc cacctccacg catacaagcg gcggctgcgg    80
ctgccagcca ccgccgccgg ttcatctacc gccgccggtg   120
catctgccac ctccggttca cctgccacct ccggtgcatc   160
tcccaccgcc ggtccacctg ccgccgccgg tccacctgcc   200
accgccggtc catgtgccgc cgccggttca tctgccgccg   240
ccaccatgcc actaccctac tcaaccgccc cggcctcagc   280
ctcatcccca gccacaccca tgcccgtgcc aacagccgca   320
tccaagcccg tgccagctgc agggaacctg cggcgttggc   360
agcacccccga tcctgggcca gtgcgtcgag tttctgaggc   400
atcagtgcag cccgacggcg acgccctact gctcgcctca   440
gtgccagtcg ttgcggcagc agtgttgcca gcagctcagg   480
caggtggagc cgcagcaccg gtaccaggcg atcttcggct   520
tggtcctcca gtccatcctg cagcagcagc cgcaaagcgg   560
ccaggtcgcg gggctgttgg cggcgcagat agcgcagcaa   600
ctgacggcga tgtgcggcct gcagcagccg actccatgcc   640
cctacgctgc tgccggcggt gtccccacg cc             672
```

Protein Sequence:

SEQ ID NO: 10

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val His Leu Pro Pro Val His Leu Pro Pro Val His Leu
        35                  40                  45

Pro Pro Pro Val His Leu Pro Pro Val His Leu Pro Pro Val
    50                  55                  60

His Leu Pro Pro Val His Val Pro Pro Val His Leu Pro Pro
65                  70                  75              80

Pro Pro Cys His Tyr Pro Thr Gln Pro Pro Arg Pro Gln Pro His Pro
                85                  90                  95

Gln Pro His Pro Cys Pro Cys Gln Gln Pro His Pro Ser Pro Cys Gln
                100                 105                 110

Leu Gln Gly Thr Cys Gly Val Gly Ser Thr Pro Ile Leu Gly Gln Cys
                115                 120                 125

Val Glu Phe Leu Arg His Gln Cys Ser Pro Thr Ala Thr Pro Tyr Cys
130                 135                 140

Ser Pro Gln Cys Gln Ser Leu Arg Gln Cys Cys Gln Gln Leu Arg
145                 150                 155                 160

Gln Val Glu Pro Gln His Arg Tyr Gln Ala Ile Phe Gly Leu Val Leu
                165                 170                 175

Gln Ser Ile Leu Gln Gln Pro Gln Ser Gly Gln Val Ala Gly Leu
                180                 185                 190

Leu Ala Ala Gln Ile Ala Gln Gln Leu Thr Ala Met Cys Gly Leu Gln
                195                 200                 205

Gln Pro Thr Pro Cys Pro Tyr Ala Ala Ala Gly Gly Val Pro His Ala
210                 215                 220

RX3

DNA Sequence:

SEQ ID NO: 11
atgagggtgt tgctcgttgc cctcgctctc ctggctctcg        40
ctgcgagcgc cacctccacg catacaagcg gcggctgcgg        80
ctgccagcca ccgccgccgg ttcatctacc gccgccggtg       120
catctgccac ctccggttca cctgccacct ccggtgcatc       160
tcccaccgcc ggtccacctg ccgccgccgg tccacctgcc       200
accgccggtc catgtgccgc cgccggttca tctgccgccg       240
ccaccatgcc actacccta ctcaaccgccc cggcctcagc       280
ctcatcccca gccacaccca tgcccgtgcc aacagccgca       320
tccaagcccg tgccagacc                              339

Protein Sequence:

SEQ ID NO: 12
Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val His Leu Pro Pro Val His Leu Pro Pro Val His Leu
        35                          40                  45

Pro Pro Pro Val His Leu Pro Pro Val His Leu Pro Pro Val
    50                  55                          60

His Leu Pro ProPro Val His Val Pro Pro Val His Leu Pro Pro
65                  70                  75                  80

Pro Pro Cys His Tyr Pro Thr Gln Pro Pro Arg Pro Gln Pro His Pro
                85                  90                  95

R3
DNA Sequence:

SEQ ID NO: 13
```
atgagggtgt tgctcgttgc cctcgctctc ctggctctcg   40
ctgcgagcgc cacctccacg catacaagcg gcggctgcgg   80
ctgccagcca ccgccgccgg ttcatctacc gccgccggtg  120
catctgccac ctccggttca cctgccacct ccggtgcatc  160
tcccaccgcc ggtccacctg ccgccgccgg tccacctgcc  200
accgccggtc catgtgccgc cgccggttca tctgccgccg  240
```
Protein Sequence:

SEQ ID NO: 14
```
Met Arg Val Leu Leu Val Ala Leu Ala Leu Leu Ala Leu Ala Ala Ser
 1               5                  10                  15
Ala Thr Ser Thr His Thr Ser Gly Gly Cys Gly Cys Gln Pro Pro
                20                  25                  30
Pro Val His Leu Pro Pro Pro Val His Leu Pro Pro Pro Val His Leu
            35                  40                  45
Pro Pro Pro Val His Leu Pro Pro Pro Val His Leu Pro Pro Pro Val
         50                  55                  60
His Leu Pro Pro Pro Val His Val Pro Pro Pro Val His Leu Pro Pro
 65                  70                  75                  80
Pro Pro Cys His Tyr Pro Thr Gln Pro Pro Arg Tyr
                 85                  90
```

P4
DNA Sequence:

SEQ ID NO: 15
```
atgagggtgt tgctcgttgc cctcgctctc ctggctctcg   40
ctgcgagcgc cacctccacg catacaagcg gcggctgcgg   80
ctgccagcca ccgccgccgg ttcatctgcc gccgccacca  120
tgccactacc ctacacaacc gccccggcct cagcctcatc  160
cccagccaca cccatgcccg tgccaacagc cgcatccaag  200
cccgtgccag acc                              213
```
Protein Sequence:

SEQ ID NO: 16
```
Met Arg Val Leu Leu Val Ala Leu Ala Leu Leu Ala Leu Ala Ala Ser
1                5                  10                  15
Ala Thr Ser Thr His Thr Ser Gly Gly Cys Gly Cys Gln Pro Pro
                20                  25                  30
Pro Val His Leu Pro Pro Pro Cys His Tyr Pro Thr Gln Pro Pro
            35                  40                  45
Arg Pro Gln Pro His Pro Gln Pro His Pro Cys Pro Cys Gln Pro
         50                  55                  60
His Pro Ser Pro Cys Gln Tyr
65                  70
```

-continued
```
Gln Pro His Pro Cys Pro Cys Gln Gln Pro His Pro Ser Pro Cys Gln
                100                 105                 110
Tyr
```

X10
DNA Sequence:

SEQ ID NO: 17
```
atgagggtgt tgctcgttgc cctcgctctc ctggctctcg   40
ctgcgagcgc cacctccacg catacaagcg gcggctgcgg   80
ctgccaatgc cactacccta ctcaaccgcc ccggcctcag  120
cctcatcccc agccacaccc atgcccgtgc caacagccgc  160
atccaagccc gtgccagacc                        180
```

Protein Sequence:

SEQ ID NO: 18
Met Arg Val Leu Leu Val Ala Leu Ala Leu Leu Ala Leu Ala Ala Ser
 1               5                  10                  15

Ala Thr Ser Thr His Thr Ser Gly Gly Cys Gly Cys Gln Cys His Tyr
         20                  25                  30

Pro Thr Gln Pro Pro Arg Pro Gln Pro His Pro Gln Pro His Pro Cys
             35                  40                  45

Pro Cys Gln Gln Pro His Pro Ser Pro Cys Gln Tyr
     50                  55                  60 rP13—rice prolamin of 13 kD homologous to the clone—AB016504 Sha et al., 1996 Biosci. Biotechnol. Biochem. 60(2):335-337; Wen et al., 1993 Plant Physiol. 101(3):1115-1116; Kawagoe et al., 2005 Plant Cell 17(4):1141-1153; Mullins et al., 2004 J. Agric. Food Chem. 52(8):2242-2246; Mitsukawa et al., 1999 Biosci. Biotechnol. Biochem. 63(11): 1851-1858
Protein Sequence:

SEQ ID NO: 19
MKIIFVFALLAIAACSASAQFDVLGQSYRQYQLQSPVLLQQQVLSPYNEF

VRQQYGIAASPFLQSATFQLRNNQVWQQLALVAQQSHCQDINIVQAIAQQ

LQLQQFGDLYFDRNLAQAQALLAFNVPSRYGIYPRYYGAPSTITTLGGVL

DNA Sequence:

SEQ ID NO: 20
atgaagatcatttttcgtctttgctctccttgctattgctgcatgcagcg cctctgcgcagtttgatgttttaggtcaaagttataggcaatatcagct gcagtcgcctgtcctgctacagcaacaggtgcttagcccatataatgag ttcgtaaggcagcagtatggcatagcggcaagcccttcttgcaatcag ctacgtttcaactgagaaacaaccaagtctggcaacagctcgcgctggt ggcgcaacaatctcactgtcaggacattaacattgttcaggccatagcg cagcagctacaactccagcagtttggtgatctctactttgatcggaatc tggctcaagctcaagctctgttggcttttaacgtgccatctagatatgg tatctaccctaggtactatggtgcacccagtaccattaccacccttggc ggtgtcttg 22aZt N-terminal fragment of the maize alpha-zein of 22 kD—V01475 Kim et al., 2002 Plant Cell 14(3):655-672; Woo et al., 2001 Plant Cell 13(10):2297-2317; Matsushima et al., 1997 Biochim. Biophys. Acta 1339(1):14-22; Thompson et al., 1992 Plant Mol. Biol. 18(4):827-833.
Protein Sequence (Full Length):

SEQ ID NO: 21
MATKILALLALLALFVSATNAFIIPQCSLAPSAIIPQFLPPVTSMGFEHL

AVQAYRLQQALAASVLQQPINQLQQQSLAHLTIQTIATQQQQQFLPALSQ

LDVVNPVAYLQQQLLASNPLALANVAAYQQQQQLQQFLPALSQL

DNA Sequence (Full Length):

SEQ ID NO: 22
atggctaccaagatattagccctccttgcgcttcttgcccttttttgtgag cgcaacaaatgcgttcattattccacaatgctcacttgctcctagtgcca -continued ttataccacagttcctcccaccagttacttcaatgggcttcgaacaccta gctgtgcaagcctacaggctacaacaagcgcttgcggcaagcgtcttaca acaaccaattaaccaattgcaacaacaatccttggcacatctaaccatac aaaccatcgcaacgcaacagcaacaacagttcctaccagcactgagccaa ctagatgtggtgaaccctgtcgcctacttgcaacagcagctgcttgcatc caacccacttgctctggcaaacgtagctgcataccaacaacaacaacaat tgcagcagtttctgccagcgctcagtcaacta Gamma-Gliadin precursor—AAA34272—Scheets et al., 1988 Plant Sci. 57:141-150.
Protein Sequence:

SEQ ID NO: 23
NMQVDPSGQV QWPQQQPFPQ PQQPFCQQPQ RTIPQPHQTF

HHQPQQTFPQ PQQTYPHQPQ QQFPQPQQPQ QPFPQPQQTF

PQQPQLPFPQ QPQQPFPQPQ QPQQPFPQSQ QPQQPFPQPQ

QQFPQPQQPQ QSFPQQQQPA IQSFLQQQMN PCKNFLLQQC

NHVSLVSSLV SIILPRSDCQ VMQQQCCQQL AQIPQQLQCA

AIHSVAHSII MQQEQQQGVP ILRPLFQLAQ GLGIIQPQQP

AQLEGIRSLV LKTLPTMCNV YVPPDCSTIN VPYANIDAGI GGQ

DNA Sequence (M36999)

SEQ ID NO: 24
gcatgcattg tcaaagtttg tgaagtagaa ttaataacct tttggttatt gatcactgta tgtatcttag atgtcccgta gcaacggtaa gggcattcac ctagtactag tccaatatta attaataact tgcacagaat tacaaccatt gacataaaaa ggaaatatga tgagtcatgt attgattcat gttcaacatt actacccttg acataaaaga agaatttgac gagtcgtatt agcttgttca tcttaccatc atactatact gcaagctagt ttaaaaaaga atyaaagtcc agaatgaaca gtagaatagc ctgatctatc tttaacaaca tgcacaagaa tacaaattta gtcccttgca agctatgaag atttggttta tgcctaacaa catgataaac ttagatccaa aaggaatgca atctagataa ttgtttgact tgtaaagtcg ataagatgag tcagtgccaa -continued

```
ttataaagtt ttcgccactc ttagatcata tgtacaataa aaaggcaact ttgctgacca ctccaaaagt acgtttgtat gtagtgccac caaacacaac acaccaaata atcagtttga taagcatcga atcactttaa aaagtgaaag aaataatgaa aagaaaccta accatggtag ctataaaaag cctgtaatat gtacactcca taccatcatc catccttcac acaactagag cacaagcatc aaatccaagt aagtattagt t aacgcaaat ccaccatgaa gaccttactc atcctaacaa tccttgcgat ggcaacaacc atcgccaccg ccaatatgca agtcgacccc agcggccaag tacaatggcc acaacaacaa ccattccccc agccccaaca accattctgc cagcaaccac aacgaactat tccccaaccc catcaaacat tccaccatca accacaacaa acatttcccc aaccccaaca acataccccc catcaaccac aacaacaatt tccccagacc caacaaccac aacaaccatt tccccagccc caacaaacat tcccccaaca accccaacta ccatttcccc aacaacccca acaaccattc ccccagcctc agcaacccca caaccatttt cccagtcac aacaaccaca acaaccttttt ccccagcccc aacaacaatt tccgcagccc caacaaccac aacaatcatt cccccaacaa caacaaccgg cgattcagtc atttctacaa caacagatga accccctgcaa gaatttcctc ttgcagcaat gcaaccatgt gtcattggtg tcatctctcg tgtcaataat tttgccacga agtgattgcc aggtgatgca gcaacaatgt tgccaacaac tagcacaaat tcctcaacag ctccagtgcg cagccatcca cagcgtcgcg cattccatca tcatgcaaca agaacaacaa caaggcgtgc cgatcctgcg gccactattt cagctcgccc agggtctggg tatcatccaa cctcaacaac cagctcaatt ggaggggatc aggtcattgg tattgaaaac tcttccaacc atgtgcaacg tgtatgtgcc acctgactgc tccaccatca acgtaccata tgccaacata gacgctggca ttggtggcca atgaaaaatg caagatcatc attgcttagc tgatgcacca atcgttgtag cgatgacaaa taaagtggtg tgcaccatca tgtgtgaccc cgaccagtgc tagttcaagc ttgggaataa aagacaaaca aagttcttgt ttgctagcat tgcttgtcac tgttacattc acttttttatt tcgatgttca tccctaaccg caatcctagc cttacacgtc aatagctagc tgcttgtgct ggcaggttac tatataatct atcaattaat ggtcgaccta ttaatccaag taataggcta ttgatagact gctcccaagc cgaccgagca cctatcagtt acggatttct tgaacattgc acactataat aattcaacgt atttcaacct ctagaagtaa aagggcatttt agtagc
```

Beta zein—AF371264—Woo et al., (2001) Plant Cell 13 (10), 2297-2317.

DNA

SEQ ID NO: 25

```
atgaagatggtcatcgttctcgtcgtgtgcctggctctgtcagctgccag cgcctctgcaatgcagatgccctgcccctgcgcggggctgcagggcttgt acggcgctggcgccggcctgacgacgatgatgggcgccggcgggctgtac ccctacgcggagtacctgaggcagccgcagtgcagcccgctggcggcggc gccctactacgccgggtgtgggcagccgagcgccatgttccagccgctcc ggcaacagtgctgccagcagcagatgaggatgatggacgtgcagtccgtc gcgcagcagctgcagatgatgatgcagcttgagcgtgccgctgccgccag cagcagcctgtacgagccagctctgatgcagcagcagcagcagctgctgg cagcccagggtctcaacccatggccatgatgatggcgcagaacatgccg gccatgggtggactctaccagtaccagctgcccagctaccgcaccaaccc ctgtggcgtctccgctgccattccgccctactactga
```

Protein

SEQ ID NO: 26

MKMVIVLVVCLALSAASASAMQMPCPCAGLQGLYGAGAGLTTMMGAGGLY

PYAEYLRQPQCSPLAAAPYYAGCGQPSAMFQPLRQQCCQQQMRMMDVQSV

AQQLQMMMQLERAAAASSSLYEPALMQQQQQLLAAQGLNPMAMMMAQNMP

AMGGLYQYQLPSYRTNPCGVSAAIPPYY

Delta zein 10 kD—AF371266—Woo et al., (2001) Plant Cell 13 (10), 2297-2317, and Kirihara et al., (1988) Gene. November 30; 71(2):359-70.

DNA

SEQ ID NO: 27

```
atggcagccaagatgcttgcattgttcgctctcctagctctttgtgcaag cgccactagtgcgacgcatattccagggcacttgccaccagtcatgccat tgggtaccatgaacccatgcatgcagtactgcatgatgcaacaggggctt gccagcttgatggcgtgtccgtccctgatgctgcagcaactgttggcctt accgcttcagacgatgccagtgatgatgccacagatgatgacgcctaaca tgatgtcaccattgatgatgccgagcatgatgtcaccaatggtcttgccg agcatgatgtcgcaaatgatgatgccacaatgtcactgcgacgccgtctc gcagattatgctgcaacagcagttaccattcatgttcaacccaatggcca tgacgattccacccatgttcttacagcaaccctttgttggtgctgcattc tag
```

Protein

SEQ ID NO: 28

MAAKMLALFALLALCASATSATHIPGHLPPVMPLGTMNPCMQYCMMQQGL

ASLMACPSLMLQQLLALPLQTMPVMMPQMMTPNMMSPLMMPSMMSPMVLP

SMMSQMMMPQCHCDAVSQIMLQQQLPFMFNPMAMTIPPMFLQQPFVGAAF

Signal Peptides
Gamma-Zein

SEQ ID NO: 29
Met Arg Val Leu Leu Val Ala Leu Ala Leu Leu Ala
Leu Ala Ala Ser Ala Thr Ser

Alpha-Gliadin

SEQ ID NO: 30
Met Lys Thr Phe Leu Ile Leu Val Leu Leu Ala Ile
Val Ala Thr Thr Ala Thr Thr Ala

Gamma-Gliadin

SEQ ID NO: 31
Met Lys Thr Leu Leu Ile Leu Thr Ile Leu Ala Met
Ala Ile Thr Ile Gly Thr Ala Asn Met

PR10

SEQ ID NO: 32
Met Asn Phe Leu Lys Ser Phe Pro Phe Tyr Ala Phe
Leu Cys Phe Gly Gln Tyr Phe Val Ala Val Thr His
Ala

T-Cell Stimulating Immunogenic Polypeptides

A large number of T-cell-stimulating immunogenic polypeptide sequences have been identified in the literature. A partial list is provided below in the table below using the single letter code.

| | | T Cell Epitopes | | |
|---|---|---|---|---|
| Organism | Protein | Sequence* | Citation | SEQ ID NO |
| HIV | P24 | GPKEPFRDY-VDRFYKC | 1 | 33 |
| Corynebacterium diptheriae | toxin | FQVVHNSYN-RPAYSPGC | 2 | 34 |
| Borrelia burgdorferi | ospA | VEIKEGTVTLKRE-IDKNGKVTVSLC | 3 | 35 |
| | | TLSKNISKSG-EVSVELNDC | 4 | 36 |
| Influenza Virus A8/PR8 | HA | SSVSSFERFEC | 5 | 37 |
| | | LIDALLGDPC | 6 | 38 |
| | | TLIDALLGC | 6 | 39 |
| | NP | FWRGENGRKTRS-AYERMCNILKGK | 7 | 40 |
| | | LRVLSFIRGTKV-SPRGKLSTRG | 7 | 41 |
| | | SLVGIDPFKLLQ-NSQVYSLIRP | 7 | 42 |
| | | AVKGVGTMVMEL-IRMIKRGINDRN | 7 | 43 |
| Trypanosoma cruzi | | SHNFTLVASVII-EEAPSGNTC | 8 | 44 |
| Plasmodium falciparum | MSP1 | SVQIPKVPYPNGIVYC | 9 | 45 |
| | | DFNHYYTLKTGLEADC | | 46 |
| | | PSDKHIEQYKKI-KNSISC | 10 | 47 |
| | | EYLNKIQNSLST-EWSPCSVT | 11 | 48 |
| P. vivax | | YLDKVRATVGTE-WTPCSVT | 22 | 49 |
| P. yoelii | | EFVKQISSQLTE-EWSQCSVT | 22 | 50 |
| Streptococcus sobrinus | AgI/II | KPRPIYEAKL-AQNQKC | 12 | 51 |
| | | AKADYEAKLA-QYEKDLC | | 52 |
| LCMV (lymphocytic choriomeningitis virus) | NP | RPQASGVYM-GNLTAQC | 13 | 53 |
| Clostridium tetani | tox | QYIKANSKFIG-ITELC | 14 | 54 |
| Neisseria meningitidis | PorB | AIWQVEQKASIAGTDSGWC | 21 | 55 |
| | | NYKNGGFFVQYGGAYKRHC | 21 | 56 |
| | | HNSQTEVAATLAYRFGNVC | 21 | 57 |

T Cell Epitopes

| Organism | Protein | Sequence* | Citation | SEQ ID NO |
|---|---|---|---|---|
| | PorB | TPRVSYAHGFKGLVDDADC | 21 | 58 |
| | | RFGNAVPRISYAHGFDFIC | 21 | 59 |
| | | AFKYARHANVGRNAFELFC | 21 | 60 |
| | | SGAWLKRNTGIGNYTQINAC | 21 | 61 |
| | | AGEFGTLRAGRVANQC | 21 | 62 |
| | | IGNYTQINAASVGLRC | 21 | 63 |
| | | GRNYQLQLTEQPSRTC | 21 | 64 |
| | | SGSVQFVPAQNSKSAC | 21 | 65 |
| | | HANVGRDAFNLFLLGC | 21 | 66 |
| | | LGRIGDDDEAKGTDPC | 21 | 67 |
| | | SVQFVPAQNSKSAYKC | 21 | 68 |
| | | NYAFKYAKHANVGRDC | 21 | 69 |
| | | AHGFDFIERGKKGENC | 21 | 70 |
| | | GVDYDFSKRTSAIVSC | 21 | 71 |
| | | HDDMPVSVRYDSPDFC | 21 | 72 |
| | | RFGNAVPRISYAHGFD3FIERGKKGENC | 21 | 73 |
| | | NYAFKYAKHANVGRDA-FNLFLLGC | 21 | 74 |
| | | SGAWLKRNTGIGNYTQ-INAASVGLRC | 21 | 75 |
| | | SGSVQFVPAQNSKSAYTPAC | 21 | 76 |
| | OpaB | TGANNTSTVSDYFRNRITC | 21 | 77 |
| | | IYDFKLNDKFDKFKPYIGC | 21 | 78 |
| | Opa-5d | LSAIYDFKLNDKFKPYIGC | 21 | 79 |
| | Opac | NGWYINPWSEVKFDLNSRC | 21 | 80 |
| Hepatitis B | Surface PreS1 | MGTNLSVPN-PLGFFPDHQLDP | 15, 16 | 81 |
| | | PLGFFPDH | | 82 |
| | | PLGFFPDHQL | | 83 |
| | PreS2 | MQWNSTAFHQ-TLQDPRVRG-LYLPAGG | 15 | 84 |
| | | MQWSTAFHQ-TLQDP | | 85 |
| | | MQWNSTALHQ-ALQDP | | 86 |
| | | QDPRVR | 17 | 87 |
| | Core | MDIDPYKEFGAT-VELLSFLP | 18 | 88 |
| | | RDLLDTASALYR-EALESPEHCSPHH | 18 | 89 |
| | | TWVGVNLEDPAS-RDLVVSYVNTNMG | 18 | 90 |
| | | VVSYVNTNMGL-KFRQL | 18 | 91 |
| | | LLWFHISCLTF-GRETVIEYLV | 18 | 92 |
| | | LLWFHISCLTF-VSFGVWIRTPP-AYRPPNAPIL | 18 | 93 |
| | | VSFGVWIRTPPA | 18 | 94 |
| | | | 18 | 95 |
| | | PPAYRPPNAPIL | 18 | 96 |
| | | WIRTPPAYRPPN | 18 | 97 |
| | | PHHTALRQAIL-CWGELMTLA | 19 | 98 |
| *M. tuberculosis* | 65 KD Protein | AVLEDPYILLVSSKV | 20 | 99 |
| | | LLVSSKVSTVKDLLP | 20 | 100 |
| | | LLPLLEKVIGAGKPL | 20 | 101 |
| | | AILTGGQVISEEVGL | 20 | 102 |
| | | IAFNSGLEPGVVAEK | 20 | 103 |
| | | ARRGLERGLNAL-ADAVKV | 20 | 104 |
| | | EKIGAELVKEVAKK | 20 | 105 |
| | | GLKRGIEKAVEKVETL | 20 | 106 |
| | | IEDAVRNAKAAVEEG | 20 | 107 |
| HPV-16 | E6 Protein | TIHDIILEC | 23 | 121 |
| | | FAFRDLCIVY | 23 | 122 |

T Cell Epitopes

| Organism | Protein | Sequence* | Citation | SEQ ID NO |
|---|---|---|---|---|
| | E7 Protein | YMLDLQPETT | 23 | 123 |
| | | LEDLLMGTL | 23 | 124 |
| | | DLYCYEQLN | 24 | 125 |

*Underlined C (C) is not from the native sequence.

Citations:
1. U.S. Pat. No. 5,639,854.
2. EPO 399001 B1.
3. Bockenstedt et al. (1996) J. Immunol., 157(12):5496-5502.
4. Zhong et al. (1996) Eur. J. Immunol., 26(11):2749.
5. Brumeanu et al. (1996) Immunotechnology, 2(2):85-95.
6. Brown et al. (1993) J. Virol., 67(5):2887-2893.
7. Brett et al., (1991) J. Immunol., 147(3):984-991.
8. Kahn et al. (1997) J. Immunol., 159(9):4444.
9. Ohta et al. (1997) Int. Arch. Allergy Immunol., 114(1):15.
10. U.S. Pat. No. 4,886,782.
11. Calvo-Calle et al. (1997) J. Immunol. 159(3):1362-1373.
12. Staffileno et al. (1990) Arch. Oral Biol., 35: Suppl. 47S.
13. Saron et al. (1997) Proc. Natl. Acad. Sci. USA 94(7): 3314-3319.
14. Yang et al. (1997) Vaccine, 15(4):377-386.
15. Neurath et al., (1986) F. Brown et al. eds., Vaccines 85, Cold Spring Harbor Laboratory, Cold Spring Harbor, N.Y., pp. 185-189.
16. Milich et al., (1987) F. Brown et al. eds., Vaccines 87, Cold Spring Harbor Laboratory, Cold Spring Harbor, N.Y., pp. 50-55.
17. Kent et al., (1987) F. Brown et al. eds., Vaccines 86, Cold Spring Harbor Laboratory, Cold Spring Harbor, N.Y., pp. 365-369.
18. U.S. Pat. No. 4,882,145.
19. Alexander et al., (1994) Immunity 1:751-761.
20. U.S. Pat. No. 5,478,726
21. WO 03/072731
22. U.S. Pat. No. 6,942,866
23. U.S. Patent Publication 20060182763
24. U.S. Pat. No. 7,329,498.

A group of preferred T-cell stimulating immunogenic sequences are present in HPV-16, in the E7 gene. In order to translate the previously discussed therapeutic DNA vaccine candidate [Osen et al., 2001 Vaccine 19(30):4276-4286] into a vaccine for use in a clinical trial, the safety features were further enhanced. For this reason, no heterologous genes were fused. Rather, immunogenicity was enhanced by placing a Kozak-sequence [Kozak et al., 1987 Nucleic Acids Res 15(20):8125-8148] in front of the gene [Steinberg et al., 2005 Vaccine 23(9):1149-1157]. A plasmid-vector pTHamp [Hanke et al., (1998) Vaccine 16(4):426-435] applicable to humans [Hanke et al., 2000 Nat Med 6(9):951-955] was selected. Many expression vectors are known and available for use for DNA vaccines. See for example, U.S. Pat. No. 7,351,813 B2 and EP 1 026 253 B1 and the citations therein.

Figure 6:
FIG. 6 is a map of the artificial HPV-16 E7SH gene. The HPV-16 E7 wild-type gene (E7WT, above) was dissected at the positions corresponding to the pRB binding site (nt 72/73) and between the two C-X-X-C motifs (nt 177/178 and nt 276/277). The resulting four fragments a, b, c and d were rearranged ("shuffled") forming the core element with the sequence a, d, c, b. To avoid loss of putative CTL epitopes at the junctions a-b, b-c and c-d, these sequences (3×27 nt=3×9 amino acids) were added as an appendix forming the complete HPV-16 E7SH gene. To minimize the potential risk of "back-to-wild-type recombination" the codons of the core element were optimized for expression in humans according to the Kazusa codon usage database that can be found at kazusa.or.jp/codon/. A Kozak sequence was added in front of the gene to enhance translation.

More importantly E7 itself was redesigned. The sequence was taken apart exactly at the positions that are critical for transforming properties of the protein (pRB-binding site, C-X-X-C motifs) and reassembled in a "shuffled" order as "core" gene. This sequence was codon optimized to humans (almost identical to mice). The original junctions destroyed by the dissection were added as an "appendix" with a non-codon optimized sequence to minimize recombination events reconstituting the wild-type sequences (see also FIG. 6).

Tumor protection and regression studies provide a first impression on immunogenicity and effectivity of tumor vaccines. Those studies do not fully reflect, however, the responses induced in humans. "In vitro immunization" of human lymphocytes by antigen-loaded dendritic cells (DCs) can be used as a model of human responses [Norm et al., 2003 J Cancer Res Clin Oncol 129(9):511-520]. Loading of DCs by DNA transfection is a suitable technique [Lohmann et al., 2000 Cancer Gene Ther 7(4):605-614] and specific T cell priming verifies the potential immunogenicity of the DNA vaccine candidate.

The results shown hereinafter illustrate that the HPV-16 E7SH DNA vaccine candidate of the second generation induces specific immunity in vivo in mice and after in vitro immunization of human lymphocytes and, therefore, can provide for a safe therapeutic HPV-vaccine.

The sequence of the gene that expresses the HPV-16 E7SH protein is as follows from 5' to 3':

SEQ ID NO: 126
```
CCC GCC GCC ACC ATG CAC GGC GAC ACC CCC ACC CTG
CAC GAG TAC ATG CTG GAC CTG CAG CCC GAG ACC ACC
GAC CTG TAC TGC ATC TGC AGC CAG AAA CCC AAG TGC
GAC AGC ACC CTG CGG CTG TGC GTG CAG AGC ACC CAC
GTG GAC ATC CGG ACC CTG GAG GAC CTG CTG ATG GGC
ACC CTG GGC ATC GTG TGC CCC TAC GAG CAG CTG AAC
GAC AGC AGC GAG GAG GAG GAT GAG ATC GAC GGC CCC
GCC GGC CAG GCT GAG CCC GAC CGG GCC CAC TAC AAC
ATC GTG ACC TTC TGC TGC CAA CCA GAG ACA ACT GAT
CTC TAC TGT TAT GAG CAA TTA AAT GAC AGC TCA GAG
CAT TAC AAT ATT GTA ACC TTT TGT TGC AAG TGT GAC
TCT ACG CTT CGG TTG TGC ATG GGC ACA CTA GGA ATT
GTG TGC CCC ATC TGT TCT CAG AAA CCA TAA
```

Another group of preferred T-cell stimulating immunogenic sequences are present in HIV-1. In particularly preferred practice, a polypeptide sequence present in HIV-1 is encoded by the HIV-1 gag gene. These sequences are thus present in the P24, P17, P6 or P9 proteins encoded by the gag gene, or a polypeptide such as the P41 polypeptide.

A particular T-cell stimulating immunogenic sequence need not itself be present as a distinct polypeptide in HIV-1 or any other pathogen. Rather, such a sequence is present as a portion of a distinct polypeptide or proteinaceous material encoded by an open reading frame of a pathogenic genome.

Specific T-cell stimulating immunogenic sequences useful herein are provided below.

p41 DNA Sequence 5' to 3'

SEQ ID NO: 108

```
  1 ATGGGTGCTA GAGCTTCTAT TCTTAGAGGT GAAAAGCTTG ATAAGTGGGA AAAGATTAGA
 61 CTTAGACCAG GTGGTAAGAA GCATTATATG CTTAAGCATA TTGTTTGGGC TTCTAGAGAA
121 CTTGAAAGAT TTGCTCTTAA TCCAGGTTTG CTTGAAACTT CTGAAGGTTG TAAGCAAATT
181 ATGAAGCAAC TTCAACCAGC TCTTCAAACT GGTACTGAAG AACTTAAGTC TCTTTATAAT
241 ACTGTTGCTA CTCTTTATTG TGTTCATGAA AAGATTGAAG TTAGAGATAC TAAGGAAGCT
301 CTTGATAAGA TTGAAGAAGA ACAAAATAAG TGTCAACAAA AGACTCAACA AGCTAAGGCT
361 GCTGATGGTA AGGTTTCTCA AAATTATCCA ATTGTTCAAA ATCTTCAAGG TCAAATGGTT
421 CATCAAGCTA TTTCTCCAAG AACTCTTAAT GCTTGGGTTA AGGTTATTGA AGAAAAGGCT
481 TTTTCTCCAG AAGTTATTCC AATGTTTACT GCTCTTTCTG AAGGTGCTAC TCCACAAGAT
541 CTTAATACTA TGCTTAATAC TGTTGGTGGT CATCAAGCTG CTATGCAAAT GCTTAAGGAT
601 ACTATTAATG AAGAAGCTGC TGAATGGGAT AGACTTCATC CAGTTCATGC TGGTCCAATT
661 GCTCCAGGTC AAATGAGAGA ACCAAGAGGT TCTGATATTG CTGGTACTAC TTCTACTCTT
721 CAAGAACAAA TTGCTTGGAT GACTTCTAAT CCACCAATTC CAGTTGGTGA TATTTATAAG
781 AGATGGATTA TTCTTGGTCT TAATAAGATT GTTAGAATGT ATTCTCCAGT TTCTATTCTT
841 GATATTGAC AAGGTCCAAA GGAACCATTT AGAGATTATG TTGATAGATT TTTTAAGACT
901 CTTAGAGCTG AACAAGCTAC TCAAGAAGTT AAGAATTGGA TGACTGATAC TCTTCTTGTT
961 CAAAATGCTA ATCCAGATTG TAAGACTATT CTTAGGGCTC TTGGTCCAGG TGCTACTCTT
1021 GAAGAAATGA TGACTGCTTG TCAAGGTGTT GGTGGTCCAG GTCATAAGGC TAGAGTTCTT
1081 TAA
``` p41 Amino Acid Sequence
Translation of P41 (1-1083)
Universal code
Total amino acid number: 360, MW=40309

Max ORF starts at AA pos 1 (may be DNA pos 1) for 360 AA (1080 bases),
MW=40309
Origin

SEQ ID NO: 109

```
  1 MGARASILRG EKLDKWEKIR LRPGGKKHYM LKHIVWASRE LERFALNPGL LETSEGCKQI
 61 MKQLQPALQT GTEELKSLYN TVATLYCVHE KIEVRDTKEA LDKIEEEQNK CQQKTQQAKA
121 ADGKVSQNYP IVQNLQGQMV HQAISPRTLN AWVKVIEEKA FSPEVIPMFT ALSEGATPQD
181 LNTMLNTVGG HQAAMQMLKD TINEEAAEWD RLHPVHAGPI APGQMREPRG SDIAGTTSTL
241 QEQIAWMTSN PPIPVGDIYK RWIILGLNKI VRMYSPVSIL DIRQGPKEPF RDYVDRFFKT
301 LRAEQATQEV KNWMTDTLLV QNANPDCKTI LRALGPGATL EEMMTACQGV GGPGHKARVL
361 *
``` p24 DNA Sequence 5' to 3'

SEQ ID NO: 110

```
  1 ATGCCAATTG TTCAAAATCT TCAAGGTCAA ATGGTTCATC AAGCTATTTC TCCAAGAACT
 61 CTTAATGCTT GGGTTAAGGT TATTGAAGAA AAGGCTTTTT CTCCAGAAGT TATTCCAATG
121 TTTACTGCTC TTTCTGAAGG TGCTACTCCA CAAGATCTTA ATACTATGCT TAATACTGTT
181 GGTGGTCATC AAGCTGCTAT GCAAATGCTT AAGGATACTA TTAATGAAGA AGCTGCTGAA
241 TGGGATAGAC TTCATCCAGT TCATGCTGGT CCAATTGCTC AGGTCAAAT GAGAGAACCA
```

-continued

```
301 AGAGGTTCTG ATATTGCTGG TACTACTTCT ACTCTTCAAG AACAAATTGC TTGGATGACT

361 TCTAATCCAC CAATTCCAGT TGGTGATATT TATAAGAGAT GGATTATTCT TGGTCTTAAT

421 AAGATTGTTA GAATGTATTC TCCAGTTTCT ATTCTTGATA TTAGACAAGG TCCAAAGGAA

481 CCATTTAGAG ATTATGTTGA TAGATTTTTT AAGACTCTTA GAGCTGAACA AGCTACTCAA

541 GAAGTTAAGA ATTGGATGAC TGATACTCTT CTTGTTCAAA ATGCTAATCC AGATTGTAAG

601 ACTATTCTTA GGGCTCTTGG TCCAGGTGCT ACTCTTGAAG AAATGATGAC TGCTTGTCAA

661 GGTGTTGGTG GTCCAGGTCA TAAGGCTAGA GTTCTTTAA
``` p24 Amino Acid Sequence
Translation of p24 (1-699)
Universal code
Total amino acid number: 232, MW=25660

Max ORF starts at AA pos 1 (may be DNA pos 1) for 232 AA (696 bases),
MW=25660
Origin

SEQ ID NO: 111

```
  1 MPIVQNLQGQ MVHQAISPRT LNAWVKVIEE KAFSPEVIPM FTALSEGATP QDLNTMLNTV

61 GGHQAAMQML KDTINEEAAE WDRLHPVHAG PIAPGQMREP RGSDIAGTTS TLQEQIAWMT

121 SNPPIPVGDI YKRWIILGLN KIVRMYSPVS ILDIRQGPKE PFRDYVDRFF KTLRAEQATQ

181 EVKNWMTDTL LVQNANPDCK TILRALGPGA TLEEMMTACQ GVGGPGHKAR VL
```

RT DNA Sequence 5' to 3'

SEQ ID NO: 112

```
   1 ATGAGGGTGT TGCTCGTTGC CCTCGCTCTC CTGGCTCTCG CTGCGAGCGC CACCTCCACG

61 CATACAAGCG GCGGCTGCGG CTGCCAGCCA CCGCCGCCGG TTCATCTACC GCCGCCGGTG

121 CATCTGCCAC CTCCGGTTCA CCTGCCACCT CCGGTGCATC TCCCACCGCC GGTCCACCTG

181 CCGCCGCCGG TCCACCTGCC ACCGCCGGTC CATGTGCCGC CGCCGGTTCA TCTGCCGCCG

241 CCACCATGCC ACTACCCTAC TCAACCGCCC CGGCCTCAGC CTCATCCCCA GCCACACCCA

301 TGCCCGTGCC AACAGCCGCA TCCAAGCCCG TGCCAGACCA TGGACGACGA TGATAAGTGC

361 GGCAAGAAGG CCATCGGCAC CGTGCTGGTG GGCCCCACCC CCGTGAACAT CATCGGCCGG

421 AACATGCTGA CCCAGCTGGG CTGCACCCTG AACTTCCCCA TCAGCCCCAT CGAGACCGTG

481 CCCGTGAAGC TGAAGCCCGG CATGGACGGC CCCAAGGTGA AGCAGTGGCC CCTGACCGAG

541 GTGAAGATCA AGGCCCTGAC CGCCATCTGC GAGGAGATGG AGAAGGAGGG CAAGATCACC

601 AAGATCGGCC CCGAGAACCC CTACAACACC CCCATCTTCG CCATCAAGAA GGAGGACAGC

661 ACCAAGTGGC GGAAGCTGGT GGACTTCCGG GAGCTGAACA AGCGGACCCA GGACTTCTGG

721 GAGGTGCAGC TGGGCATCCC CCACCCCGCC GGCCTGAAGA AGAAGAAGAG CGTGACCGTG

781 CTGGACGTGG GCGACGCCTA CTTCAGCGTG CCCCTGGACG AGGGCTTCCG GAAGTACACC

841 GCCTTCACCA TCCCCAGCAT CAACAACGAG ACCCCCGGCA TCCGGTACCA GTACAACGTG

901 CTGCCCCAGG GCTGGAAGGG CAGCCCCGCC ATCTTCCAGG CCAGCATGAC CAAGATCCTG

961 GAGCCCTTCC GGGCCAAGAA CCCCGAGATC GTGATCTACC AGTACATGGC CGCCCTGTAC

1021 GTGGGCAGCG ACCTGGAGAT CGGCCAGCAC CGGGCCAAGA TCGAGGAGCT GCGGGAGCAC

1081 CTGCTGAAGT GGGGCTTCAC CACCCCCGAC AAGAAGCACC AGAAGGAGCC CCCCTTCCTG

1141 TGGATGGGCT ACGAGCTGCA CCCCGACAAG TGGACCGTGC AGCCCATCCA GCTGCCCGAG

1201 AAGGACAGCT GGACCGTGAA CGACATCCAG AAGCTGGTGG GCAAGCTGAA CTGGACCAGC

1261 CAGATCTACC CCGGCATCAA GGTGCGGCAG CTGTGCAAGC TGCTGCGGGG CACCAAGGCC
```

-continued

```
1321 CTGACCGACA TCGTGCCCCT GACCGAGGAG GCCGAGCTGG AGCTGCCGA GAACCGGGAG

1381 ATCCTGAAGG AGCCCGTGCA CGGCGTGTAC TACGACCCCA GCAAGGACCT GATCGCCGAG

1441 ATCCAGAAGC AGGGCGACGA CCAGTGGACC TACCAGATCT ACCAGGAGCC CTTCAAGAAC

1501 CTGAAAACCG GCAAGTACGC CAAGCGGCGG ACCACCCACA CCAACGACGT GAAGCAGCTG

1561 ACCGAGGCCG TGCAGAAGAT CAGCCTGGAG AGCATCGTGA CCTGGGGCAA GACCCCCAAG

1621 TTCCGGCTGC CCATCCAGAA GGAGACCTGG GAGATCTGGT GGACCGACTA CTGGCAGGCC

1681 ACCTGGATCC CCGAGTGGGA GTTCGTGAAC AGCGGCCGCT TCGAATCTA G
```

RT Amino Acid Sequence
Translation of RT (1-1731)
Universal code
Total amino acid number: 576, MW=65360

Max ORF starts at AA pos 1 (may be DNA pos 1) for 576 AA (1728 bases),
MW=65360
Origin

SEQ ID NO: 113

```
  1 MRVLLVALAL LALAASATST HTSGGCGCQP PPPVHLPPPV HLPPPVHLPP PVHLPPPVHL

61 PPPVHLPPPV HVPPPVHLPP PPCHYPTQPP RPQPHPQPHP CPCQQPHPSP CQTMDDDDKC

121 GKKAIGTVLV GPTPVNIIGR NMLTQLGCTL NFPISPIETV PVKLKPGMDG PKVKQWPLTE

181 VKIKALTAIC EEMEKEGKIT KIGPENPYNT PIFAIKKEDS TKWRKLVDFR ELNKRTQDFW

241 EVQLGIPHPA GLKKKKSVTV LDVGDAYFSV PLDEGFRKYT AFTIPSINNE TPGIRYQYNV

301 LPQGWKGSPA IFQASMTKIL EPFRAKNPEI VIYQYMAALY VGSDLEIGQH RAKIEELREH

361 LLKWGFTTPD KKHQKEPPFL WMGYELHPDK WTVQPIQLPE KDSWTVNDIQ KLVGKLNWTS

421 QIYPGIKVRQ LCKLLRGTKA LTDIVPLTEE AELELAENRE ILKEPVHGVY YDPSKDLIAE

481 IQKQGDDQWT YQIYQEPFKN LKTGKYAKRR TTHTNDVKQL TEAVQKISLE SIVIWGKTPK

541 FRLPIQKETW EIWWTDYWQA TWIPEWEFVN SGRFRI*
```

NSs DNA Sequence 5' to 3'
NSs is a silencing suppressor used in the agroinfiltration of tobacco plants.

SEQ ID NO: 114

```
  1 ATGTCTTCAA GTGTTTATGA GTCGATCATT CAGACAAAAG CTTCAGTCTG GGGATCAACT

61 GCATCTGGTA AAGCTGTTGT AGATTCTTAC TGGATTCATG AACTTGGTAC TGGTTCTCCA

121 CTAGTTCAAA CCCAGCTGTA TTCTGATTCA AGAAGCAAAA GTAGCTTTGG CTATACTGCA

181 AAGGTAGGGA ATCTTCCCTG TGAGGAAGAA GAAATTCTTT CTCAGCATGT GTATATCCCT

241 ATTTTTGATG ATGTTGATTT TAGCATCAAT ATTGATGACT CTGTTCTGGC ACTGTCTGTT

301 TGCTCCAACA CAGTCAATAC TAACGGAGTG AAACATCAAG GTCATTTGAA AGTTTTGTCT

361 CCTGCTCAGC TCCACTCTAT TGGATCTACC ATGAACGGAT CTGATATTAC AGACCGATTC

421 CAGCTCCAAG AAAAGATAT AATTCCCAAT GACAGGTACA TTGAAGCTGT AAACAAAGGC

481 TCTTTGTCTT GTGTTAAAGA GCATACCTAT AAGGTCGAGA TGTGCTACAA TCAAGCTTTA

541 GGCAAAGTGA ATGTTCTATC CCCTAACAGA AATGTCCATG AATGGCTGTA CAGTTTCAAG

601 CCAAATTTCA ATCAAGTTGA AAGCAACAAC AGAACTGTAA ATTCTCTTGC AGTGAAATCT

661 CTGCTCATGT CAGCAGGAAA TAACATCATG CCTAACTCTC AGGCTTTTGT CAAAGCTTCC

721 ACTGATTCTC ATTTCAAGCT GAGCCTCTGG CTAAGAGTTC AAAGGTTTT GAAGCAGATT

781 TCCATTCAGA AATTGTTCAA AGTTGCAGGA GATGAAACTA ACAAAACATT TTATTTATCT

841 ATTGCTTGCA TTCCAAACCA TAACAGTGTT GAGACAGCTT TAAACATTTC TGTTATTTGC
```

```
-continued
 901 AAGCATCAGC TCCCAATCCG TAAATTTAAA GCTCCTTTTG AATTATCAAT GATGTTTTCT

961 GATTTAAAGG AGCCTTACAA CATTGTTCAT GATCCTTCAT ATCCTCAGAG GATTGTTCAT

1021 GCTCTGCTTG AAACTCACAC GTCTTTTGCA CAAGTTCTTT GCAACAACTT GCAAGAAGAC

1081 GTGATCATCT ACACTTTGAA CAACTATGAG CTAACTCCTG GAAAGTTAGA TCTAGGTGAA

1141 AGAACCTTAA ATTACAGTGA AGATGTCTGC AAAAGGAAAT ATTTCCTCTC AAAAACACTT

1201 GAATGTCTTC CATCTAACAC ACAAACTATG TCTTACTTAG ACAGCATCCA AATCCCTTCC

1261 TGGAAGATAG ACTTTGCTAG GGGAGAAATT AAAATTTCTC CACAATCTGT TTCAGTTGCA

1321 AAATCTTTGT TAAAGCTTGA TTTAAGTGGG ATCAAAAAGA AAGAATCTAA GATTTCGGAA

1381 GCATGTGCTT CAGGATCAAA ATAA
```

Translation of NSs (1-1404)
Universal code
Total amino acid number: 467, MW=52121
Max ORF starts at AA pos 1 (may be DNA pos 1) for 467 AA (1401 bases),
MW=52121
Origin

```
                                                          SEQ ID NO: 115
  1 MSSSVYESII QTKASVWGST ASGKAVVDSY WIHELGTGSP LVQTQLYSDS RSKSSFGYTA

61 KVGNLPCEEE EILSQHVYIP IFDDVDFSIN IDDSVLALSV CSNTVNTNGV KHQGHLKVLS

121 PAQLHSIGST MNGSDITDRF QLQEKDIIPN DRYIEAVNKG SLSCVKEHTY KVEMCYNQAL

181 GKVNVLSPNR NVHEWLYSFK PNFNQVESNN RTVNSLAVKS LLMSAGNNIM PNSQAFVKAS

241 TDSHFKLSLW LRVPKVLKQI SIQKLFKVAG DETNKTFYLS IACIPNHNSV ETALNISVIC

301 KHQLPIRKFK APFELSMMFS DLKEPYNIVH DPSYPQRIVH ALLETHTSFA QVLCNNLQED

361 VIIYTLNNYE LTPGKLDLGE RTLNYSEDVC KRKYFLSKTL ECLPSNTQTM SYLDSIQIPS

421 WKIDFARGEI KISPQSVSVA KSLLKLDLSG IKKKESKISE ACASGSK*
```

Gag CD8 Peptide Amino Acid Sequence

```
        AMQMLKDTI          SEQ ID NO: 116
```

Gag CD4 (13) Peptide Amino Acid Sequence

```
    NPPIPVGDIYKRWIIGLNK    SEQ ID NO: 117
```

Gag CD4 (17) Peptide Amino Acid Sequence

```
    FRDYVDRFFKTLRAEQATQE   SEQ ID NO: 118
```

RT CD4 Peptide Amino Acid Sequence

```
    PKVKQWPLTEVKIKALTAI    SEQ ID NO: 119
```

RT CD8 Peptide Amino Acid Sequence

```
        VYYDPSKDLIA        SEQ ID NO: 120
```

T-cell stimulating immunogenicity of a contemplated adjuvant can be measured by a variety of well known techniques. In usual practice, a host animal is inoculated with a contemplated RPBLA vaccine or inoculum, and peripheral mononuclear blood cells (PMBC) are thereafter collected. Those PMBC are then cultured in vitro in the presence of the biologically active polypeptide (T cell immunogen) for a period of about three to five days. The cultured PMBC are then assayed for proliferation or secretion of a cytokine such as IL-2, GM-CSF of IFN-γ. Assays for T cell activation are well known in the art. See, for example, U.S. Pat. No. 5,478,726 and the art cited therein.

A contemplated adjuvant is typically prepared from a recovered RPBLA particles by dispersing the RPBLAs in a physiologically tolerable (acceptable) diluent vehicle such as water, saline, phosphate-buffered saline (PBS), acetate-buffered saline (ABS), Ringer's solution, or the like to form an aqueous composition. The diluent vehicle can also include oleaginous materials such as peanut oil, squalane, squalene and the like as are well known.

The preparation of adjuvants that contain proteinaceous materials as active ingredients is also well understood in the art. Typically, such adjuvants are prepared as parenterals, either as liquid solutions or suspensions; solid forms suitable for solution in, or suspension in, liquid prior to injection can also be prepared. The preparation can also be emulsified, which is particularly preferred.

The immunogenically active RPBLAs are often mixed with excipients that are pharmaceutically acceptable and compatible with the active ingredient. Suitable excipients are, for example, dextrose, glycerol, ethanol, or the like and combinations thereof. In addition, if desired, an adjuvant can contain minor amounts of auxiliary substances such as wetting or emulsifying agents, pH buffering agents that enhance the immunogenic effectiveness of the composition.

Without further elaboration, it is believed that one skilled in the art can, using the preceding description and the detailed examples below, utilize the present invention to its fullest extent. The following preferred specific embodiments are, therefore, to be construed as merely illustrative, and not limiting of the remainder of the disclosure in any way whatsoever.

Example 1

Plasmid Construction and Plant Transformation

DNA encoding HIV-1 p24, p41 and RT from a cloned South African HIV isolate Du422 (GenBank accession no. AF544010) was fused to Zera® using PCR and subsequently cloned into an *A. tumefaciens* binary expression vector pTRAc (Meyers, *BMC Biotechnology* 2008 8:53) in *E. coli* to yield the recombinant clone pTRAcRX3p24, pTRAcRX3p41 and pTRAcRX3RT.

The HPV-16 E7SH gene was engineered by three consecutive PCR reactions as described in [Steinberg et al., 2995 *Vaccine* 23(9):1149-1157]. The resulting HPV16 E7SH gene was amplified by PCR and an enterokinase site was added to the 5' end of the protein. This construct was then fused to RX3 by replacing GFP in an *A. tumefaciens* binary vector pTRA C [Mclean et al., 2007 J Gen Virol 88:1460-1469] that contained a RX3 GFP fusion gene.

The recombinant clone was purified from *E. coli*, and electroporated into competent host *A. tumefaciens* GV3101:: pMP90RK cells. Recombinant *A. tumefaciens* cultures containing pTRAcRX3p24, pTRAcRX3p41, pTRAcRX3RT and pRX3E7SH were injection-infiltrated into the leaves of 6-week old *N. benthamiana* plants using a needle and syringe. The leaves were co-infiltrated with *A. tumefaciens* LBA4404 containing a silencing suppressor pBIN-NS to enhance transient protein expression. The infiltrated plants were grown at 22° C. under a 16 hour: 8 hour light:dark cycle.

Harvesting and Purification of Transiently-Expressed RX3 Fusion Proteins

Approximately 10 g of infiltrated leaf tissue was ground up in liquid nitrogen and resuspended in 20 ml of buffer PBP3 (100 mM Tris pH8, 50 mM KCl, 6 mM $MgCl_2$, 10 mM EDTA and 0.4M NaCl). This suspension was homogenized for 3 minutes and then filtered through miracloth (a quick filtration material for gelatinous homogenates and for protoplast isolation that is composed of rayon polyester with a pore size of 22-25 mm and an acrylic binder that is available from Calbiochem®, San Diego, Calif.). The filtrate was loaded on top of a density step gradient. The gradient comprised of 7 ml volumes of 15, 25, 35 and 45% concentrations of Optiprep® density gradient medium made up in buffer PBP3. The gradient was centrifuged for 2 hours at 80 000Xg in a Beckman SW28 rotor at 4° C. The pellet was resuspended in 500 μl of buffer PBP3 and an aliquot stored for analysis. The remainder was stored at −70° C.

Example 2

Immunization of Mice

HIV Group Study

Female BALB/c mice (8 to 10 weeks old) were divided into the appropriate number of groups (5 mice per group):

Group 1—vDNA prime

Group 2—vDNA prime+vDNA boost

Group 3—vDNA prime+RPBLAs boost

Group 4—RPBLAs prime

The DNA vaccines (vDNA) used in the prime and boost inoculations correspond to: (i) pTHGagC that expresses the Du422 HIV-1 subtype C Gag (van Harmelen, 2003), was manufactured by Aldevron, Fargo, N. Dak., USA and resuspended at 1 mg DNA/ml saline and (ii) pVRCgrttn, that express five HIV-1 subtype C genes gag, reverse transcriptase (RT), tat, and nef (Burgers et al., *AIDS Research and Human Retroviruses* 2008 24(2):195-206). The vDNA (100 μg DNA/100 μl saline) was administered by injecting 50 μl into each tibialis anterior muscle.

For intramuscular inoculation with the RPBLAs containing the corresponding RX3 fusion proteins (RX3-p24, RX3-p41 and RX3-RT), 100 μl of the corresponding RPBLAs fraction isolated as described above and resuspended in saline buffer The following amounts of RPBLAs were injected into the tibialis anterior muscle: 3.6 μg for RX3-p24; 3.1 μg for RX3-p41; and 4 μg for RX3-RT.

HPV Group Study

DNA Vaccination

Six- to eight-week-old female C57BL/6 mice were injected with 50 μl of 10 μM cardiotoxin into each tibialis anterior muscle 5-6 days prior to DNA injection. For vaccination, 50 μl of plasmid DNA (1 μg/μl in PBS) was injected into each pretreated muscle. Ten days later, mice were sacrificed and splenocytes were isolated from the spleen.

Tumor Protection and Regression Studies

Tumor protection and regression studies were performed essentially as described in (Öhlschlager et al., Vaccine 2006 24(2):2880-2893). The specific modifications of the protocol are indicated in the corresponding experiments.

Example 3

IFN-γ and IL-2 ELISPOT Assay

HIV Antigens

A single cell suspension of splenocytes was prepared from spleens harvested on day 12 or 40 and pooled from 5 mice per group. IFN-γ ELISPOT responses were measured using a mouse IL-2 or IFN-γ ELISPOT set (BD Pharmingen). Splenocytes were plated in triplicate at $5\times10^5$/well in a final volume of 200 μl R10 culture medium (RPMI with 10% heat inactivated FCS, Gibco, containing 15 mM β-mercaptoethanol, 100 U penicillin per ml, and 100 μg streptomycin).

The peptides (>95% pure, Bachem, Switzerland) GagCD8 AMQMLKDTI (SEQ ID NO:116) gag CD4(13) NPPIPVGDIYKRWIIGLNK (SEQ ID NO:117) gag CD4 (17) FRDYVDRFFKTLRAEQATQE (SEQ ID NO:118), RT(CD8) VYYDPSKDLIA (SEQ ID NO:120), or RT(CD4) PKVKQWPLTEVKIKALTAI (SEQ ID NO:119), were used as stimuli in the assay at a final concentration of 4 μg/ml. Reactions containing an irrelevant H-$2K^d$ binding peptide TYSTVASSL (SEQ ID NO:1), (obtained from Elizabeth Reap, AlphaVax) or without peptide served as background controls. Spots were detected with the detection antibody at 22 hours, developed with Nova Red then counted using a CTL Analyzer (Cellular Technology, Ohio, USA) with Immunospot Version 3.0 software. The average number of spots in triplicate wells was calculated and results are expressed as the average number of spot-forming units (SFU) per $10^6$ splenocytes±the standard deviation (SD). For each group of mice, the average background spots obtained in the absence of peptide and in the presence of the irrelevant peptide plus one standard deviation of this average was considered as the cut-off for a positive response.

HPV Antigens

In all studies, ELISPOTs were performed ex vivo essentially as described in (Steinberg et al., 2005 *Vaccine* 23:1149-1157). Murine IFN-gamma Elispot assays were performed ex vivo and 5 or 6 days after each in vitro restimulation as described earlier (Ohlschlager et al., 2006). The granzyme B Elispot assay was performed similarly to the IFN-gamma Elispot Assay. For this assay, the anti-mouse granzyme capture antibody (100 ng/well, clone R4-6A2; PharMingen, San Diego, USA) and the biotinylated anti-mouse granzyme detection antibody (50 ng/well, clone XMG1.2; PharMingen, San Diego, USA) were used.

Example 4

Western Blot of Antiserum

Western blots were carried out using a LAV Blot I commercial kit (Biorad). Mouse serum from inoculated mice was used to detect antibodies with goat anti-mouse IgG conjugated to alkaline phosphatase.

Example 5

Isolation (Purification) of RPBLAs Containing RX3-p24, RX3-p41 or RX3-RT by Density Gradient from Agroinfiltrated Tobacco Leaves Approximately 10 g of leaf tissue agroinfiltrated with the corresponding construct (pRX3-p24, pRX3-p41 or pRX3-RT) was ground up in liquid nitrogen and resuspended in 20 ml of buffer PBP3 (100 mM Tris pH8, 50 mM KCl, 6 mM $MgCl_2$, 10 mM EDTA and 0.4M NaCl). This was homogenized for 3 minutes on ice using a Polytron homogenizer and then filtered through miracloth. The corresponding filtrate was loaded on top of a density step gradient, comprising of 7 ml volumes of 15, 25, 35 and 45% concentrations of Optiprep® density gradient medium made up in buffer PBP3. The gradient was centrifuged for 2 hours at 80,000×g in a Beckman SW28 rotor at 4° C. The pellet was resuspended in 500 µl buffer PBP3 to check for the presence of RPBLAs by optic microscopy, and an aliquot stored for analysis. The remainder was stored at −70° C.

Figure 1B:
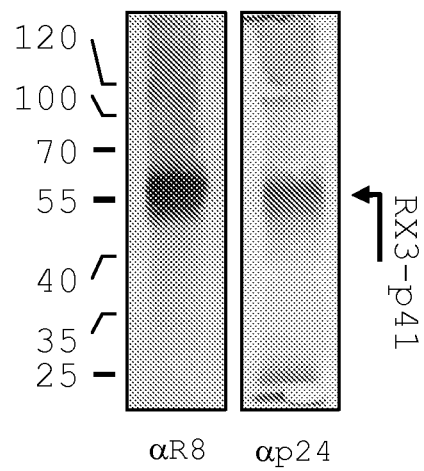
Figure 1C:
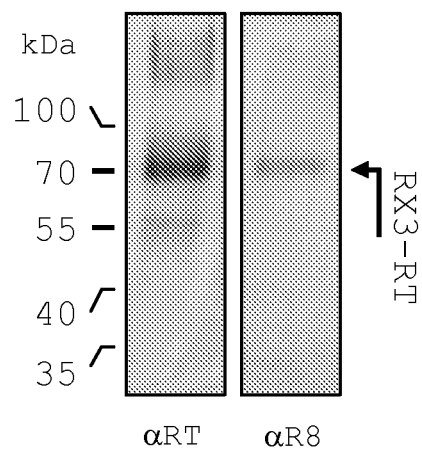

To verify that the RPBLAs fraction contained the corresponding RX3 fusion protein, an aliquot of it was analyzed by western blot using anti-RX3 and anti-p24 antibodies to verify the integrity of the fusion protein (FIG. 1). The amount of immunogen was quantified by densitometric analysis of a western blot dilutions of HIV-1 p17/p24 (also referred as p41) and HIV-1 RT as standards. The concentration of the corresponding immunogen was estimated to 36 ng/µl for RX3-p24, 31 ng/µl for RX3-p41 and approximately 40 ng/µl for RX-RT.

Example 6

Determination of the Cellular Response Triggered by the Intramuscular Inoculation of RX3-p24

To determine the cellular immune response induced by the administration of RX3-p24 containing RPBLAs, four groups of mice were inoculated as follows: (i) mice inoculated with the DNA vaccine (pTHGagx1), (ii) mice inoculated with the DNA vaccine and boosted with another dose of the same DNA vaccine (pTHGagx2), (iii) mice inoculated with the DNA vaccine and boosted with RPBLAs containing RX3-p24 and no further DNA (pTHGag+RX3-p24), and (iv) mice inoculated exclusively with RPBLAs containing RX3-p24 (RX3-p24).

Figure 2A:
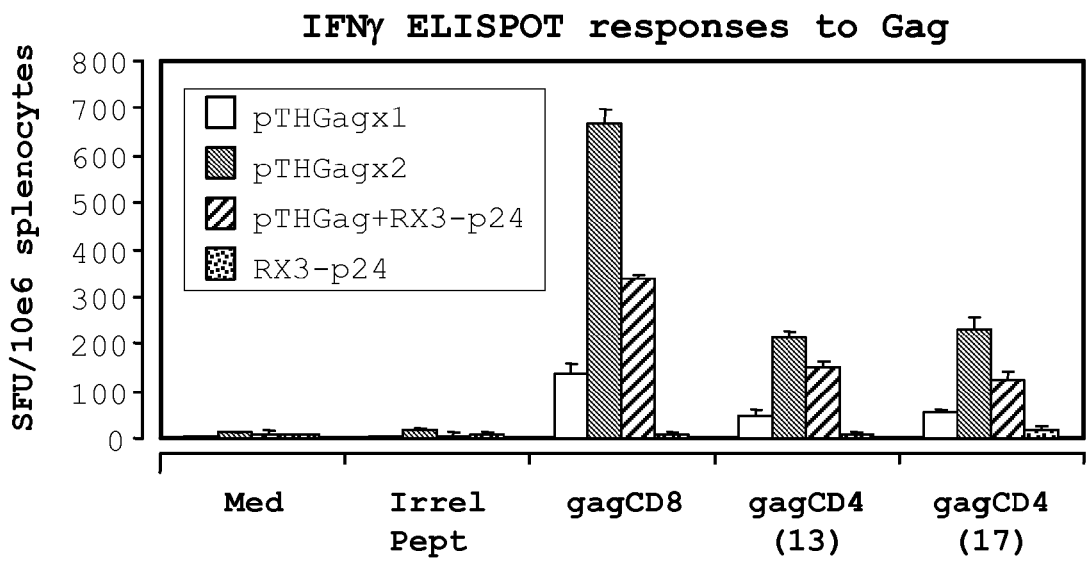
FIG. 2 contains two graphs that show an IFN-γ (FIG. 2A) and IL-2 (FIG. 2B) ELISPOT analysis of p24 cell responses after vaccination of BALB/c mice. Inoculations with the indicated immunogens were given as specified in the methods. Reactions in the corresponding ELISPOT assay were done in triplicate with the indicated Gag peptides, an irrelevant peptide (Irrel pept) or absence of peptide (Med), and bars are the average number of spot forming units (sfu)±SD/ 106 splenocytes. Data are from a representative study with splenocytes pooled from 5 mice per group.
Figure 2B:
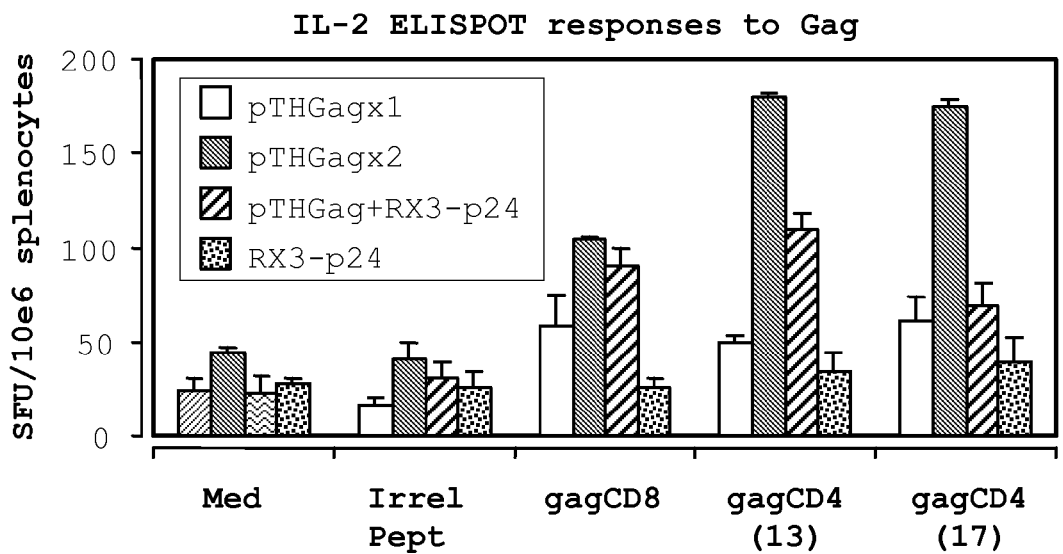

IFN-γ and IL-2 ELISPOT assays indicated that mice inoculated with the DNA vaccine alone (pTHGagx1) induced a cellular response. As shown in FIG. 2, CD4 as well as CD8 T-cells secreted a larger amount of IFN-γ and IL-2 when they were incubated with the stimulating peptides gag CD8, gag CD4(13) or gag CD4(17), compared to T-cells incubated with unrelated peptide. As expected and has been shown previously, the mouse group boosted with a second inoculation of the DNA vaccine (pTHGagx2) showed an even larger cellular response (4-fold compared to the pTH-Gag group).

When the same assays were performed with the mouse group inoculated exclusively with the RPBLAs containing RX3-p24 (RX3-p24), no significant response was observed. This result suggested that the immunogen aggregated inside RPBLAs is not able to trigger the cellular response. Nevertheless, when IFN-γ and IL-2 ELISPOT assays were performed on T-cells from mice inoculated with the DNA vaccine and boosted with a second inoculation consisting of RPBLAs containing RX3-p24 and no further DNA (pTH-Gag+RX3-p24), a surprising 3-fold higher cellular response was observed compared to the pTHGagx1 group. The lack of cellular response observed in the p24 mouse group probably indicates that a higher amount of RPBLAs should be inoculated.

These data indicate that RPBLAs are a suitable immunogen presentation vehicle able to induce a cellular response.

Example 7

Determination of the Humoral Response Triggered by the Intramuscular Inoculation of RX3-p24

It has been shown that the risk of AIDS is greatly increased in individuals with falling titres of p24 antibodies, suggesting that high anti-p24 antibody titres might be necessary to maintain a disease-free state.

Figure 3:
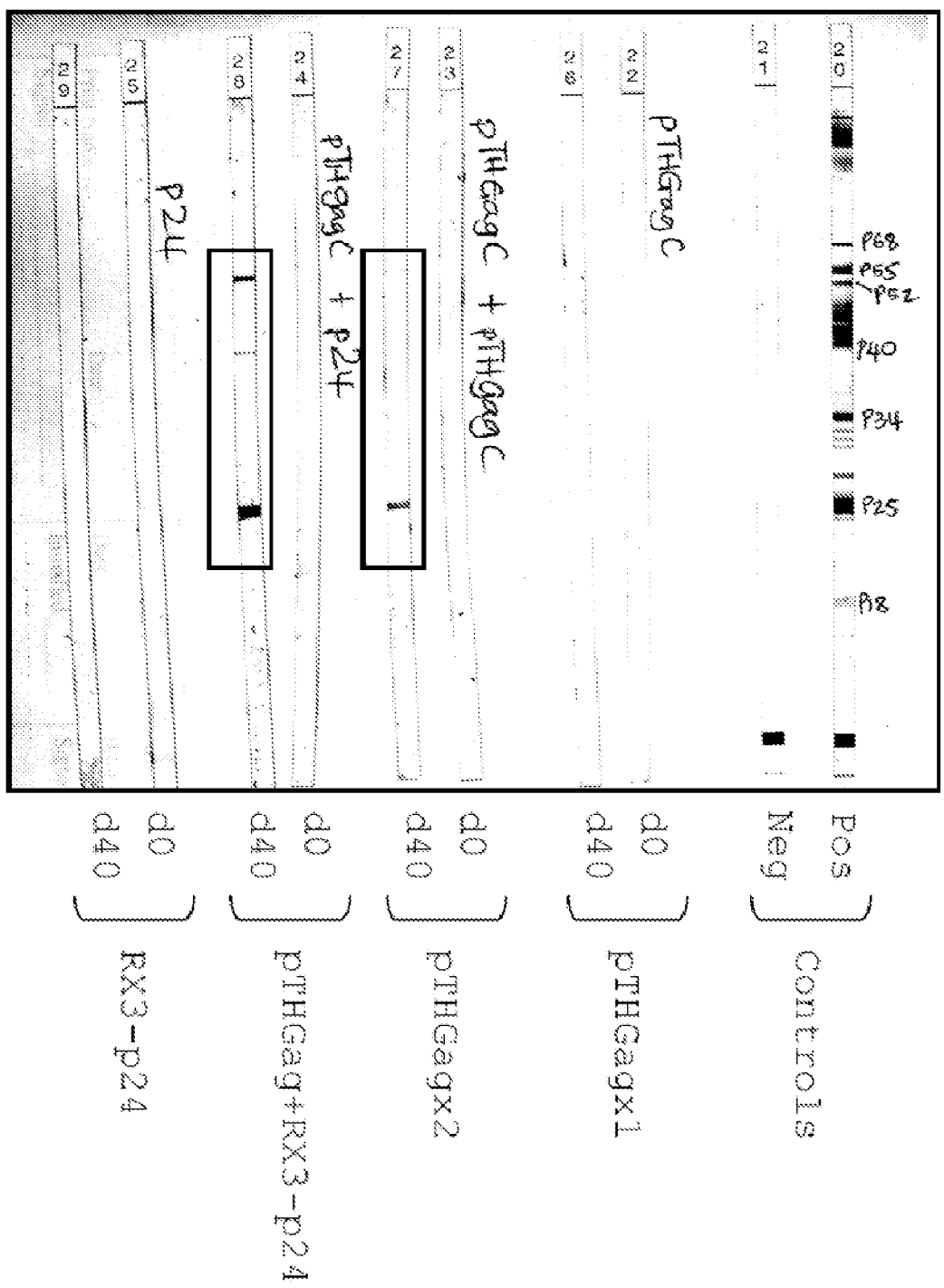
FIG. 3 shows western blot detection of anti-Gag antibodies in mouse serum. The content of anti-Gag antibody in mouse serum was detected using commercial western blot strips as described in the methods. Pos, positive control serum; Neg, negative control serum; d40, mouse serum taken at day 40 after inoculation as indicated and described in methods; d0, pre-inoculation mouse serum. The inoculation regimen for each set of strips is indicated on the right of the strips: these were (i) single gag DNA inoculation (pTHGagx1), (ii) gag DNA prime-gag DNA boost (pTHGagx2), (iii) gag DNA prime—RX3-p24 boost (pTHGagC+RX3-p24), (iv) single RX3-p24 inoculation (RX3-p24).

To determine the presence of antibodies against the p24 antigen, strips containing a representation of the HIV virus proteins [LAV Blot I commercial kit (Biorad)] were incubated with mouse serum from the four inoculation groups (pTHGagx1, pTHGagx2, pTHGag+RX3-p24 and RX3-p24). Antibodies against the p24 protein were detected only in mice inoculated with the DNA vaccine and boosted with a second round of the DNA inoculation or with RPBLAs containing the RX3-p24 and no further DNA (FIG. 3; pTHGagx2 and pTHGag+RX3-p24 mouse groups). Interestingly, the antibodies generated from this second group recognized the full length Gag protein (p55) in addition to the p24 protein indicating that a higher titer of antibodies is produced in pTHGag+RX3-p24 mouse group compared to the pTHGagx1 one.

Example 8

Determination of the Cellular Response Triggered by the Intramuscular Inoculation of RX3-p41

As indicated previously, p41 which results from the fusion of p17 and p24 fragments (p17/24) of the HIV Gag protein, contains the highest density of CTL epitopes in the HIV-1 genome (Novitsky et al., J. Virol. 2002 76(20):10155-10168). In this context the efficiency of RPBLAs containing the RX3-p41 fusion protein to trigger the cellular response of the immune system was examined.

Figure 4A:
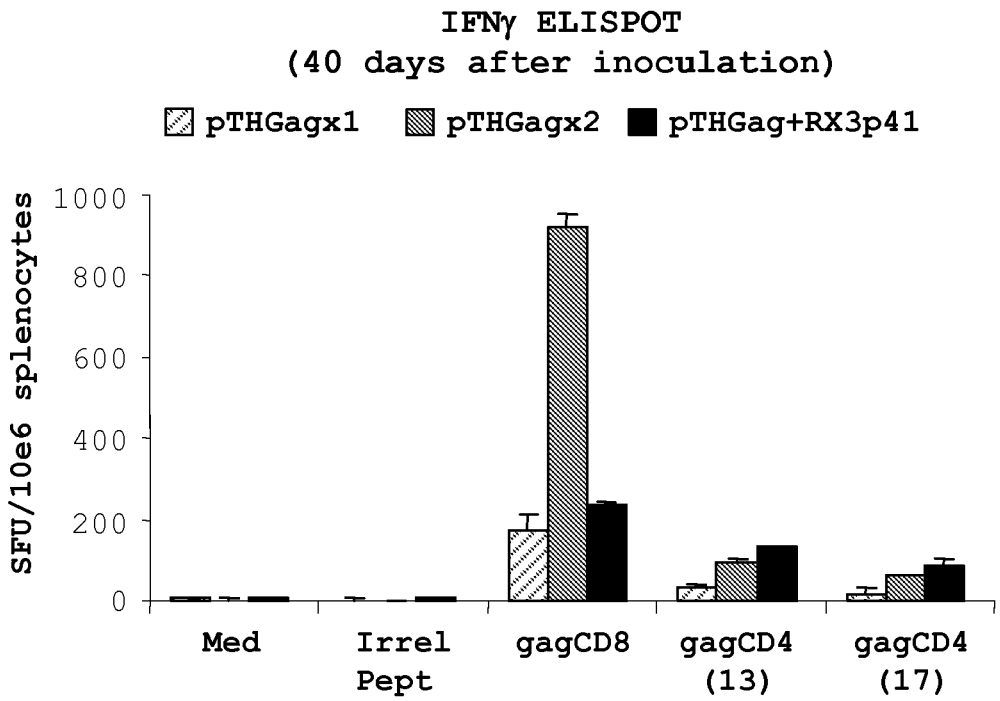
FIG. 4 contains two graphs that show an IFN-γ (FIG. 4A) and IL-2 (FIG. 4B) ELISPOT analysis of p41 cell responses after vaccination of BALB/c mice. Inoculations with the indicated immunogens were given as specified in the methods. Reactions in the corresponding ELISPOT assay were done in triplicate with the indicated Gag peptides, an irrelevant peptide TYSTVASSL (SEQ ID NO:1; irrel pept) or absence of peptide (Med) and bars are the average number of spot forming units (sfu)±SD/106 splenocytes. Data are from a representative study with splenocytes pooled from 5 mice per group.
Figure 4B:
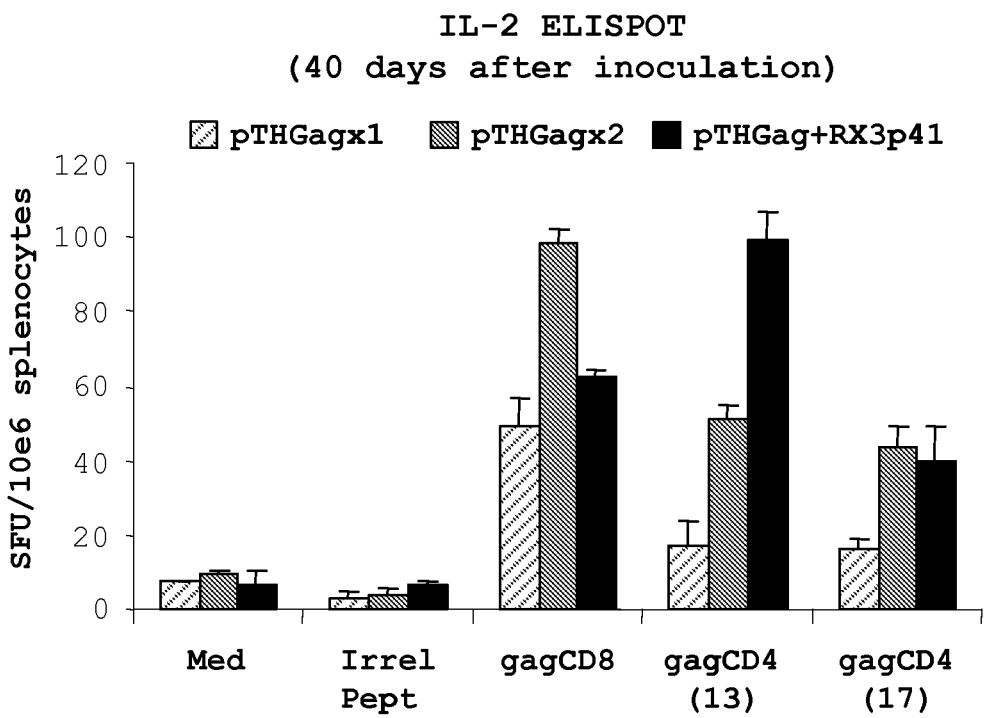

As occurred previously in Example 6, IFN-γ and IL-2 ELISPOT assays indicated that mice inoculated with a single dose of the DNA vaccine induced a small cellular response, which was significantly increased when those mice were boosted with a second inoculation with the DNA vaccine (compare pTHGagx1 versus pTHGagx2 in FIG. 4). It is interesting to point out that splenocytes from the mouse group boosted with the RX3-p41 (pTHGag+RX3-p41) secreted an even larger amount of IFNγ and IL-2 than the pTHGagx2 group when they were incubated with the gagCD4(13) and gagCD4(17) stimulating peptides (FIG. 4). Although the secretion of IFNγ and IL-2 was not increased by the incubation of splenocytes from the pTHGag+RX3-p41 mouse group with gagCD8-stimulating peptides, it can be concluded that the cellular response of the immune system is efficiently boosted by the inoculation of RPBLAs containing RX3-p41 fusion protein.

Example 9

Determination of the Cellular Response Triggered by Intramuscular Inoculation of RX3-RT As an effective multivalent vaccine against HIV includes several antigens, similar studies were performed with HIV viral protein RT.

Figure 5A:
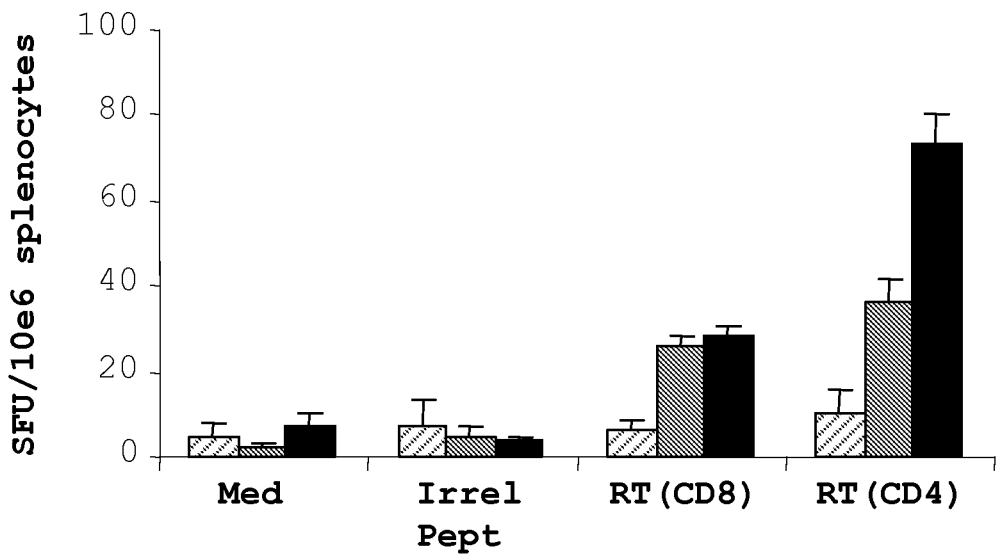
FIG. 5 contains two graphs that show an IL-2 (FIG. 5A) and IFN-γ (FIG. 5B) ELISPOT analysis of RT cell responses after vaccination of BALB/c mice. Inoculations with the indicated immunogens were given as specified in the methods. Reactions in the corresponding ELISPOT assay were done in triplicate with the indicated Gag peptides, an irrelevant peptide TYSTVASSL (SEQ ID NO:1; irrel pept) or absence of peptide (Med) and bars are the average number of spot forming units (sfu)±SD/106 splenocytes. Data are from a representative study with splenocytes pooled from 5 mice per group.
Figure 5B:
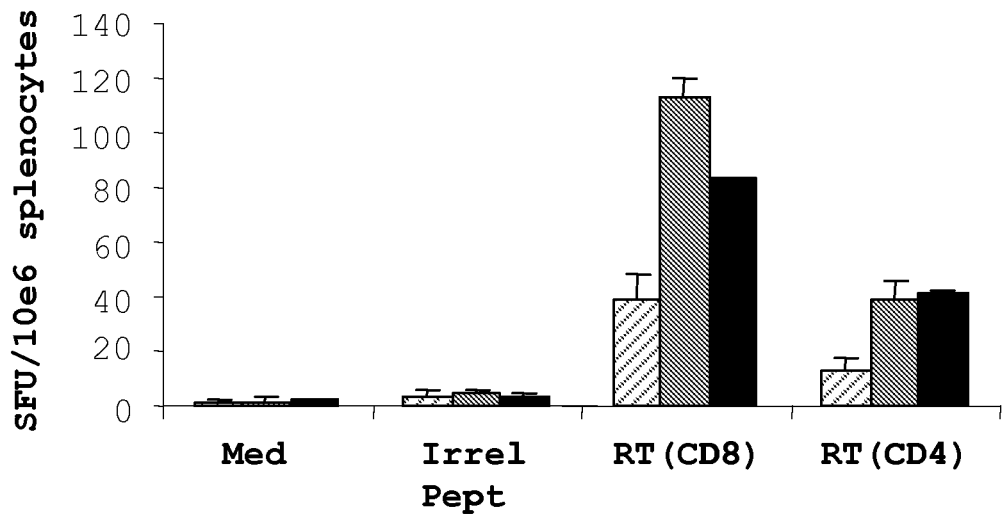

IFNγ ELISPOT assays indicated that mice inoculated with a single dose of the DNA vaccine (pVRCgrttnx1) induced a very poor cellular response. Exclusively CD8 T-cells incubated with the stimulating peptides RT(CD8) secreted a larger amount of IFN-γ than the same cells incubated with un irrelevant peptide TYSTVASSL (SEQ ID NO:1; FIG. 5). A boost with a second inoculation of the DNA vaccine (pVRCgrttnx2) or the RPBLAs containing RX3—RT (pVRCgrttn+RX3-RT) was needed to observe a general induction of the cellular response. FIG. 5 shows that CD4 and CD8 T-cells incubated with the corresponding stimulating peptides secreted a larger amount of IFN-γ and IL-2 compared to the control treatments (absence or presence of an irrelevant peptide).

Example 10

Determination of the Immune Response Triggered by the Intramuscular Inoculation of a DNA Vaccine Expressing RX3-p24, RX3-41 or RX3-RT DNA vaccines encoding HIV antigens have been studied extensively and shown to induce both humoral and cellular immune responses in animal models as well as in humans (Estcourt et al., *Immunol. Rev.* 2004 199:144-155). However, although DNA vaccines have been shown to be safe, immunizations have generated low and transient levels of immune responses.

pTHGag was shown in the mouse model to induce a potent cytotoxic lymphocyte response. Pr55Gag expressed in a variety of cell systems can assemble and bud through the plasma membrane to form highly immunogenic virus-like particles (VLPs). RPBLAs can not been considered as classical VLPs, because their assembly is induced by the aggregation capacity of RX3, which is not a viral protein involved in the formation of the virus particles. However, the suitability of a DNA vaccine expressing RPBLAs containing the RX3-24, RX3-41, RX3-RT and RX3E7SH was examined. Interestingly, once the corresponding pTH-derived vectors (pTHRX3-p24, pTHRX3-p41, pTHRX3-RT and pTHRX3-E7SH) were administered as the pTHGag in previous studies, significant humoral and cellular immune responses were observed. This unexpected result indicates that RPBLAs can be administered by DNA vaccination; in spite of this organelles are stored in the ER and are not supposed to bud through the plasma membrane to form highly immunogenic virus-like particles (VLPs).

Example 11

Determination of the Immune Response Triggered by the Inoculation of RPBLAs Assembled In Vitro The isolation of RPBLAs by density gradient permits the recovery of a highly enriched fraction of RPBLAs, but a certain degree of contaminants are co-purified. To remove as much contaminants as possible, the RX3 fusion proteins (RX3-p24, RX3-p41, RX3-RT and RX3-E7SH) were solubilized from the corresponding RPBLA fraction in 20 mM Tris pH8, 2% DOC, 10 mM DTT incubated 1 hour at room temperature in soft agitation, and purified in RP-FPLC. The elution fractions containing the RX3 fusion proteins with more than 95% purity were pooled and lyophilized. The corresponding pellet was recovered in distilled water in the presence of 200 mM of NaCl and 50 mM of CaCl. In these conditions, the fusion proteins containing the RX3 peptide reassemble spontaneously to reform RPBLAs in vitro, outside of the plant ER.

In vitro-assembled RPBLAs containing the corresponding RX3 fusion protein were inoculated into mice and the IFNγ, IL-2 and Granzyme B ELISPOT assays showed that RPBLAs boost significantly the cellular response in equivalent studies as the those performed using in vivo-formed RPBLAs. This surprising result indicates that in vitro-assembled RPBLAs maintain the capacity of inducing the cellular response.

RX3 fusion proteins can be induced to assemble in vitro and form RPBLAs in the following conditions: (i) reducing the pH value of the solution, (ii) increasing salt content, (iii) reducing or removing the concentration of reducing agents, (iv) adding oxidizing agents, (v) decreasing the temperature, or a combination of this factors. Obviously, in vitro RPBLAs are not surrounded by a membrane. Preferred salts to induce the assembly in vitro are NaCl, CaCl and KCl and preferred pH values are below 7.

As indicated before, a double immune response (cellular plus humoral) produces a more protective effect against AIDS. The presence of antibodies against the p24, p41 and RT antigens was shown by using the HIV strips (LAV Blot I commercial kit (Biorad)) in mice primed with the DNA vaccine and boosted with the corresponding in vitro assembled RPBLAs.

Example 12

Isolation (Purification) of RPBLAs Containing RX3-E7SH by Density Gradient from Agroinfiltrated Tobacco Leaves Approximately 10 g of leaf tissue agroinfiltrated with the HPV-16 antigen E7SH fused to RX3 (pRX3-E7SH) was ground up in liquid nitrogen and resuspended in 20 ml of buffer PBP3 (100 mM Tris pH8, 50 mM KCl, 6 mM $MgCl_2$, 10 mM EDTA and 0.4M NaCl). This was homogenized for 3 minutes on ice using a Polytron homogenizer and then filtered through miracloth. The corresponding filtrate was loaded on top of a density step gradient, comprising of 7 ml volumes of 15, 25, 35 and 45% concentrations of Optiprep® density gradient medium made up in buffer PBP3. The gradient was centrifuged for 2 hours at 80,000×g in a Beckman SW28 rotor at 4° C. The pellet was resuspended in 500 µl buffer PBP3 to check for the presence of RPBLAs by optic microscopy, and an aliquot stored for analysis. The remainder was stored at −70° C.

The gene sequence for the RX2-E7SH fusion protein is shown below from 5' to 3':

SEQ ID NO: 129
ATGAGGGTGTTGCTCGTTGCCCTCGCTCTCCTGGCTCTCGCTGCGAGC

GCCACCTCCACGCATACAAGCGGCGGCTGCGGCTGCCAGCCACCGCCG

CCGGTTCATCTACCGCCGCCGGTGCATCTGCCACCTCCGGTTCACCTG

CCACCTCCGGTGCATCTCCCACCGCCGGTCCACCTGCCGCCGCCGGTC

CACCTGCCACCGCCGGTCCATGTGCCGCCGCCGGTTCATCTGCCGCCG

CCACCATGCCACTACCCTACTCAACCGCCCCGGCCTCAGCCTCATCCC

CAGCCACACCCATGCCCGTGCCAACAGCCGCATCCAAGCCCGTGCCAG

ACCATGGACGACGATGATAAGATGCACGGCGACACCCCCACCCTGCAC

GAGTACATGCTGGACCTGCAGCCCGAGACCACCGACCTGTACTGCATC

TGCAGCCAGAAACCCAAGTGCGACAGCACCCTGCGGCTGTGCGTGCAG

AGCACCCACGTGGACATCCGGACCCTGGAGGACCTGCTGATGGGCACC

CTGGGCATCGTGTGCCCCTACGAGCAGCTGAACGACAGCAGCGAGGAG

GAGGATGAGATCGACGGCCCCGCCGGCCAGGCTGAGCCCGACCGGGCC

CACTACAACATCGTGACCTTCTGCTGCCAACCAGAGACAACTGATCTC

TACTGTTATGAGCAATTAAATGACAGCTCAGAGCATTACAATATTGTA

ACCTTTTGTTGCAAGTGTGACTCTACGCTTCGGTTGTGCATGGGCACA

CTAGGAATTGTGTGCCCCATCTGTTCTCAGAAACCATAA

Figure 7:
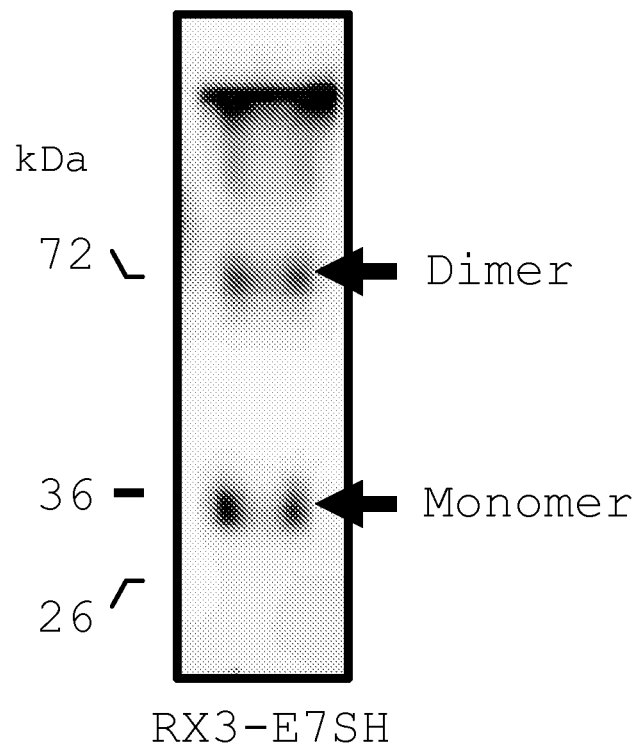
FIG. 7 shows the analysis by western blot of RPBLA fractions isolated from tobacco plants agroinfiltrated with RX3-E7SH. The presence of full length RX3 fusion proteins in the corresponding RPBLA fraction preparation was checked by using E7SH antibody.

To verify that the RPBLAs fraction contained the corresponding RX3 fusion protein, an aliquot of it was analyzed by western blot using anti-RX3 to verify the integrity of the fusion protein (FIG. 7).

Example 13

Determination of the Cellular Response Triggered by the Inoculation of RX3-E7SH

To determine the cellular immune response induced by the administration of RX3-E7SH containing RPBLAs, five groups of mice were inoculated as follows: (i) mice inoculated with the DNA vaccine expressing E7SH antigen (pTHamp-E7SH), (ii) mice inoculated with the corresponding DNA vaccine negative control (pTHamp) with the sequence:

SEQ ID NO: 127
5'GACGGATCGGGAGATCTCCCGATCCCCTATGGTCGACTCTCAGTAC

AATCTGCTCTGATGCCGCATAGTTAAGCCAGTATCTGCTCCCTGCTTG

TGTGTTGGAGGTCGCTGAGTAGTGCGCGAGCAAAATTTAAGCTACAAC

AAGGCAAGGCTTGACCGACAATTGCATGAAGAATCTGCTTAGGGTTAG

GCGTTTTGCGCTGCTTCGCGATGTACGGGCCAGATATACGCGTTTTGA

GATTTCTGTCGCCGACTAAATTCATGTCGCGCGATAGTGGTGTTTATC

GCCGATAGAGATGGCGATATTGGAAAAATCGATATTTGAAAATATGGC

ATATTGAAAATGTCGCCGATGTGAGTTTCTGTGTAACTGATATCGCCA

TTTTTCCAAAAGTGATTTTTGGGCATACGCGATATCTGGCGATAGCGC

TTATATCGTTTACGGGGGATGGCGATAGACGACTTTGGTGACTTGGGC

GATTCTGTGTGTCGCAAATATCGCAGTTTCGATATAGGTGACAGACGA

TATGAGGCTATATCGCCGATAGAGGCGACATCAAGCTGGCACATGGCC

AATGCATATCGATCTATACATTGAATCAATATTGGCCATTAGCCATAT

TATTCATTGGTTATATAGCATAAATCAATATTGGCTATTGGCCATTGC

ATACGTTGTATCCATATCATAATATGTACATTTATATTGGCTCATGTC

CAACATTACCGCCATGTTGACATTGATTATTGACTAGTTATTAATAGT

AATCAATTACGGGGTCATTAGTTCATAGCCCATATATGGAGTTCCGCG

TTACATAACTTACGGTAAATGGCCCGCCTGGCTGACCGCCCAACGACC

CCCGCCCATTGACGTCAATAATGACGTATGTTCCCATAGTAACGCCAA

TAGGGACTTTCCATTGACGTCAATGGGTGGAGTATTTACGGTAAACTG

CCCACTTGGCAGTACATCAAGTGTATCATATGCCAAGTACGCCCCCTA

TTGACGTCAATGACGGTAAATGGCCCGCCTGGCATTATGCCCAGTACA

TGACCTTATGGGACTTTCCTACTTGGCAGTACATCTACGTATTAGTCA

TCGCTATTACCATGGTGATGCGGTTTTGGCAGTACATCAATGGGCGTG

GATAGCGGTTTGACTCACGGGGATTTCCAAGTCTCCACCCCATTGACG

TCAATGGGAGTTTGTTTTGGCACCAAAATCAACGGGACTTTCCAAAAT

GTCGTAACAACTCCGCCCCATTGACGCAAATGGGCGGTAGGCGTGTAC

GGTGGGAGGTCTATATAAGCAGAGCTCGTTTAGTGAACCGTCAGATCG

CCTGGAGACGCCATCCACGCTGTTTTGACCTCCATAGAAGACACCGGG

ACCGATCCAGCCTCCGCGGCCGGGAACGGTGCATTGGAACGCGGATTC

CCCGTGCCAAGAGTGACGTAAGTACCGCCTATAGAGTCTATAGGCCCA

CCCCCTTGGCTTCTTATGCATGCTATACTGTTTTTGGCTTGGGGTCTA

TACACCCCGCTTCCTCATGTTATAGGTGATGGTATAGCTTAGCCTAT

AGGTGTGGGTTATTGACCATTATTGACCACTCCCCTATTGGTGACGAT

ACTTTCCATTACTAATCCATAACATGGCTCTTTGCCACAACTCTCTTT

ATTGGCTATATGCCAATACACTGTCCTTCAGAGACTGACACGGACTCT

GTATTTTTACAGGATGGGGTCTCATTTATTATTTACAAATTCACATAT

ACAACACCACCGTCCCCAGTGCCCGCAGTTTTTATTAAACATAACGTG

GGATCTCCACGCGAATCTCGGGTACGTGTTCCGGACATGGGCTCTTCT

CCGGTAGCGGCGGAGCTTCTACATCCGAGCCCTGCTCCCATGCCTCCA

GCGACTCATGGTCGCTCGGCAGCTCCTTGCTCCTAACAGTGGAGGCCA

GACTTAGGCACAGCACGATGCCCACCACCACCAGTGTGCCGCACAAGG

CCGTGGCGGTAGGGTATGTGTCTGAAAATGAGCTCGGGGAGCGGGCTT

GCACCGCTGACGCATTTGGAAGACTTAAGGCAGCGGCAGAAGAAGATG

CAGGCAGCTGAGTTGTTGTGTTCTGATAAGAGTCAGAGGTAACTCCCG

TTGCGGTGCTGTTAACGGTGGAGGGCAGTGTAGTCTGAGCAGTACTCG

TTGCTGCCGCGCGCCACCAGACATAATAGCTGACAGACTAACAGAC

TGTTCCTTTCCATGGGTCTTTTCTGCAGTCACCGTCCTTGACACGAAG

-continued
```
CTTGGTACCGAGCTCGGATCCACTAGTAACGGCCGCCAGTGTGCTGGA
ATTCTGCAGATATCCATCACACTGGCGGCCGCTCGAGCATGCATCTAG
AGGGCCCTATTCTATAGTGTCACCTAAATGCTAGAGCTCGCTGATCAG
CCTCGACTGTGCCTTCTAGTTGCCAGCCATCTGTTGTTTGCCCCTCCC
CCGTGCCTTCCTTGACCCTGGAAGGTGCCACTCCCACTGTCCTTTCCT
AATAAAATGAGGAAATTGCATCGCATTGTCTGAGTAGGTGTCATTCTA
TTCTGGGGGTGGGGTGGGGCAGGACAGCAAGGGGGAGGATTGGGAAG
ACAATAGCAGGCATGCTGGGGATGCGGTGGGCTCTATGGCTTCTGAGG
CGGAAAGAACCAGCTGGGGCTCGAGGGGGGATCGATCCCGTCGACCTC
GAGAGCTTGGCGTAATCATGGTCATAGCTGTTTCCTGTGTGAAATTGT
TATCCGCTCACAATTCCACACAACATACGAGCCGGAAGCATAAAGTGT
AAAGCCTGGGGTGCCTAATGAGTGAGCTAACTCACATTAATTGCGTTG
CGCTCACTGCCCGCTTTCCAGTCGGGAAACCTGTCGTGCCAGCTGCAT
TAATGAATCGGCCAACGCGCGGGGAGAGGCGGTTTGCGTATTGGGCGC
TCTTCCGCTTCCTCGCTCACTGACTCGCTGCGCTCGGTCGTTCGGCTG
CGGCGAGCGGTATCAGCTCACTCAAAGGCGGTAATACGGTTATCCACA
GAATCAGGGGATAACGCAGGAAAGAACATGTGAGCAAAAGGCCAGCAA
AAGGCCAGGAACCGTAAAAAGGCCGCGTTGCTGGCGTTTTTCCATAGG
CTCCGCCCCCTGACGAGCATCACAAAAATCGACGCTCAAGTCAGAGG
TGGCGAAACCCGACAGGACTATAAAGATACCAGGCGTTTCCCCCTGGA
AGCTCCCTCGTGCGCTCTCCTGTTCCGACCCTGCCGCTTACCGGATAC
CTGTCCGCCTTTCTCCCTTCGGGAAGCGTGGCGCTTTCTCAATGCTCA
CGCTGTAGGTATCTCAGTTCGGTGTAGGTCGTTCGCTCCAAGCTGGGC
TGTGTGCACGAACCCCCCGTTCAGCCCGACCGCTGCGCCTTATCCGGT
AACTATCGTCTTGAGTCCAACCCGGTAAGACACGACTTATCGCCACTG
GCAGCAGCCACTGGTAACAGGATTAGCAGAGCGAGGTATGTAGGCGGT
GCTACAGAGTTCTTGAAGTGGTGGCCTAACTACGGCTACACTAGAAGG
ACAGTATTTGGTATCTGCGCTCTGCTGAAGCCAGTTACCTTCGGAAAA
AGAGTTGGTAGCTCTTGATCCGGCAAACAAACCACCGCTGGTAGCGGT
GGTTTTTTTGTTTGCAAGCAGCAGATTACGCGCAGAAAAAAAGGATCT
CAAGAAGATCCTTTGATCTTTTCTACGGGGTCTGACGCTCAGTGGAAC
GAAAACTCACGTTAAGGGATTTTGGTCATGAGATTATCAAAAAGGATC
TTCACCTAGATCCTTTTAAATTAAAAATGAAGTTTTAAATCAATCTAA
AGTATATATGAGTAAACTTGGTCTGACAGTTACCAATGCTTAATCAGT
GAGGCACCTATCTCAGCGATCTGTCTATTTCGTTCATCCATAGTTGCC
TGACTCCCCGTCGTGTAGATAACTACGATACGGGAGGGCTTACCATCT
GGCCCCAGTGCTGCAATGATACCGCGAGACCCACGCTCACCGGCTCCA
GATTTATCAGCAATAAACCAGCCAGCCGGAAGGGCCGAGCGCAGAAGT
GGTCCTGCAACTTTATCCGCCTCCATCCAGTCTATTAATTGTTGCCGG
GAAGCTAGAGTAAGTAGTTCGCCAGTTAATAGTTTGCGCAACGTTGTT
GCCATTGCTACAGGCATCGTGGTGTCACGCTCGTCGTTTGGTATGGCT
TCATTCAGCTCCGGTTCCCAACGATCAAGGCGAGTTACATGATCCCCC
ATGTTGTGCAAAAAAGCGGTTAGCTCCTTCGGTCCTCCGATCGTTGTC
AGAAGTAAGTTGGCCGCAGTGTTATCACTCATGGTTATGGCAGCACTG
CATAATTCTCTTACTGTCATGCCATCCGTAAGATGCTTTTCTGTGACT
GGTGAGTACTCAACCAAGTCATTCTGAGAATAGTGTATGCGGCGACCG
AGTTGCTCTTGCCCGGCGTCAATACGGGATAATACCGCGCCACATAGC
AGAACTTTAAAAGTGCTCATCATTGGAAAACGTTCTTCGGGGCGAAAA
CTCTCAAGGATCTTACCGCTGTTGAGATCCAGTTCGATGTAACCCACT
CGTGCACCCAACTGATCTTCAGCATCTTTTACTTTCACCAGCGTTTCT
GGGTGAGCAAAACAGGAAGGCAAAATGCCGCAAAAAAGGGAATAAGG
GCGACACGGAAATGTTGAATACTCATACTCTTCCTTTTTCAATATTAT
TGAAGCATTTATCAGGGTTATTGTCTCATGAGCGGATACATATTTGAA
TGTATTTAGAAAAATAAACAAATAGGGGTTCCGCGCACATTTCCCCGA
AAAGTGCCACCTGACGTC3'
```

(iii) mice inoculated with RPBLAs containing RX3-E7SH (RX3-E7SH), (iv) mice co-inoculated with RPBLAs containing RX3-E7SH and incomplete Freund's adjuvant (RX3-E7SH/IFA), and finally (v) mice inoculated with RPBLAs containing RX3 fused to Gfp (RX3-Gfp) as a negative control of RPBLAs.

Figure 8A:
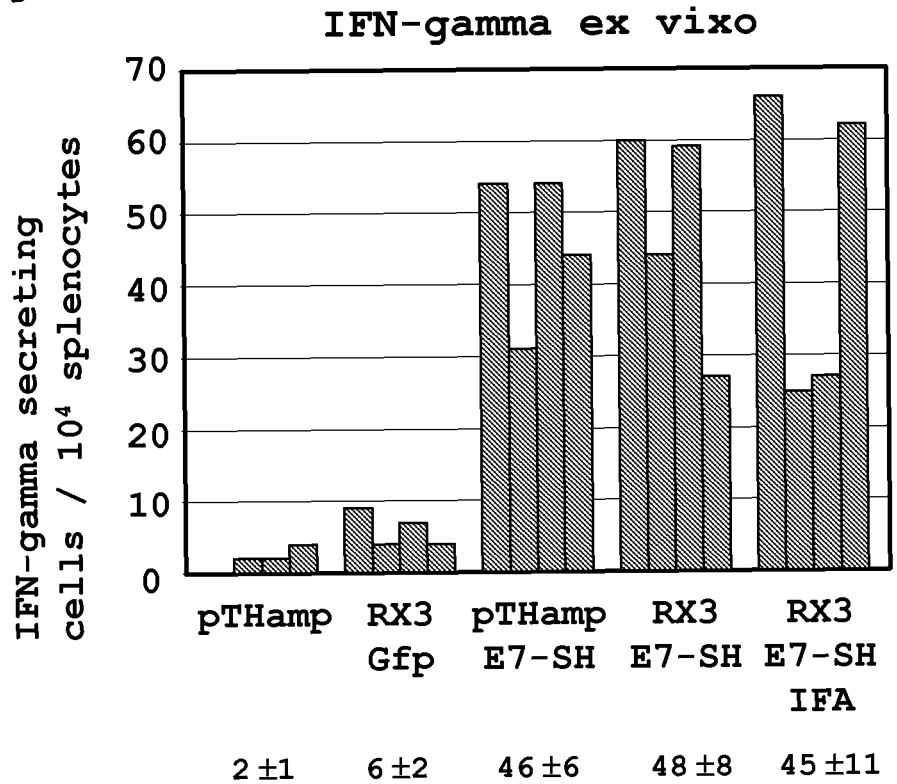
FIG. 8 contains two graphs (FIG. 8A and FIG. 8B) that illustrate CTL responses in C57BL/6 mice after DNA and RPBLAs immunization. Four mice per group were immunized once intra-muscularly in each musculus tibialis anterior with: (i) 50 μg empty plasmid (pTHamp), (ii) 50 μg plasmid expressing E7SH (pTHamp-E7SH), (iii) or subcutaneously into the flank with 5 μg of RPBLAs containing RX3-Gfp fusion protein (RX3-Gfp), (iv) 5 μg of RPBLAs containing RX3-E7SH fusion protein (RX3-E7SH) or (v) 5 μg of RPBLAs containing RX3-E7SH fusion protein and 100 μl of IFA (5 μg RX3-E7SH in 100 μl buffer+100 μl IFA). Ex vivo IFN-γ and Granzyme B Elispot assays were performed and each bar represents the number of activated T cells from an individual animal.
Figure 8B:
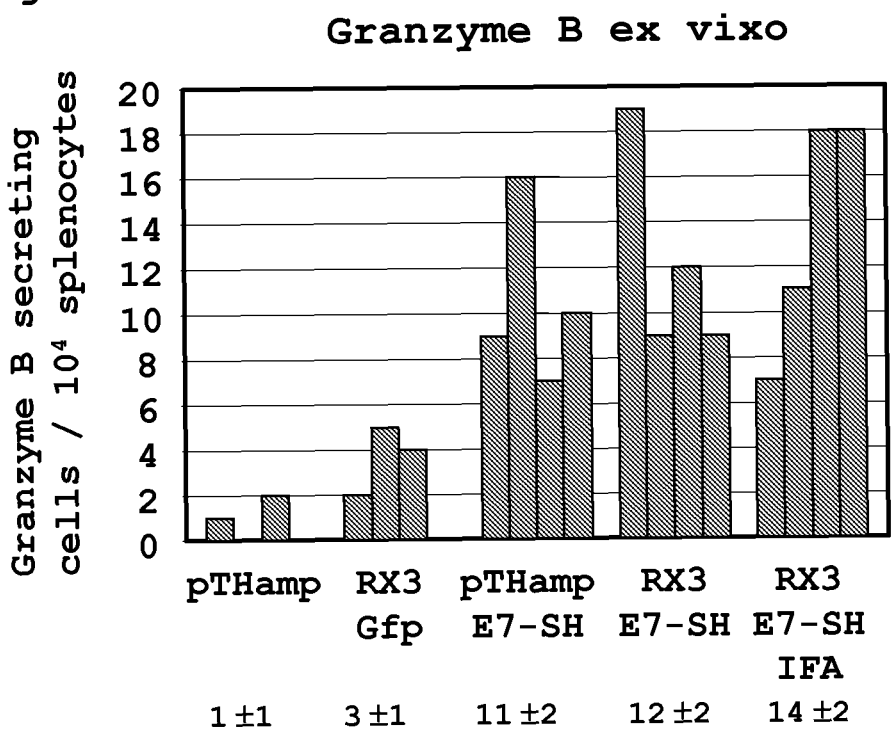

As expected, IFN-γ and Granzyme B ELISPOT assays indicated clearly that mice inoculated with the DNA vaccine (pTHamp-E7SH) induced a cellular response. As shown in FIG. 8, splenocyte cells coming from mice inoculated with the pTHamp-E7SH DNA vaccine secreted a significant larger amount of IFN-γ and Granzyme B, than the ones coming from mice inoculated with the DNA vaccine in the absence of E7SH antigen (pTHamp).

Surprisingly, it was also observed that splenocytes isolated from mice inoculated with RPBLAs containing RX3-E7SH(RX3-E7SH) also released a large amount of IFN-γ and Granzyme B (equivalent to pTHamp-E7SH mice group) in the presence or absence of IFA co-administration FIG. 8. As a control, the negative results observed in RX3-Gfp group indicate that no unspecific cellular response against E7SH is triggered by the administration of RPBLAs.

Figure 9:
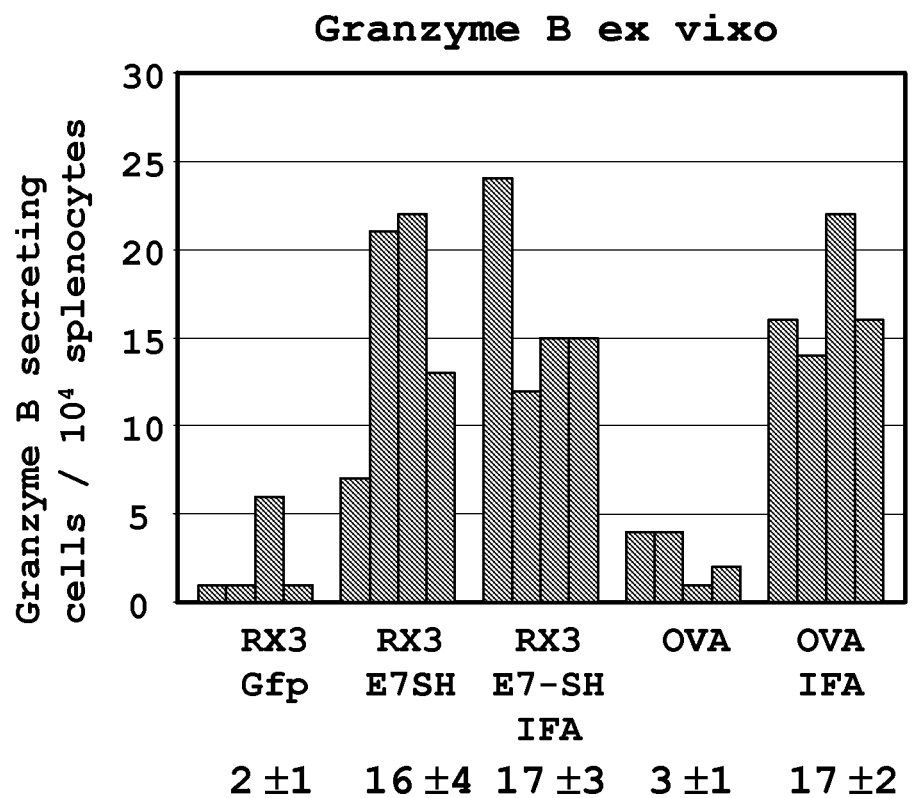
FIG. 9 is a graph of CTL responses in C57BL/6 mice after RPBLAs immunization. Four mice per group were immunized once intramuscularly or sc (as above) with: (i) 5 μg of RPBLAs containing RX3-Gfp fusion protein (RX3-Gfp), (ii) 5 μg of RPBLAs containing RX3-E7SH fusion protein (RX3-E7SH), (iii) 5 μg of RPBLAs containing RX3-E7SH fusion protein and 100 μl of IFA (RX3-E7SH/IFA), (iv) 5 μg of ovalbumin (OVA) or (v) 5 μg of ovalbumin and 100 μl of IFA (OVA/IFA) in each musculus tibialis anterior. Ex vivo Granzyme B Elispot assays were performed and each bar represents the number of activated T cells from an individual animal.

These results demonstrate clearly that E7SH antigen administered in fusion with RX3 in a RPBLAs particle is able to trigger efficiently a cellular response. The fact that no adjuvant was needed to achieve the maximum effect indicates that RX3-E7SH in RPBLAs is an efficient antigen presentation vehicle able to induce a cellular response. This conclusion was supported by the observation that it is necessary to co-administer IFA to ovalbumin (OVA) in order to induce an efficient cellular response FIG. 9.

The amino acid sequence for ovalbumin in single letter code is shown below:

```
MGSIGAASME FCFDVFKELK VHHANENIFY CPIAIMSALA
MVYLGAKDST RTQINKVVRF DKLPGFGDSI EAQCGTSVNV
HSSLRDILNQ ITKPNDVYSF SLASRLYAEE RYPILPEYLQ
CVKELYRGGL EPINFQTAAD QARELINSWV ESQTNGIIRN
```

-continued

```
VLQPSSVDSQ TAMVLVNAIV FKGLWEKTFK DEDTQAMPFR

VTEQESKPVQ MMYQIGLFRV ASMASEKMKI LELPFASGTM

SMLVLLPDEV SGLEQLESII NFEKLTEWTS SNVMEERKIK

VYLPRMKMEE KYNLTSVLMA MGITDVFSSS ANLSGISSAE

SLKISQAVHA AHAEINEAGR EVVGSAEAGV DAASVSEEFR

ADHPFLFCIK HIATNAVLFF GRCVSP
```

Example 14

Determination of the Cytolytic Activity of the Splenocytes Induced by the Inoculation of with RX3-E7SH To determine, if the specifically activated splenocytes had cytolytic activity, $^{51}$Cr-release assays were performed. $^{51}$Cr release assays were performed 5-6 days after an in vitro restimulation of murine spleen cells as described elsewhere [Steinberg et al., (2005) *Vaccine* 23(9):1149-1157.] An animal was scored positive when the specific lysis of the specific target (RX3-E7 or pTHamp-E7SH cells) was at least 10% above the lysis of the control target (RX3-Gfp or pTHamp cells) for the protein and DNA based vaccines. After a first round of in vitro restimulation strong specific cytolytic activity against the E7WT-expressing RMA-E7 transfectants was shown (see table below.)

TABLE

| $^{51}$C-release assay (after 1$^{st}$ in vitro restimulation) | Specific Lysis (%) |
|---|---|
| pTHamp | 8 ± 3 |
| pTHamp-E7SH | 12 ± 4 |
| RX3-Gfp | 26 ± 6 |
| RX3-E7SH | 33 ± 5 |
| RX3-E7SH/IFA | 29 ± 6 |

Surprisingly, the mean of specific lysis of the RMA-E7 cells was comparable in the RX3-E7SH-group (33%) and the pTHamp-E7SH immunized animals (26%), and significantly higher than the corresponding control groups RX3-Gfp (12%) and the pTHamp (8%). This result indicates that RX3-E7SH RPBLAs was able to induce a specific cytolytic activity against E7 expressing cells as efficiently as has already been shown by using the DNA vaccine pTHamp-E7SH [Öhlschlager et al., (2006) *Vaccine* 24:2880-2893]. Moreover, the fact that the cytolytic activity was not increased when the RPBLAs containing RX3-E7SH fusion protein was co-administered with IFA (see RX3-E7SH/IFA-group in table) suggests that even a lower dose would be effective to trigger the cytolytic effect, supporting the idea that RPBLAs provide an efficient administration vehicle to trigger a specific cytolytic effect.

It is important to add that it has been widely demonstrated that a cytolytic response is a crucial element for controlling tumor growth [Akazawa, 2004 *Cancer Res* 64:757-764] and viral infection (Vine et al., 2004 *J Immunol* 173:5121-5129].

Example 15

Determination of Tumor Growth in Mice Inoculated with RX3-E7SH

The aim of a therapeutic tumor vaccine is the induction of an effective immune response eradicating established tumors. Therefore, vaccination with the E7SH gene was examined to determine whether a cellular immune response could be induced that was able to control established E7-expressing tumor cells in vivo. In four tumor regression studies, a total of 80 animals were transplanted with a tumorigenic dose of syngeneic C3-tumor cells (day 0). When the tumors had reached a mean size of 4-9 mm$^2$ at days 5-18, the animals were inoculated with: (i) 100 µg of the E7SH-encoding plasmid (pTHamp-E7SH), (ii) 100 µg of empty pTHamp vector (pTHamp), (iii) RPBLAs containing 5 µg of RX3-E7SH(RX3-E7SH), and (iv) the same amount of RX3-E7SH RPBLAs co-administered with IFA (RX3-E7SH/IFA) (day zero). Tumor size was determined every two days by measuring with a ruler until the end of the study (day 14).

Figure 10A:
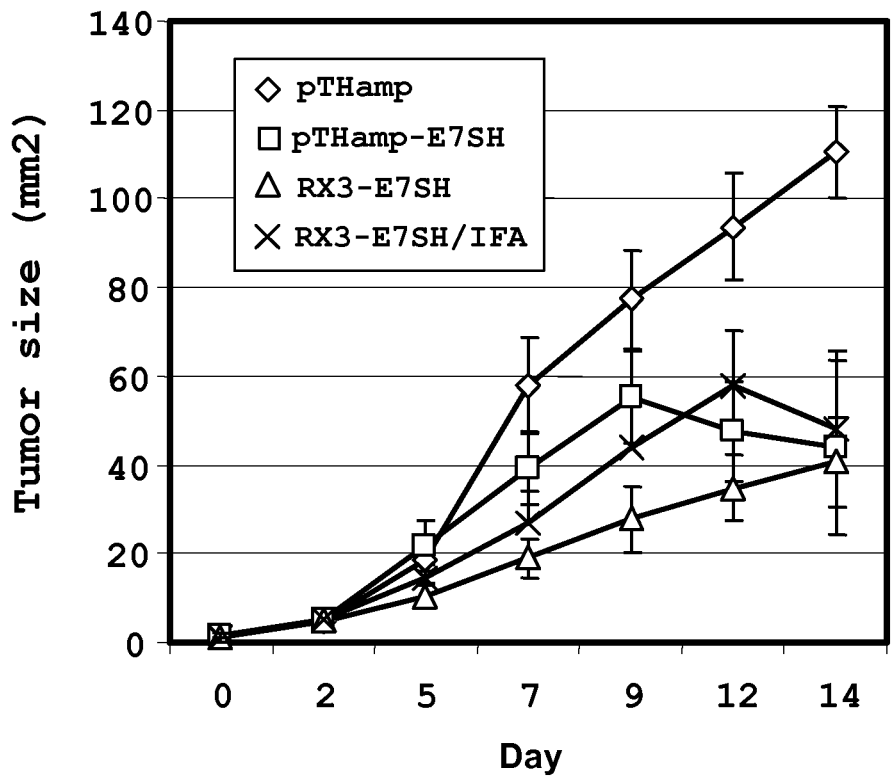

As shown in FIG. 10A, tumor size increased progressively in mice inoculated with the control DNA vector (pTHamp), reaching a maximum average size of 110 mm$^2$ 14 days after inoculation. Tumor growth was significantly reduced in those mice inoculated with RPBLAs containing RX3-E7SH. Through out the study, the RX3-E7SH mice group showed tumors with lower size compared to the control group, reaching a mean value of 40 mm$^2$ at day 14. It is interesting to point out that the protective effect of RX3-E7SH inoculation is comparable to the DNA vaccine pTHamp-E7SH, which has been reported to be a good therapeutic vaccine against E7-expressing tumors [Ohlschlager et al., (2006) *Vaccine* 24:2880-2893]. Moreover, as indicated before, the fact that the co-administration of RPBLAs containing RX3-E7SH with IFA (RX3-E7SH/IFA) did not increase the protective effect of the same amount of RPBLAs containing RX3-E7SH in the absence of an adjuvant (RX3-E7SH) suggests that a lower amount of RX3-E7SH will be protective against E7-expressing tumor growth.

Figure 10B:
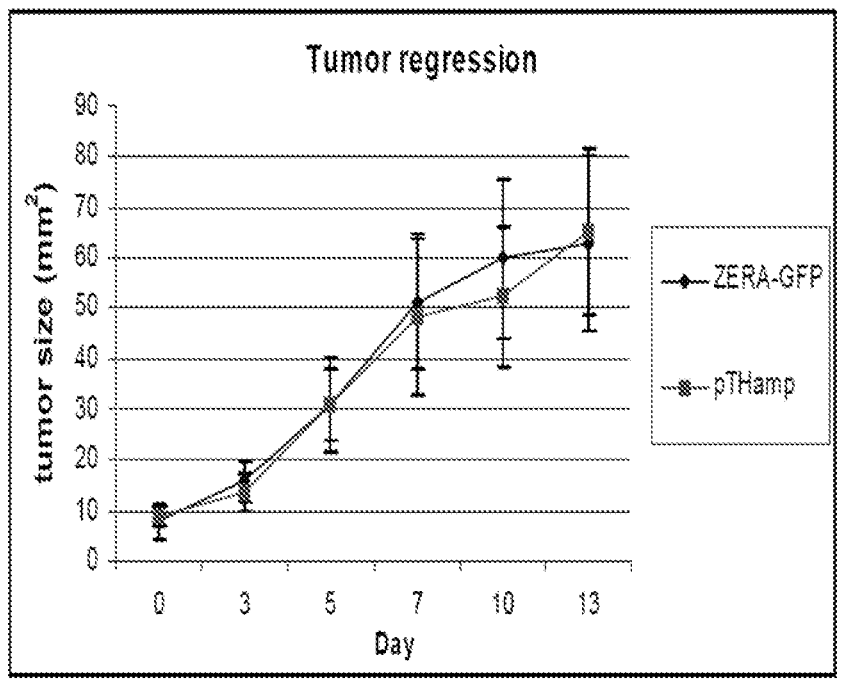
FIG. 10B illustrates that there is no unspecific tumor regression effect in DNA and RPBLAs immunizations lacking the E7SH antigen.

To exclude an unspecific tumor growth reduction due to some contaminants present in the RPBLAs preparation, or by the RX3 polypeptide by itself, equivalent amounts of RPBLAs containing RX3-Gfp were inoculated in an independent study, and no effect on tumor growth was observed when compared to pTHamp DNA control group (see FIG. 10B).

It must be pointed out that mice were inoculated only once with RPBLAs with RX3-E7SH. In a prime boost study it is expected to have an enhanced therapeutic effect.

Example 16

Protective Effect Against Tumor Growth in Mice Inoculated with RX3-E7SH

Taking into consideration a goal of the application of a protective (prophylactic) vaccine based on RPBLAs in addition to a therapeutic vaccine, rechallenge studies were undertaken to determine whether the RPBLAs containing RX3-E7SH were able to protect animals from an outgrowth of E7-expressing syngeneic tumors.

Figure 11:
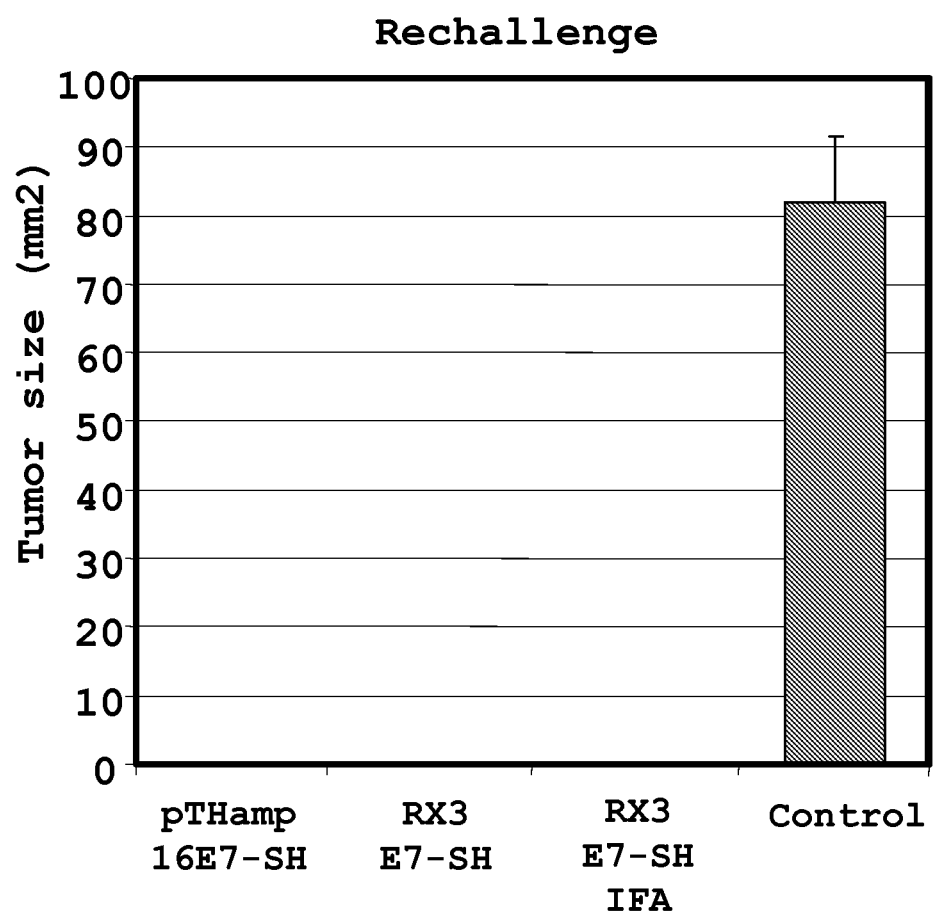
FIG. 11 is a graph showing the results of tumor growth on rechallenge studies after immunization with: (i) 100 μg plasmid expressing E7SH (pTHamp-E7SH), (ii) 5 μg of RPBLAs containing RX3-E7SH fusion protein (RX3-E7SH) or (iii) 5 μg of RPBLAs containing RX3-E7SH fusion protein and 100 μl of IFA (RX3-E7SH/IFA). Those mice that showed complete regression after the tumor regression study of FIG. 10 were injected again with 0.5× 10⁶ C3 cells s.c. in 100 μl PBS into the flank 3 weeks after completion of the tumor regression experiment. As a control, the same number of non-immunized mice received the same treatment. Twenty days after this injection, all control mice showed tumor growing, whereas none of the immunized mice developed tumors.

Those mice that showed complete regression after the tumor regression experiment were injected again with 0.5× 10$^6$ C3 cells s.c. in 100 µl PBS into the left flank 3 weeks after completion of the tumor regression study. The first C3 inoculation was given into the right flank. As a control, the same number of non-immunised mice received the same treatment. Twenty days after this injection, all control mice showed tumors with a size range of 100-400 mm$^2$, whereas the immunized mice developed no tumors, and therefore showed clear protection from tumor growth (see FIG. 11).

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

The invention claimed is:

1. A method for inducing a T-cell mediated immune response against an immunogenic peptide in a subject in need thereof, the method comprising administering to a subject in need thereof a vaccine comprising a nucleic acid molecule that encodes a recombinant fusion protein, said recombinant fusion protein comprising a protein body-inducing sequence (PBIS) and an immunogenic polypeptide, wherein the PBIS comprises a signal peptide sequence that directs the fusion protein towards the endoplasmic reticulum of the expressing cell and wherein the PBIS retains the fusion protein in the endoplasmic reticulum of the expressing cell.

2. The method as defined in claim 1 wherein the PBIS comprises a prolamin.

3. The method as defined in claim 2 wherein the prolamin is selected from the group consisting of gamma-zein, alpha-zein, delta-zein, beta-zein, rice prolamin and gamma-gliadin.

4. The method as defined in claim 1 wherein the immunogenic polypeptide is selected from the group consisting of (i) a polypeptide encoded by the HPV E7 gene, (ii) a polypeptide encoded by the HIV-1 gag gene and (iii) a polypeptide encoded by the HIV-1 pol gene.

5. The method as defined in claim 1 wherein the administration is preceded by administration of a priming vaccination or inoculation using a composition comprising the immunogenic polypeptide or a nucleic acid encoding the immunogenic polypeptide.

6. The method as defined in claim 5 wherein the composition used in the priming vaccination or inoculation comprises:

(i) a particulate recombinant protein body-like assembly (RPBLA) comprising a recombinant fusion protein, said recombinant fusion protein comprising a protein body-inducing sequence (PBIS) and the immunogenic polypeptide, (ii) a nucleic acid molecule that encodes the immunogenic polypeptide, or (iii) a nucleic acid molecule that encodes a recombinant fusion protein, said recombinant fusion protein comprising a protein body-inducing sequence (PBIS) and the immunogenic polypeptide, wherein the PBIS includes a signal peptide that directs the fusion protein towards the endoplasmic reticulum of the expressing cell and wherein the PBIS retains the fusion protein in the endoplasmic reticulum of the expressing cell.

7. The method as defined in claim 1 wherein the vaccine is administered intramuscularly.

8. The method of claim 2, wherein the PBIS consists essentially of RX3.

9. The method of claim 1, wherein immunogenic polypeptide is encoded by HIV-1.

10. A method for inducing a T-cell mediated immune response against an immunogenic peptide in a subject in need thereof, the method comprising:

(i) administering a priming vaccination or inoculation comprising a nucleic acid molecule that encodes a recombinant fusion protein, said recombinant fusion protein comprising a protein body-inducing sequence (PBIS) and an immunogenic polypeptide, wherein the PBIS includes a signal peptide that directs the fusion protein towards the endoplasmic reticulum of the expressing cell, and (ii) administering a vaccine composition comprising a particulate recombinant protein body-like assembly (RPBLA) comprising a recombinant fusion protein, said recombinant fusion protein comprising a protein body-inducing sequence (PBIS) an immunogenic polypeptide and wherein the PBIS retains the fusion protein in the endoplasmic reticulum of the expressing cell.

11. The method as defined in claim 1, wherein the PBIS comprises the sequence of SEQ ID NO: 6.

* * * * *

```
                          SEQUENCE LISTING

<160> NUMBER OF SEQ ID NOS: 129

<210> SEQ ID NO 1
    <211> LENGTH: 9
    <212> TYPE: PRT
    <213> ORGANISM: ARTIFICIAL SEQUENCE
    <220> FEATURE:
    <223> OTHER INFORMATION: SYNTHETIC SEQUENCE

<400> SEQUENCE: 1

Thr Tyr Ser Thr Val Ala Ser Ser Leu
    1               5

<210> SEQ ID NO 2
    <211> LENGTH: 6
    <212> TYPE: PRT
    <213> ORGANISM: ARTIFICIAL SEQUENCE
    <220> FEATURE:
    <223> OTHER INFORMATION: SYNTHETIC SEQUENCE

<400> SEQUENCE: 2

Pro Pro Pro Val His Leu
    1               5

<210> SEQ ID NO 3
    <211> LENGTH: 7
    <212> TYPE: PRT
    <213> ORGANISM: ARTIFICIAL SEQUENCE
    <220> FEATURE:
    <223> OTHER INFORMATION: SYNTHETIC SEQUENCE

<400> SEQUENCE: 3

Pro Gln Gln Pro Phe Pro Gln
    1               5

<210> SEQ ID NO 4
    <211> LENGTH: 8
    <212> TYPE: PRT
    <213> ORGANISM: ARTIFICIAL SEQUENCE
    <220> FEATURE:
    <223> OTHER INFORMATION: SYNTHETIC SEQUENCE

<400> SEQUENCE: 4

Pro Gln Gln Gln Pro Pro Phe Ser
    1               5

<210> SEQ ID NO 5
    <211> LENGTH: 5
    <212> TYPE: PRT
    <213> ORGANISM: ARTIFICIAL SEQUENCE
    <220> FEATURE:
    <223> OTHER INFORMATION: SYNTHETIC SEQUENCE

<400> SEQUENCE: 5

Pro Gln Gln Pro Gln
    1               5

<210> SEQ ID NO 6
    <211> LENGTH: 53
    <212> TYPE: PRT
    <213> ORGANISM: ARTIFICIAL SEQUENCE
```

```
<220> FEATURE:
<223> OTHER INFORMATION: SYNTHETIC SEQUENCE

<400> SEQUENCE: 6

Pro Pro Pro Pro Val His Leu Pro Pro Val His Leu Pro Pro Pro
1               5                   10                  15

Val His Leu Pro Pro Val His Leu Pro Pro Val His Leu Pro
                20                  25                  30

Pro Pro Val His Leu Pro Pro Val His Val Pro Pro Val His
            35                  40                  45

Leu Pro Pro Pro Pro
        50

<210> SEQ ID NO 7
<211> LENGTH: 65
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 7

Gln Gln Gln Gln Gln Phe Leu Pro Ala Leu Ser Gln Leu Asp Val Val
1               5                   10                  15

Asn Pro Val Ala Tyr Leu Gln Gln Leu Leu Ala Ser Asn Pro Leu
                20                  25                  30

Ala Leu Ala Asn Val Ala Ala Tyr Gln Gln Gln Gln Leu Gln Gln
            35                  40                  45

Phe Leu Pro Ala Leu Ser Gln Leu Ala Met Val Asn Pro Ala Ala Tyr
    50                  55                  60

Leu
65

<210> SEQ ID NO 8
<211> LENGTH: 70
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 8

Gln Gln Val Leu Ser Pro Tyr Asn Glu Phe Val Arg Gln Gln Tyr Gly
1               5                   10                  15

Ile Ala Ala Ser Pro Phe Leu Gln Ser Ala Thr Phe Gln Leu Arg Asn
                20                  25                  30

Asn Gln Val Trp Gln Gln Leu Ala Leu Val Ala Gln Gln Ser His Cys
            35                  40                  45

Gln Asp Ile Asn Ile Val Gln Ala Ile Ala Gln Gln Leu Gln Leu Gln
    50                  55                  60

Gln Phe Gly Asp Leu Tyr
65                  70

<210> SEQ ID NO 9
<211> LENGTH: 672
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 9
atgagggtgt tgctcgttgc cctcgctctc ctggctctcg ctgcgagcgc cacctccacg    60
```

| | |
|---|---:|
| catacaagcg gcggctgcgg ctgccagcca ccgccgccgg ttcatctacc gccgccggtg | 120 |
| catctgccac ctccggttca cctgccacct ccggtgcatc tcccaccgcc ggtccacctg | 180 |
| ccgccgccgg tccacctgcc accgccggtc catgtgccgc cgccggttca tctgccgccg | 240 |
| ccaccatgcc actaccctac tcaaccgccc ggcctcagc ctcatcccca gccacaccca | 300 |
| tgcccgtgcc aacagccgca tccaagcccg tgccagctgc agggaacctg cggcgttggc | 360 |
| agcaccccga tcctgggcca gtgcgtcgag tttctgaggc atcagtgcag cccgacggcg | 420 |
| acgccctact gctcgcctca gtgccagtcg ttgcggcagc agtgttgcca gcagctcagg | 480 |
| caggtggagc cgcagcaccg gtaccaggcg atcttcggct tggtcctcca gtccatcctg | 540 |
| cagcagcagc cgcaaagcgg ccaggtcgcg gggctgttgg cggcgcagat agcgcagcaa | 600 |
| ctgacggcga tgtgcggcct gcagcagccg actccatgcc cctacgctgc tgccggcggt | 660 |
| gtcccccacg cc | 672 |

<210> SEQ ID NO 10
<211> LENGTH: 224
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 10

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val His Leu Pro Pro Val His Leu Pro Pro Val His Leu
        35                  40                  45

Pro Pro Pro Val His Leu Pro Pro Val His Leu Pro Pro Val
    50                  55                  60

His Leu Pro Pro Val His Val Pro Pro Val His Leu Pro Pro
65                  70                  75                  80

Pro Pro Cys His Tyr Pro Thr Gln Pro Pro Arg Pro Gln Pro His Pro
                85                  90                  95

Gln Pro His Pro Cys Pro Cys Gln Gln Pro His Pro Ser Pro Cys Gln
            100                 105                 110

Leu Gln Gly Thr Cys Gly Val Gly Ser Thr Pro Ile Leu Gly Gln Cys
        115                 120                 125

Val Glu Phe Leu Arg His Gln Cys Ser Pro Thr Ala Thr Pro Tyr Cys
    130                 135                 140

Ser Pro Gln Cys Gln Ser Leu Arg Gln Gln Cys Cys Gln Gln Leu Arg
145                 150                 155                 160

Gln Val Glu Pro Gln His Arg Tyr Gln Ala Ile Phe Gly Leu Val Leu
                165                 170                 175

Gln Ser Ile Leu Gln Gln Pro Gln Ser Gly Gln Val Ala Gly Leu
            180                 185                 190

Leu Ala Ala Gln Ile Ala Gln Gln Leu Thr Ala Met Cys Gly Leu Gln
        195                 200                 205

Gln Pro Thr Pro Cys Pro Tyr Ala Ala Ala Gly Gly Val Pro His Ala
    210                 215                 220

<210> SEQ ID NO 11
<211> LENGTH: 339
<212> TYPE: DNA
<213> ORGANISM: ARTIFICIAL SEQUENCE

-continued

<220> FEATURE:
<223> OTHER INFORMATION: SYNTHETIC SEQUENCE

<400> SEQUENCE: 11

```
atgagggtgt tgctcgttgc cctcgctctc ctggctctcg ctgcgagcgc cacctccacg      60
catacaagcg gcggctgcgg ctgccagcca ccgccgccgg ttcatctacc gccgccggtg     120
catctgccac ctccggttca cctgccacct ccggtgcatc tcccaccgcc ggtccacctg     180
ccgccgccgg tccacctgcc accgccggtc catgtgccgc cgccggttca tctgccgccg     240
ccaccatgcc actaccctac tcaaccgccc ggcctcagc ctcatcccca gccacaccca     300
tgcccgtgcc aacagccgca tccaagcccg tgccagacc                            339
```

<210> SEQ ID NO 12
<211> LENGTH: 113
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 12

```
Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val His Leu Pro Pro Pro Val His Leu Pro Pro Val His Leu
            35                  40                  45

Pro Pro Pro Val His Leu Pro Pro Val His Leu Pro Pro Val
50                  55                  60

His Leu Pro Pro Pro Val His Val Pro Pro Val His Leu Pro Pro
65                  70                  75                  80

Pro Pro Cys His Tyr Pro Thr Gln Pro Pro Arg Pro Gln Pro His Pro
                85                  90                  95

Gln Pro His Pro Cys Pro Cys Gln Gln Pro His Pro Ser Pro Cys Gln
            100                 105                 110

Tyr
```

<210> SEQ ID NO 13
<211> LENGTH: 240
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 13

```
atgagggtgt tgctcgttgc cctcgctctc ctggctctcg ctgcgagcgc cacctccacg      60
catacaagcg gcggctgcgg ctgccagcca ccgccgccgg ttcatctacc gccgccggtg     120
catctgccac ctccggttca cctgccacct ccggtgcatc tcccaccgcc ggtccacctg     180
ccgccgccgg tccacctgcc accgccggtc catgtgccgc cgccggttca tctgccgccg     240
```

<210> SEQ ID NO 14
<211> LENGTH: 92
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 14

Met Arg Val Leu Leu Val Ala Leu Ala Leu Leu Ala Leu Ala Ala Ser

```
  1               5                   10                  15
Ala Thr Ser Thr His Thr Ser Gly Gly Cys Gly Cys Gln Pro Pro
              20                  25                  30

Pro Val His Leu Pro Pro Pro Val His Leu Pro Pro Pro Val His Leu
              35                  40                  45

Pro Pro Pro Val His Leu Pro Pro Pro Val His Leu Pro Pro Pro Val
          50                  55                  60

His Leu Pro Pro Pro Val His Val Pro Pro Val His Leu Pro Pro
65                  70                  75                  80

Pro Pro Cys His Tyr Pro Thr Gln Pro Pro Arg Tyr
              85                  90

<210> SEQ ID NO 15
<211> LENGTH: 213
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 15
atgagggtgt tgctcgttgc cctcgctctc ctggctctcg ctgcgagcgc cacctccacg    60
catacaagcg gcggctgcgg ctgccagcca ccgccgccgg ttcatctgcc gccgccacca   120
tgccactacc ctacacaacc gccccggcct cagcctcatc cccagccaca cccatgcccg   180
tgccaacagc cgcatccaag cccgtgccag acc                                213

<210> SEQ ID NO 16
<211> LENGTH: 71
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 16

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro
              20                  25                  30

Pro Val His Leu Pro Pro Pro Cys His Tyr Pro Thr Gln Pro Pro
              35                  40                  45

Arg Pro Gln Pro His Pro Gln Pro His Pro Cys Pro Cys Gln Gln Pro
          50                  55                  60

His Pro Ser Pro Cys Gln Tyr
65                  70

<210> SEQ ID NO 17
<211> LENGTH: 180
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 17
atgagggtgt tgctcgttgc cctcgctctc ctggctctcg ctgcgagcgc cacctccacg    60
catacaagcg gcggctgcgg ctgccaatgc cactacccta ctcaaccgcc ccggcctcag   120
cctcatcccc agccacaccc atgcccgtgc caacagccgc atccaagccc gtgccagacc   180

<210> SEQ ID NO 18
<211> LENGTH: 60
```

<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 18

Met Arg Val Leu Leu Val Ala Leu Ala Leu Ala Leu Ala Ala Ser
1               5                   10                  15

Ala Thr Ser Thr His Thr Ser Gly Gly Cys Gly Cys Gln Cys His Tyr
            20                  25                  30

Pro Thr Gln Pro Pro Arg Pro Gln Pro His Pro Gln Pro His Pro Cys
        35                  40                  45

Pro Cys Gln Gln Pro His Pro Ser Pro Cys Gln Tyr
    50                  55                  60

<210> SEQ ID NO 19
<211> LENGTH: 150
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 19

Met Lys Ile Ile Phe Val Phe Ala Leu Leu Ala Ile Ala Ala Cys Ser
1               5                   10                  15

Ala Ser Ala Gln Phe Asp Val Leu Gly Gln Ser Tyr Arg Gln Tyr Gln
            20                  25                  30

Leu Gln Ser Pro Val Leu Leu Gln Gln Val Leu Ser Pro Tyr Asn
        35                  40                  45

Glu Phe Val Arg Gln Gln Tyr Gly Ile Ala Ala Ser Pro Phe Leu Gln
    50                  55                  60

Ser Ala Thr Phe Gln Leu Arg Asn Asn Gln Val Trp Gln Gln Leu Ala
65                  70                  75                  80

Leu Val Ala Gln Gln Ser His Cys Gln Asp Ile Asn Ile Val Gln Ala
                85                  90                  95

Ile Ala Gln Gln Leu Gln Leu Gln Gln Phe Gly Asp Leu Tyr Phe Asp
            100                 105                 110

Arg Asn Leu Ala Gln Ala Gln Ala Leu Leu Ala Phe Asn Val Pro Ser
        115                 120                 125

Arg Tyr Gly Ile Tyr Pro Arg Tyr Tyr Gly Ala Pro Ser Thr Ile Thr
    130                 135                 140

Thr Leu Gly Gly Val Leu
145                 150

<210> SEQ ID NO 20
<211> LENGTH: 450
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 20
atgaagatca ttttcgtctt tgctctcctt gctattgctg catgcagcgc ctctgcgcag    60
tttgatgttt taggtcaaag ttataggcaa tatcagctgc agtcgcctgt cctgctacag   120
caacaggtgc ttagcccata taatgagttc gtaaggcagc agtatggcat agcggcaagc   180
cccttcttgc aatcagctac gtttcaactg agaaacaacc aagtctggca acagctcgcg   240
ctggtggcgc aacaatctca ctgtcaggac attaacattg ttcaggccat agcgcagcag   300

```
ctacaactcc agcagtttgg tgatctctac tttgatcgga atctggctca agctcaagct    360
ctgttggctt ttaacgtgcc atctagatat ggtatctacc ctaggtacta tggtgcaccc    420
agtaccatta ccaccttgg cggtgtcttg                                      450
```

<210> SEQ ID NO 21
<211> LENGTH: 144
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 21

```
Met Ala Thr Lys Ile Leu Ala Leu Leu Ala Leu Leu Ala Leu Phe Val
1               5                   10                  15

Ser Ala Thr Asn Ala Phe Ile Ile Pro Gln Cys Ser Leu Ala Pro Ser
            20                  25                  30

Ala Ile Ile Pro Gln Phe Leu Pro Pro Val Thr Ser Met Gly Phe Glu
        35                  40                  45

His Leu Ala Val Gln Ala Tyr Arg Leu Gln Gln Ala Leu Ala Ala Ser
    50                  55                  60

Val Leu Gln Gln Pro Ile Asn Gln Leu Gln Gln Ser Leu Ala His
65                  70                  75                  80

Leu Thr Ile Gln Thr Ile Ala Thr Gln Gln Gln Gln Phe Leu Pro
                85                  90                  95

Ala Leu Ser Gln Leu Asp Val Val Asn Pro Val Ala Tyr Leu Gln Gln
            100                 105                 110

Gln Leu Leu Ala Ser Asn Pro Leu Ala Leu Ala Asn Val Ala Ala Tyr
        115                 120                 125

Gln Gln Gln Gln Gln Leu Gln Gln Phe Leu Pro Ala Leu Ser Gln Leu
    130                 135                 140
```

<210> SEQ ID NO 22
<211> LENGTH: 432
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 22

```
atggctacca agatattagc cctccttgcg cttcttgccc tttttgtgag cgcaacaaat    60
gcgttcatta ttccacaatg ctcacttgct cctagtgcca ttataccaca gttcctccca    120
ccagttactt caatgggctt cgaacaccta gctgtgcaag cctacaggct acaacaagcg    180
cttgcggcaa gcgtcttaca caaccaatt aaccaattgc aacaacaatc cttggcacat    240
ctaaccatac aaaccatcgc aacgcaacag caacaacagt cctaccagc actgagccaa    300 ctagatgtgg tgaaccctgt cgcctacttg caacagcagc tgcttgcatc caacccactt    360
gctctggcaa acgtagctgc ataccaacaa caacaacaat gcagcagtt tctgccagcg    420 ctcagtcaac ta                                                        432
```

<210> SEQ ID NO 23
<211> LENGTH: 283
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 23

```
Asn Met Gln Val Asp Pro Ser Gly Gln Val Gln Trp Pro Gln Gln Gln
1               5                   10                  15

Pro Phe Pro Gln Pro Gln Gln Pro Phe Cys Gln Pro Gln Arg Thr
            20                  25                  30

Ile Pro Gln Pro His Gln Thr Phe His His Gln Pro Gln Gln Thr Phe
            35                  40                  45

Pro Gln Pro Gln Gln Thr Tyr Pro His Gln Pro Gln Gln Phe Pro
        50                  55                  60

Gln Thr Gln Gln Pro Gln Pro Phe Pro Gln Pro Gln Gln Thr Phe
65                  70                  75                  80

Pro Gln Gln Pro Gln Leu Pro Phe Pro Gln Pro Gln Gln Pro Phe
            85                  90                  95

Pro Gln Pro Gln Gln Pro Gln Pro Phe Pro Gln Ser Gln Gln Pro
            100                 105                 110

Gln Gln Pro Phe Pro Gln Pro Gln Gln Phe Pro Gln Pro Gln Gln
        115                 120                 125

Pro Gln Gln Ser Phe Pro Gln Gln Gln Pro Ala Ile Gln Ser Phe
    130                 135                 140

Leu Gln Gln Gln Met Asn Pro Cys Lys Asn Phe Leu Leu Gln Gln Cys
145                 150                 155                 160

Asn His Val Ser Leu Val Ser Ser Leu Val Ser Ile Ile Leu Pro Arg
                165                 170                 175

Ser Asp Cys Gln Val Met Gln Gln Cys Cys Gln Gln Leu Ala Gln
            180                 185                 190

Ile Pro Gln Gln Leu Gln Cys Ala Ala Ile His Ser Val Ala His Ser
        195                 200                 205

Ile Ile Met Gln Gln Glu Gln Gln Gln Gly Val Pro Ile Leu Arg Pro
210                 215                 220

Leu Phe Gln Leu Ala Gln Gly Leu Gly Ile Ile Gln Pro Gln Gln Pro
225                 230                 235                 240

Ala Gln Leu Glu Gly Ile Arg Ser Leu Val Leu Lys Thr Leu Pro Thr
            245                 250                 255

Met Cys Asn Val Tyr Val Pro Pro Asp Cys Ser Thr Ile Asn Val Pro
            260                 265                 270

Tyr Ala Asn Ile Asp Ala Gly Ile Gly Gly Gln
        275                 280

<210> SEQ ID NO 24
<211> LENGTH: 2086
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 24
gcatgcattg tcaaagtttg tgaagtagaa ttaataacct tttggttatt gatcactgta      60
tgtatcttag atgtcccgta gcaacggtaa gggcattcac ctagtactag tccaatatta     120
attaataact tgcacagaat tacaaccatt gacataaaaa ggaaatatga tgagtcatgt     180
attgattcat gttcaacatt actacccttg acataaaaga agaatttgac gagtcgtatt     240
agcttgttca tcttaccatc atactatact gcaagctagt ttaaaaaaga atyaaagtcc     300
agaatgaaca gtagaatagc ctgatctatc tttaacaaca tgcacaagaa tacaaattta     360
gtcccttgca agctatgaag atttggttta tgcctaacaa catgtaaaac ttagatccaa     420
aaggaatgca atctagataa ttgtttgact tgtaaagtcg ataagatgag tcagtgccaa     480
```

```
ttataaagtt ttcgccactc ttagatcata tgtacaataa aaaggcaact ttgctgacca      540
ctccaaaagt acgtttgtat gtagtgccac caaacacaac acaccaaata atcagtttga      600
taagcatcga atcactttaa aaagtgaaag aaataatgaa aagaaaccta accatggtag      660
ctataaaaag cctgtaatat gtacactcca taccatcatc catccttcac acaactagag      720
cacaagcatc aaatccaagt aagtattagt taacgcaaat ccaccatgaa gaccttactc      780
atcctaacaa tccttgcgat ggcaacaacc atcgccaccg ccaatatgca agtcgacccc      840
agcggccaag tacaatggcc acaacaacaa ccattccccc agccccaaca accattctgc      900
cagcaaccac aacgaactat tccccaaccc catcaaacat tccaccatca accacaacaa      960
acatttcccc aaccccaaca acatacccca tcaaccac aacaacaatt ccccagacc     1020 caacaaccac aacaaccatt tccccagccc caacaaacat tccccaaca accccaacta     1080 ccatttcccc aacaacccca caaccattc ccccagcctc agcaaccca caaccattt     1140 ccccagtcac aacaaccaca acaacctttt ccccagcccc aacaacaatt ccgcagcccc     1200
caacaaccac aacaatcatt cccccaacaa caacaaccgg cgattcagtc atttctacaa     1260
caacagatga accctgcaa gaatttcctc ttgcagcaat gcaaccatgt gtcattggtg     1320
tcatctctcg tgtcaataat tttgccacga agtgattgcc aggtgatgca gcaacaatgt     1380
tgccaacaac tagcacaaat tcctcaacag ctccagtgcg cagccatcca cagcgtcgcg     1440
cattccatca tcatgcaaca agaacaacaa caaggcgtgc cgatcctgcg gccactattt     1500
cagctcgccc agggtctggg tatcatccaa cctcaacaac cagctcaatt ggagggatc      1560 aggtcattgg tattgaaaac tcttccaacc atgtgcaacg tgtatgtgcc acctgactgc     1620
tccaccatca acgtaccata tgccaacata gacgctggca ttggtggcca atgaaaaatg     1680
caagatcatc attgcttagc tgatgcacca atcgttgtag cgatgacaaa taaagtggtg     1740
tgcaccatca tgtgtgaccc cgaccagtgc tagttcaagc ttgggaataa agacaaaca     1800 aagttcttgt ttgctagcat tgcttgtcac tgttacattc acttttatt tcgatgttca     1860 tccctaaccg caatcctagc cttacacgtc aatagctagc tgcttgtgct ggcaggttac     1920
tatataatct atcaattaat ggtcgaccta ttaatccaag taataggcta ttgatagact     1980
gctcccaagc cgaccgagca cctatcagtt acggatttct tgaacattgc acactataat     2040
aattcaacgt atttcaacct ctagaagtaa agggcatttt agtagc                    2086
```

<210> SEQ ID NO 25
<211> LENGTH: 537
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 25

```
atgaagatgg tcatcgttct cgtcgtgtgc ctggctctgt cagctgccag cgcctctgca       60
atgcagatgc cctgcccctg cgcggggctg cagggcttgt acggcgctgg cgccggcctg      120
acgacgatga tgggcgccgg cgggctgtac ccctacgcgg agtacctgag gcagccgcag      180
tgcagcccgc tggcggcggc gccctactac gccgggtgtg gcagccgag cgccatgttc      240 cagccgctcc ggcaacagtg ctgccagcag cagatgagga tgatggacgt gcagtccgtc      300
gcgcagcagc tgcagatgat gatgcagctt gagcgtgccg ctgccgccag cagcagcctg      360
tacgagccag ctctgatgca gcagcagcag cagctgctgg cagcccaggg tctcaacccc      420
```

```
atggccatga tgatggcgca gaacatgccg gccatgggtg gactctacca gtaccagctg    480
cccagctacc gcaccaaccc ctgtggcgtc tccgctgcca ttccgcccta ctactga      537
```

<210> SEQ ID NO 26
<211> LENGTH: 178
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 26

```
Met Lys Met Val Ile Val Leu Val Val Cys Leu Ala Leu Ser Ala Ala
1               5                   10                  15

Ser Ala Ser Ala Met Gln Met Pro Cys Pro Cys Ala Gly Leu Gln Gly
            20                  25                  30

Leu Tyr Gly Ala Gly Ala Gly Leu Thr Thr Met Met Gly Ala Gly Gly
        35                  40                  45

Leu Tyr Pro Tyr Ala Glu Tyr Leu Arg Gln Pro Gln Cys Ser Pro Leu
    50                  55                  60

Ala Ala Ala Pro Tyr Tyr Ala Gly Cys Gly Gln Pro Ser Ala Met Phe
65                  70                  75                  80

Gln Pro Leu Arg Gln Gln Cys Cys Gln Gln Met Arg Met Met Asp
                85                  90                  95

Val Gln Ser Val Ala Gln Leu Gln Met Met Met Gln Leu Glu Arg
                100                 105                 110

Ala Ala Ala Ala Ser Ser Ser Leu Tyr Glu Pro Ala Leu Met Gln Gln
            115                 120                 125

Gln Gln Gln Leu Leu Ala Ala Gln Gly Leu Asn Pro Met Ala Met Met
        130                 135                 140

Met Ala Gln Asn Met Pro Ala Met Gly Gly Leu Tyr Gln Tyr Gln Leu
145                 150                 155                 160

Pro Ser Tyr Arg Thr Asn Pro Cys Gly Val Ser Ala Ala Ile Pro Pro
                165                 170                 175

Tyr Tyr
```

<210> SEQ ID NO 27
<211> LENGTH: 453
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 27

```
atggcagcca agatgcttgc attgttcgct ctcctagctc tttgtgcaag cgccactagt    60
gcgacgcata ttccagggca cttgccacca gtcatgccat gggtaccat gaacccatgc    120 atgcagtact gcatgatgca cagggggctt gccagcttga tggcgtgtcc gtccctgatg    180
ctgcagcaac tgttggcctt accgcttcag acgatgccag tgatgatgcc acagatgatg    240
acgcctaaca tgatgtcacc attgatgatg ccagcatga tgtcaccaat ggtcttgccg    300
agcatgatgt cgcaaatgat gatgccacaa tgtcactgcg acgccgtctc gcagattatg    360
ctgcaacagc agttaccatt catgttcaac ccaatggcca tgacgattcc acccatgttc    420
ttacagcaac cctttgttgg tgctgcattc tag                                 453
```

<210> SEQ ID NO 28
<211> LENGTH: 150
<212> TYPE: PRT

```
<213> ORGANISM: ARTIFICIAL SEQUENCE
<220> FEATURE:
<223> OTHER INFORMATION: SYNTHETIC SEQUENCE

<400> SEQUENCE: 28

Met Ala Ala Lys Met Leu Ala Leu Phe Ala Leu Leu Ala Leu Cys Ala
1               5                   10                  15

Ser Ala Thr Ser Ala Thr His Ile Pro Gly His Leu Pro Pro Val Met
            20                  25                  30

Pro Leu Gly Thr Met Asn Pro Cys Met Gln Tyr Cys Met Met Gln Gln
        35                  40                  45

Gly Leu Ala Ser Leu Met Ala Cys Pro Ser Leu Met Leu Gln Gln Leu
    50                  55                  60

Leu Ala Leu Pro Leu Gln Thr Met Pro Val Met Met Pro Gln Met Met
65                  70                  75                  80

Thr Pro Asn Met Met Ser Pro Leu Met Met Pro Ser Met Met Ser Pro
                85                  90                  95

Met Val Leu Pro Ser Met Met Ser Gln Met Met Met Pro Gln Cys His
            100                 105                 110

Cys Asp Ala Val Ser Gln Ile Met Leu Gln Gln Gln Leu Pro Phe Met
        115                 120                 125

Phe Asn Pro Met Ala Met Thr Ile Pro Pro Met Phe Leu Gln Gln Pro
    130                 135                 140

Phe Val Gly Ala Ala Phe
145                 150

<210> SEQ ID NO 29
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 29

Met Arg Val Leu Leu Val Ala Leu Ala Leu Leu Ala Leu Ala Ala Ser
1               5                   10                  15

Ala Thr Ser

<210> SEQ ID NO 30
<211> LENGTH: 20
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 30

Met Lys Thr Phe Leu Ile Leu Val Leu Leu Ala Ile Val Ala Thr Thr
1               5                   10                  15

Ala Thr Thr Ala
            20

<210> SEQ ID NO 31
<211> LENGTH: 21
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 31

Met Lys Thr Leu Leu Ile Leu Thr Ile Leu Ala Met Ala Ile Thr Ile
1               5                   10                  15
```

Gly Thr Ala Asn Met
            20

<210> SEQ ID NO 32
<211> LENGTH: 25
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 32

Met Asn Phe Leu Lys Ser Phe Pro Phe Tyr Ala Phe Leu Cys Phe Gly
1               5                   10                  15

Gln Tyr Phe Val Ala Val Thr His Ala
            20                  25

<210> SEQ ID NO 33
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 33

Gly Pro Lys Glu Pro Phe Arg Asp Tyr Val Asp Arg Phe Tyr Lys Cys
1               5                   10                  15

<210> SEQ ID NO 34
<211> LENGTH: 17
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 34

Phe Gln Val Val His Asn Ser Tyr Asn Arg Pro Ala Tyr Ser Pro Gly
1               5                   10                  15

Cys

<210> SEQ ID NO 35
<211> LENGTH: 25
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 35

Val Glu Ile Lys Glu Gly Thr Val Thr Leu Lys Arg Glu Ile Asp Lys
1               5                   10                  15

Asn Gly Lys Val Thr Val Ser Leu Cys
            20                  25

<210> SEQ ID NO 36
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 36

Thr Leu Ser Lys Asn Ile Ser Lys Ser Gly Glu Val Ser Val Glu Leu
1               5                   10                  15

Asn Asp Cys

```
<210> SEQ ID NO 37
<211> LENGTH: 11
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 37

Ser Ser Val Ser Ser Phe Glu Arg Phe Glu Cys
1               5                   10

<210> SEQ ID NO 38
<211> LENGTH: 10
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 38

Leu Ile Asp Ala Leu Leu Gly Asp Pro Cys
1               5                   10

<210> SEQ ID NO 39
<211> LENGTH: 9
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 39

Thr Leu Ile Asp Ala Leu Leu Gly Cys
1               5

<210> SEQ ID NO 40
<211> LENGTH: 24
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 40

Phe Trp Arg Gly Glu Asn Gly Arg Lys Thr Arg Ser Ala Tyr Glu Arg
1               5                   10                  15

Met Cys Asn Ile Leu Lys Gly Lys
            20

<210> SEQ ID NO 41
<211> LENGTH: 22
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 41

Leu Arg Val Leu Ser Phe Ile Arg Gly Thr Lys Val Ser Pro Arg Gly
1               5                   10                  15

Lys Leu Ser Thr Arg Gly
            20

<210> SEQ ID NO 42
<211> LENGTH: 22
<212> TYPE: PRT
<213> ORGANISM: ARTIFICIAL SEQUENCE
<220> FEATURE:
<223> OTHER INFORMATION: SYNTHETIC SEQUENCE
```

```
<400> SEQUENCE: 42

Ser Leu Val Gly Ile Asp Pro Phe Lys Leu Leu Gln Asn Ser Gln Val
1               5                   10                  15

Tyr Ser Leu Ile Arg Pro
            20

<210> SEQ ID NO 43
<211> LENGTH: 24
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 43

Ala Val Lys Gly Val Gly Thr Met Val Met Glu Leu Ile Arg Met Ile
1               5                   10                  15

Lys Arg Gly Ile Asn Asp Arg Asn
            20

<210> SEQ ID NO 44
<211> LENGTH: 21
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 44

Ser His Asn Phe Thr Leu Val Ala Ser Val Ile Ile Glu Glu Ala Pro
1               5                   10                  15

Ser Gly Asn Thr Cys
            20

<210> SEQ ID NO 45
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 45

Ser Val Gln Ile Pro Lys Val Pro Tyr Pro Asn Gly Ile Val Tyr Cys
1               5                   10                  15

<210> SEQ ID NO 46
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 46

Asp Phe Asn His Tyr Tyr Thr Leu Lys Thr Gly Leu Glu Ala Asp Cys
1               5                   10                  15

<210> SEQ ID NO 47
<211> LENGTH: 18
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 47

Pro Ser Asp Lys His Ile Glu Gln Tyr Lys Lys Ile Lys Asn Ser Ile
1               5                   10                  15
```

Ser Cys

```
<210> SEQ ID NO 48
<211> LENGTH: 20
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 48

Glu Tyr Leu Asn Lys Ile Gln Asn Ser Leu Ser Thr Glu Trp Ser Pro
1               5                   10                  15

Cys Ser Val Thr
            20

<210> SEQ ID NO 49
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 49

Tyr Leu Asp Lys Val Arg Ala Thr Val Gly Thr Glu Trp Thr Pro Cys
1               5                   10                  15

Ser Val Thr

<210> SEQ ID NO 50
<211> LENGTH: 20
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 50

Glu Phe Val Lys Gln Ile Ser Ser Gln Leu Thr Glu Glu Trp Ser Gln
1               5                   10                  15

Cys Ser Val Thr
            20

<210> SEQ ID NO 51
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 51

Lys Pro Arg Pro Ile Tyr Glu Ala Lys Leu Ala Gln Asn Gln Lys Cys
1               5                   10                  15

<210> SEQ ID NO 52
<211> LENGTH: 17
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 52

Ala Lys Ala Asp Tyr Glu Ala Lys Leu Ala Gln Tyr Glu Lys Asp Leu
1               5                   10                  15

Cys

<210> SEQ ID NO 53
```

```
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 53

Arg Pro Gln Ala Ser Gly Val Tyr Met Gly Asn Leu Thr Ala Gln Cys
1               5                   10                  15

<210> SEQ ID NO 54
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 54

Gln Tyr Ile Lys Ala Asn Ser Lys Phe Ile Gly Ile Thr Glu Leu Cys
1               5                   10                  15

<210> SEQ ID NO 55
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 55

Ala Ile Trp Gln Val Glu Gln Lys Ala Ser Ile Ala Gly Thr Asp Ser
1               5                   10                  15

Gly Trp Cys

<210> SEQ ID NO 56
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 56

Asn Tyr Lys Asn Gly Gly Phe Phe Val Gln Tyr Gly Gly Ala Tyr Lys
1               5                   10                  15

Arg His Cys

<210> SEQ ID NO 57
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 57

His Asn Ser Gln Thr Glu Val Ala Ala Thr Leu Ala Tyr Arg Phe Gly
1               5                   10                  15

Asn Val Cys

<210> SEQ ID NO 58
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 58
```

```
Thr Pro Arg Val Ser Tyr Ala His Gly Phe Lys Gly Leu Val Asp Asp
1               5                   10                  15

Ala Asp Cys

<210> SEQ ID NO 59
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 59

Arg Phe Gly Asn Ala Val Pro Arg Ile Ser Tyr Ala His Gly Phe Asp
1               5                   10                  15

Phe Ile Cys

<210> SEQ ID NO 60
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 60

Ala Phe Lys Tyr Ala Arg His Ala Asn Val Gly Arg Asn Ala Phe Glu
1               5                   10                  15

Leu Phe Cys

<210> SEQ ID NO 61
<211> LENGTH: 20
<212> TYPE: PRT
<213> ORGANISM: ARTIFICIAL SEQUENCE
<220> FEATURE:
<223> OTHER INFORMATION: SYNTHEIC SEQUENCE

<400> SEQUENCE: 61

Ser Gly Ala Trp Leu Lys Arg Asn Thr Gly Ile Gly Asn Tyr Thr Gln
1               5                   10                  15

Ile Asn Ala Cys
            20

<210> SEQ ID NO 62
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 62

Ala Gly Glu Phe Gly Thr Leu Arg Ala Gly Arg Val Ala Asn Gln Cys
1               5                   10                  15

<210> SEQ ID NO 63
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 63

Ile Gly Asn Tyr Thr Gln Ile Asn Ala Ala Ser Val Gly Leu Arg Cys
1               5                   10                  15

<210> SEQ ID NO 64
```

<211> LENGTH: 16
<212> TYPE: PRT
<213> ORGANISM: ARTIFICIAL SEQUENCE
<220> FEATURE:
<223> OTHER INFORMATION: SYNTHEIC SEQUENCE

<400> SEQUENCE: 64

Gly Arg Asn Tyr Gln Leu Gln Leu Thr Glu Gln Pro Ser Arg Thr Cys
1               5                   10                  15

<210> SEQ ID NO 65
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 65

Ser Gly Ser Val Gln Phe Val Pro Ala Gln Asn Ser Lys Ser Ala Cys
1               5                   10                  15

<210> SEQ ID NO 66
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 66

His Ala Asn Val Gly Arg Asp Ala Phe Asn Leu Phe Leu Leu Gly Cys
1               5                   10                  15

<210> SEQ ID NO 67
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 67

Leu Gly Arg Ile Gly Asp Asp Glu Ala Lys Gly Thr Asp Pro Cys
1               5                   10                  15

<210> SEQ ID NO 68
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 68

Ser Val Gln Phe Val Pro Ala Gln Asn Ser Lys Ser Ala Tyr Lys Cys
1               5                   10                  15

<210> SEQ ID NO 69
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 69

Asn Tyr Ala Phe Lys Tyr Ala Lys His Ala Asn Val Gly Arg Asp Cys
1               5                   10                  15

<210> SEQ ID NO 70
<211> LENGTH: 16

<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 70

Ala His Gly Phe Asp Phe Ile Glu Arg Gly Lys Lys Gly Glu Asn Cys
1               5                   10                  15

<210> SEQ ID NO 71
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 71

Gly Val Asp Tyr Asp Phe Ser Lys Arg Thr Ser Ala Ile Val Ser Cys
1               5                   10                  15

<210> SEQ ID NO 72
<211> LENGTH: 16
<212> TYPE: PRT
<213> ORGANISM: ARTIFICIAL SEQUENCE
<220> FEATURE:
<223> OTHER INFORMATION: ARTIFICIAL SEQUENCE

<400> SEQUENCE: 72

His Asp Asp Met Pro Val Ser Val Arg Tyr Asp Ser Pro Asp Phe Cys
1               5                   10                  15

<210> SEQ ID NO 73
<211> LENGTH: 27
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 73

Arg Phe Gly Asn Ala Val Pro Arg Ile Ser Tyr Ala His Gly Phe Asp
1               5                   10                  15

Phe Ile Glu Arg Gly Lys Lys Gly Glu Asn Cys
            20                  25

<210> SEQ ID NO 74
<211> LENGTH: 24
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 74

Asn Tyr Ala Phe Lys Tyr Ala Lys His Ala Asn Val Gly Arg Asp Ala
1               5                   10                  15

Phe Asn Leu Phe Leu Leu Gly Cys
            20

<210> SEQ ID NO 75
<211> LENGTH: 26
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 75

Ser Gly Ala Trp Leu Lys Arg Asn Thr Gly Ile Gly Asn Tyr Thr Gln

```
                1               5                   10                  15
Ile Asn Ala Ala Ser Val Gly Leu Arg Cys
            20                  25

<210> SEQ ID NO 76
<211> LENGTH: 20
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 76

Ser Gly Ser Val Gln Phe Val Pro Ala Gln Asn Ser Lys Ser Ala Tyr
1               5                   10                  15

Thr Pro Ala Cys
            20

<210> SEQ ID NO 77
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 77

Thr Gly Ala Asn Asn Thr Ser Thr Val Ser Asp Tyr Phe Arg Asn Arg
1               5                   10                  15

Ile Thr Cys

<210> SEQ ID NO 78
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 78

Ile Tyr Asp Phe Lys Leu Asn Asp Lys Phe Asp Lys Phe Lys Pro Tyr
1               5                   10                  15

Ile Gly Cys

<210> SEQ ID NO 79
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 79

Leu Ser Ala Ile Tyr Asp Phe Lys Leu Asn Asp Lys Phe Lys Pro Tyr
1               5                   10                  15

Ile Gly Cys

<210> SEQ ID NO 80
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 80

Asn Gly Trp Tyr Ile Asn Pro Trp Ser Glu Val Lys Phe Asp Leu Asn
1               5                   10                  15
```

Ser Arg Cys

<210> SEQ ID NO 81
<211> LENGTH: 21
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 81

Met Gly Thr Asn Leu Ser Val Pro Asn Pro Leu Gly Phe Phe Pro Asp
1               5                   10                  15

His Gln Leu Asp Pro
            20

<210> SEQ ID NO 82
<211> LENGTH: 8
<212> TYPE: PRT
<213> ORGANISM: ARTIFICIAL PROTEIN
<220> FEATURE:
<223> OTHER INFORMATION: SYNTHETIC SEQUENCE

<400> SEQUENCE: 82

Pro Leu Gly Phe Phe Pro Asp His
1               5

<210> SEQ ID NO 83
<211> LENGTH: 10
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 83

Pro Leu Gly Phe Phe Pro Asp His Gln Leu
1               5                   10

<210> SEQ ID NO 84
<211> LENGTH: 26
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 84

Met Gln Trp Asn Ser Thr Ala Phe His Gln Thr Leu Gln Asp Pro Arg
1               5                   10                  15

Val Arg Gly Leu Tyr Leu Pro Ala Gly Gly
            20                  25

<210> SEQ ID NO 85
<211> LENGTH: 14
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 85

Met Gln Trp Ser Thr Ala Phe His Gln Thr Leu Gln Asp Pro
1               5                   10

<210> SEQ ID NO 86
<211> LENGTH: 15
<212> TYPE: PRT
<213> ORGANISM: ARTIFICIAL SEQUENCE
<220> FEATURE:

<223> OTHER INFORMATION: SYNTHETIC SEQUENCE

<400> SEQUENCE: 86

Met Gln Trp Asn Ser Thr Ala Leu His Gln Ala Leu Gln Asp Pro
1               5                   10                  15

<210> SEQ ID NO 87
<211> LENGTH: 6
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 87

Gln Asp Pro Arg Val Arg
1               5

<210> SEQ ID NO 88
<211> LENGTH: 20
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 88

Met Asp Ile Asp Pro Tyr Lys Glu Phe Gly Ala Thr Val Glu Leu Leu
1               5                   10                  15

Ser Phe Leu Pro
            20

<210> SEQ ID NO 89
<211> LENGTH: 25
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 89

Arg Asp Leu Leu Asp Thr Ala Ser Ala Leu Tyr Arg Glu Ala Leu Glu
1               5                   10                  15

Ser Pro Glu His Cys Ser Pro His His
            20                  25

<210> SEQ ID NO 90
<211> LENGTH: 25
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 90

Thr Trp Val Gly Val Asn Leu Glu Asp Pro Ala Ser Arg Asp Leu Val
1               5                   10                  15

Val Ser Tyr Val Asn Thr Asn Met Gly
            20                  25

<210> SEQ ID NO 91
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 91

Val Val Ser Tyr Val Asn Thr Asn Met Gly Leu Lys Phe Arg Gln Leu

<210> SEQ ID NO 92
<211> LENGTH: 21
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 92

Leu Leu Trp Phe His Ile Ser Cys Leu Thr Phe Gly Arg Glu Thr Val
1               5                   10                  15

Ile Glu Tyr Leu Val
            20

<210> SEQ ID NO 93
<211> LENGTH: 11
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 93

Leu Leu Trp Phe His Ile Ser Cys Leu Thr Phe
1               5                   10

<210> SEQ ID NO 94
<211> LENGTH: 21
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 94

Val Ser Phe Gly Val Trp Ile Arg Thr Pro Pro Ala Tyr Arg Pro Pro
1               5                   10                  15

Asn Ala Pro Ile Leu
            20

<210> SEQ ID NO 95
<211> LENGTH: 12
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 95

Val Ser Phe Gly Val Trp Ile Arg Thr Pro Pro Ala
1               5                   10

<210> SEQ ID NO 96
<211> LENGTH: 12
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 96

Pro Pro Ala Tyr Arg Pro Pro Asn Ala Pro Ile Leu
1               5                   10

<210> SEQ ID NO 97
<211> LENGTH: 12
<212> TYPE: PRT
<213> ORGANISM: ARTIFICIAL SEQUENCE
<220> FEATURE:

```
<223> OTHER INFORMATION: SYNTHETIC SEQUENCE

<400> SEQUENCE: 97

Trp Ile Arg Thr Pro Pro Ala Tyr Arg Pro Pro Asn
1               5                   10

<210> SEQ ID NO 98
<211> LENGTH: 20
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 98

Pro His His Thr Ala Leu Arg Gln Ala Ile Leu Cys Trp Gly Glu Leu
1               5                   10                  15

Met Thr Leu Ala
            20

<210> SEQ ID NO 99
<211> LENGTH: 15
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 99

Ala Val Leu Glu Asp Pro Tyr Ile Leu Leu Val Ser Ser Lys Val
1               5                   10                  15

<210> SEQ ID NO 100
<211> LENGTH: 15
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 100

Leu Leu Val Ser Ser Lys Val Ser Thr Val Lys Asp Leu Leu Pro
1               5                   10                  15

<210> SEQ ID NO 101
<211> LENGTH: 15
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 101

Leu Leu Pro Leu Leu Glu Lys Val Ile Gly Ala Gly Lys Pro Leu
1               5                   10                  15

<210> SEQ ID NO 102
<211> LENGTH: 15
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 102

Ala Ile Leu Thr Gly Gly Gln Val Ile Ser Glu Glu Val Gly Leu
1               5                   10                  15

<210> SEQ ID NO 103
<211> LENGTH: 15
<212> TYPE: PRT
```

<213> ORGANISM: ARTIFICIAL SEQUENCE
<220> FEATURE:
<223> OTHER INFORMATION: SYNTHETIC SEQUENCE

<400> SEQUENCE: 103

```
Ile Ala Phe Asn Ser Gly Leu Glu Pro Gly Val Val Ala Glu Lys
1               5                   10                  15
```

<210> SEQ ID NO 104
<211> LENGTH: 18
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 104

```
Ala Arg Arg Gly Leu Glu Arg Gly Leu Asn Ala Leu Ala Asp Ala Val
1               5                   10                  15

Lys Val
```

<210> SEQ ID NO 105
<211> LENGTH: 14
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 105

```
Glu Lys Ile Gly Ala Glu Leu Val Lys Glu Val Ala Lys Lys
1               5                   10
```

<210> SEQ ID NO 106
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 106

```
Gly Leu Lys Arg Gly Ile Glu Lys Ala Val Glu Lys Val Glu Thr Leu
1               5                   10                  15
```

<210> SEQ ID NO 107
<211> LENGTH: 15
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 107

```
Ile Glu Asp Ala Val Arg Asn Ala Lys Ala Ala Val Glu Glu Gly
1               5                   10                  15
```

<210> SEQ ID NO 108
<211> LENGTH: 1083
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 108

```
atgggtgcta gagcttctat tcttagaggt gaaaagcttg ataagtggga aaagattaga      60
cttagaccag gtggtaagaa gcattatatg cttaagcata ttgtttgggc ttctagagaa     120
cttgaaagat ttgctcttaa tccaggtttg cttgaaactt ctgaaggttg taagcaaatt     180
```

```
atgaagcaac ttcaaccagc tcttcaaact ggtactgaag aacttaagtc tctttataat      240
actgttgcta ctctttattg tgttcatgaa aagattgaag ttagagatac taaggaagct      300
cttgataaga ttgaagaaga acaaaataag tgtcaacaaa agactcaaca agctaaggct      360
gctgatggta aggtttctca aaattatcca attgttcaaa atcttcaagg tcaaatggtt      420
catcaagcta tttctccaag aactcttaat gcttgggtta aggttattga agaaaaggct      480
ttttctccag aagttattcc aatgtttact gctctttctg aaggtgctac tccacaagat      540
cttaatacta tgcttaatac tgttggtggt catcaagctg ctatgcaaat gcttaaggat      600
actattaatg aagaagctgc tgaatgggat agacttcatc cagttcatgc tggtccaatt      660
gctccaggtc aaatgagaga accaagaggt tctgatattg ctggtactac ttctactctt      720
caagaacaaa ttgcttggat gacttctaat ccaccaattc cagttggtga tatttataag      780
agatggatta ttcttggtct taataagatt gttagaatgt attctccagt ttctattctt      840
gatattagac aaggtccaaa ggaaccattt agagattatg ttgatagatt ttttaagact      900
cttagagctg aacaagctac tcaagaagtt aagaattgga tgactgatac tcttcttgtt      960
caaaatgcta atccagattg taagactatt cttagggctc ttggtccagg tgctactctt     1020
gaagaaatga tgactgcttg tcaaggtgtt ggtggtccag gtcataaggc tagagttctt     1080
taa                                                                   1083
```

<210> SEQ ID NO 109
<211> LENGTH: 360
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 109

```
Met Gly Ala Arg Ala Ser Ile Leu Arg Gly Glu Lys Leu Asp Lys Trp
1               5                   10                  15

Glu Lys Ile Arg Leu Arg Pro Gly Gly Lys Lys His Tyr Met Leu Lys
            20                  25                  30

His Ile Val Trp Ala Ser Arg Glu Leu Glu Arg Phe Ala Leu Asn Pro
        35                  40                  45

Gly Leu Leu Glu Thr Ser Glu Gly Cys Lys Gln Ile Met Lys Gln Leu
    50                  55                  60

Gln Pro Ala Leu Gln Thr Gly Thr Glu Glu Leu Lys Ser Leu Tyr Asn
65                  70                  75                  80

Thr Val Ala Thr Leu Tyr Cys Val His Glu Lys Ile Glu Val Arg Asp
                85                  90                  95

Thr Lys Glu Ala Leu Asp Lys Ile Glu Glu Glu Gln Asn Lys Cys Gln
            100                 105                 110

Gln Lys Thr Gln Gln Ala Lys Ala Ala Asp Gly Lys Val Ser Gln Asn
        115                 120                 125

Tyr Pro Ile Val Gln Asn Leu Gln Gly Gln Met Val His Gln Ala Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
```

```
              195                 200                 205
Trp Asp Arg Leu His Pro Val His Ala Gly Pro Ile Ala Pro Gly Gln
210                 215                 220

Met Arg Glu Pro Arg Gly Ser Asp Ile Ala Gly Thr Thr Ser Thr Leu
225                 230                 235                 240

Gln Glu Gln Ile Ala Trp Met Thr Ser Asn Pro Ile Pro Val Gly
                    245                 250                 255

Asp Ile Tyr Lys Arg Trp Ile Ile Leu Gly Leu Asn Lys Ile Val Arg
                260                 265                 270

Met Tyr Ser Pro Val Ser Ile Leu Asp Ile Arg Gln Gly Pro Lys Glu
                275                 280                 285

Pro Phe Arg Asp Tyr Val Asp Arg Phe Phe Lys Thr Leu Arg Ala Glu
            290                 295                 300

Gln Ala Thr Gln Glu Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                    325                 330                 335

Gly Ala Thr Leu Glu Glu Met Met Thr Ala Cys Gln Gly Val Gly Gly
                340                 345                 350

Pro Gly His Lys Ala Arg Val Leu
            355                 360

<210> SEQ ID NO 110
<211> LENGTH: 699
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 110

Ala Thr Gly Cys Cys Ala Ala Thr Thr Gly Thr Thr Cys Ala Ala Ala
1               5                   10                  15

Ala Thr Cys Thr Thr Cys Ala Ala Gly Gly Thr Cys Ala Ala Ala Thr
                20                  25                  30

Gly Gly Thr Thr Thr Cys Ala Thr Cys Ala Ala Gly Cys Thr Ala Thr Thr
                35                  40                  45

Thr Cys Thr Cys Cys Ala Ala Gly Ala Ala Cys Thr Cys Thr Thr Ala
            50                  55                  60

Ala Thr Gly Cys Thr Thr Gly Gly Gly Thr Thr Ala Ala Gly Gly Thr
65                  70                  75                  80

Thr Ala Thr Thr Gly Ala Ala Gly Ala Ala Ala Gly Gly Cys Thr
                85                  90                  95

Thr Thr Thr Thr Cys Thr Cys Cys Ala Gly Ala Ala Gly Thr Thr Ala
                    100                 105                 110

Thr Thr Cys Cys Ala Ala Thr Gly Thr Thr Thr Ala Cys Thr Gly Cys
            115                 120                 125

Thr Cys Thr Thr Thr Cys Thr Gly Ala Ala Gly Gly Thr Gly Cys Thr
            130                 135                 140

Ala Cys Thr Cys Cys Ala Cys Ala Ala Gly Ala Thr Cys Thr Thr Ala
145                 150                 155                 160

Ala Thr Ala Cys Thr Ala Thr Gly Cys Thr Thr Ala Ala Thr Ala Cys
                    165                 170                 175

Thr Gly Thr Thr Gly Gly Thr Gly Gly Thr Cys Ala Thr Cys Ala Ala
                180                 185                 190

Gly Cys Thr Gly Cys Thr Ala Thr Gly Cys Ala Ala Ala Thr Gly Cys
```

-continued

```
        195                 200                 205

Thr Thr Ala Ala Gly Gly Ala Thr Ala Cys Thr Ala Thr Thr Ala Ala
    210                 215                 220

Thr Gly Ala Ala Gly Ala Ala Gly Cys Thr Gly Cys Thr Gly Ala Ala
225                 230                 235                 240
Thr Gly Gly Gly Ala Thr Ala Gly Ala Cys Thr Thr Cys Ala Thr Cys
                245                 250                 255
Cys Ala Gly Thr Thr Cys Ala Thr Gly Cys Thr Gly Gly Thr Cys Cys
            260                 265                 270

Ala Ala Thr Thr Gly Cys Thr Cys Cys Ala Gly Gly Thr Cys Ala Ala
        275                 280                 285

Ala Thr Gly Ala Gly Ala Gly Ala Ala Cys Cys Ala Ala Gly Ala Gly
    290                 295                 300

Gly Thr Thr Cys Thr Gly Ala Thr Ala Thr Thr Gly Cys Thr Gly Gly
305                 310                 315                 320
Thr Ala Cys Thr Ala Cys Thr Thr Cys Thr Ala Cys Thr Cys Thr Thr
                325                 330                 335

Cys Ala Ala Gly Ala Ala Cys Ala Ala Ala Thr Thr Gly Cys Thr Thr
            340                 345                 350

Gly Gly Ala Thr Gly Ala Cys Thr Thr Cys Thr Ala Ala Thr Cys Cys
        355                 360                 365

Ala Cys Cys Ala Ala Thr Thr Cys Cys Ala Gly Thr Thr Gly Gly Thr
    370                 375                 380

Gly Ala Thr Ala Thr Thr Thr Ala Thr Ala Ala Gly Ala Gly Ala Thr
385                 390                 395                 400

Gly Gly Ala Thr Thr Ala Thr Thr Cys Thr Thr Gly Gly Thr Cys Thr
                405                 410                 415

Thr Ala Ala Thr Ala Ala Gly Ala Thr Thr Gly Thr Thr Ala Gly Ala
            420                 425                 430

Ala Thr Gly Thr Ala Thr Thr Cys Thr Cys Cys Ala Gly Thr Thr Thr
        435                 440                 445

Cys Thr Ala Thr Thr Cys Thr Thr Gly Ala Thr Ala Thr Thr Ala Gly
    450                 455                 460

Ala Cys Ala Ala Gly Gly Thr Cys Cys Ala Ala Ala Gly Gly Ala Ala
465                 470                 475                 480

Cys Cys Ala Thr Thr Thr Ala Gly Ala Gly Ala Thr Thr Ala Thr Gly
                485                 490                 495

Thr Thr Gly Ala Thr Ala Gly Ala Thr Thr Thr Thr Thr Thr Ala Ala
            500                 505                 510

Gly Ala Cys Thr Cys Thr Thr Ala Gly Ala Gly Cys Thr Gly Ala Ala
        515                 520                 525

Cys Ala Ala Gly Cys Thr Ala Cys Thr Cys Ala Ala Gly Ala Ala Gly
    530                 535                 540

Thr Thr Ala Ala Gly Ala Ala Thr Thr Gly Gly Ala Thr Gly Ala Cys
545                 550                 555                 560

Thr Gly Ala Thr Ala Cys Thr Cys Thr Thr Cys Thr Thr Gly Thr Thr
                565                 570                 575

Cys Ala Ala Ala Ala Thr Gly Cys Thr Ala Ala Thr Cys Cys Ala Gly
            580                 585                 590

Ala Thr Thr Gly Thr Ala Ala Gly Ala Cys Thr Ala Thr Thr Cys Thr
        595                 600                 605

Thr Ala Gly Gly Gly Cys Thr Cys Thr Thr Gly Gly Thr Cys Cys Ala
    610                 615                 620
```

Gly Gly Thr Gly Cys Thr Ala Cys Thr Cys Thr Gly Ala Ala Gly
625                 630                 635                 640

Ala Ala Ala Thr Gly Ala Thr Gly Ala Cys Thr Gly Cys Thr Thr Gly
                645                 650                 655

Thr Cys Ala Ala Gly Gly Thr Gly Thr Thr Gly Gly Thr Gly Gly Thr
            660                 665                 670

Cys Cys Ala Gly Gly Thr Cys Ala Thr Ala Ala Gly Gly Cys Thr Ala
            675                 680                 685

Gly Ala Gly Thr Thr Cys Thr Thr Ala Ala
            690                 695

<210> SEQ ID NO 111
<211> LENGTH: 232
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 111

Met Pro Ile Val Gln Asn Leu Gln Gly Gln Met Val His Gln Ala Ile
1               5                   10                  15

Ser Pro Arg Thr Leu Asn Ala Trp Val Lys Val Ile Glu Glu Lys Ala
            20                  25                  30

Phe Ser Pro Glu Val Ile Pro Met Phe Thr Ala Leu Ser Glu Gly Ala
        35                  40                  45

Thr Pro Gln Asp Leu Asn Thr Met Leu Asn Thr Val Gly Gly His Gln
    50                  55                  60

Ala Ala Met Gln Met Leu Lys Asp Thr Ile Asn Glu Glu Ala Ala Glu
65                  70                  75                  80

Trp Asp Arg Leu His Pro Val His Ala Gly Pro Ile Ala Pro Gly Gln
                85                  90                  95

Met Arg Glu Pro Arg Gly Ser Asp Ile Ala Gly Thr Thr Ser Thr Leu
            100                 105                 110

Gln Glu Gln Ile Ala Trp Met Thr Ser Asn Pro Pro Ile Pro Val Gly
        115                 120                 125

Asp Ile Tyr Lys Arg Trp Ile Ile Leu Gly Leu Asn Lys Ile Val Arg
    130                 135                 140

Met Tyr Ser Pro Val Ser Ile Leu Asp Ile Arg Gln Gly Pro Lys Glu
145                 150                 155                 160

Pro Phe Arg Asp Tyr Val Asp Arg Phe Phe Lys Thr Leu Arg Ala Glu
                165                 170                 175

Gln Ala Thr Gln Glu Val Lys Asn Trp Met Thr Asp Thr Leu Leu Val
            180                 185                 190

Gln Asn Ala Asn Pro Asp Cys Lys Thr Ile Leu Arg Ala Leu Gly Pro
        195                 200                 205

Gly Ala Thr Leu Glu Glu Met Met Thr Ala Cys Gln Gly Val Gly Gly
    210                 215                 220

Pro Gly His Lys Ala Arg Val Leu
225                 230

<210> SEQ ID NO 112
<211> LENGTH: 1731
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 112

```
atgagggtgt tgctcgttgc cctcgctctc ctggctctcg ctgcgagcgc cacctccacg      60
catacaagcg gcggctgcgg ctgccagcca ccgccgccgg ttcatctacc gccgccggtg     120
catctgccac ctccggttca cctgccacct ccggtgcatc tcccaccgcc ggtccacctg     180
ccgccgccgg tccacctgcc accgccggtc catgtgccgc cgccggttca tctgccgccg     240
ccaccatgcc actaccctac tcaaccgccc ggcctcagcc ctcatcccca gccacaccca     300
tgcccgtgcc aacagccgca tccaagcccg tgccagacca tggacgacga tgataagtgc     360
ggcaagaagg ccatcggcac cgtgctggtg gcccccaccc ccgtgaacat catcggccgg     420
aacatgctga cccagctggg ctgcaccctg aacttcccca tcagcccat cgagaccgtg      480
cccgtgaagc tgaagcccgg catggacggc cccaaggtga agcagtggcc cctgaccgag     540
gtgaagatca aggccctgac cgccatctgc gaggagatgg agaaggaggg caagatcacc     600
aagatcggcc ccgagaaccc ctacaacacc cccatcttcg ccatcaagaa ggaggacagc     660
accaagtggc ggaagctggt ggacttccgg gagctgaaca gcggaccca ggacttctgg      720
gaggtgcagc tgggcatccc ccaccccgcc ggcctgaaga agaagaagag cgtgaccgtg     780
ctggacgtgg cgacgcctca cttcagcgtg ccctgacg agggcttccg gaagtacacc       840
gccttcacca tccccagcat caacaacgag accccggca tccggtacca gtacaacgtg      900
ctgccccagg gctggaaggg cagccccgcc atcttccagg ccagcatgac caagatcctg     960
gagcccttcc gggccaagaa ccccgagatc gtgatctacc agtacatggc cgccctgtac    1020
gtgggcagcg acctggagat cggccagcac cgggccaaga tcgaggagct gcgggagcac    1080
ctgctgaagt ggggcttcac cacccccgac aagaagcacc agaaggagcc cccccttcctg  1140
tggatgggct acgagctgca ccccgacaag tggaccgtgc agcccatcca gctgcccgag    1200
aaggacagct ggaccgtgaa cgacatccag aagctggtgg gcaagctgaa ctggaccagc    1260
cagatctacc ccggcatcaa ggtgcggcag ctgtgcaagc tgctgcgggg caccaaggcc    1320
ctgaccgaca tcgtgccct gaccgaggag gccgagctgg agctggccga aaccgggag     1380
atcctgaagg agcccgtgca cggcgtgtac tacgacccca gcaaggacct gatcgccgag   1440
atccagaagc agggcgacga ccagtggacc taccagatct accaggagcc cttcaagaac   1500
ctgaaaaccg gcaagtacgc caagcggcgg accacccaca ccaacgacgt gaagcagctg    1560
accgaggccg tgcagaagat cagcctggag agcatcgtga cctggggcaa gacccccaag    1620
ttccggctgc ccatccagaa ggagacctgg gagatctggt ggaccgacta ctggcaggcc    1680
acctggatcc ccgagtggga gttcgtgaac agcggccgct ttcgaatcta g            1731
```

<210> SEQ ID NO 113
<211> LENGTH: 576
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 113

```
Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
                20                  25                  30

Pro Val His Leu Pro Pro Pro Val His Leu Pro Pro Pro Val His Leu
            35                  40                  45
```

-continued

Pro Pro Pro Val His Leu Pro Pro Val His Leu Pro Pro Val
    50                  55                  60

His Leu Pro Pro Val His Val Pro Pro Val His Leu Pro Pro
65                  70                  75                  80

Pro Pro Cys His Tyr Pro Thr Gln Pro Arg Pro Gln Pro His Pro
                85                  90                  95

Gln Pro His Pro Cys Pro Cys Gln Gln Pro His Pro Ser Pro Cys Gln
            100                 105                 110

Thr Met Asp Asp Asp Lys Cys Gly Lys Ala Ile Gly Thr Val
        115                 120                 125

Leu Val Gly Pro Thr Pro Val Asn Ile Ile Gly Arg Asn Met Leu Thr
130                 135                 140

Gln Leu Gly Cys Thr Leu Asn Phe Pro Ile Ser Pro Ile Glu Thr Val
145                 150                 155                 160

Pro Val Lys Leu Lys Pro Gly Met Asp Gly Pro Lys Val Lys Gln Trp
                165                 170                 175

Pro Leu Thr Glu Val Lys Ile Lys Ala Leu Thr Ala Ile Cys Glu Glu
            180                 185                 190

Met Glu Lys Glu Gly Lys Ile Thr Lys Ile Gly Pro Glu Asn Pro Tyr
        195                 200                 205

Asn Thr Pro Ile Phe Ala Ile Lys Lys Glu Asp Ser Thr Lys Trp Arg
210                 215                 220

Lys Leu Val Asp Phe Arg Glu Leu Asn Lys Arg Thr Gln Asp Phe Trp
225                 230                 235                 240

Glu Val Gln Leu Gly Ile Pro His Pro Ala Gly Leu Lys Lys Lys Lys
                245                 250                 255

Ser Val Thr Val Leu Asp Val Gly Asp Ala Tyr Phe Ser Val Pro Leu
            260                 265                 270

Asp Glu Gly Phe Arg Lys Tyr Thr Ala Phe Thr Ile Pro Ser Ile Asn
        275                 280                 285

Asn Glu Thr Pro Gly Ile Arg Tyr Gln Tyr Asn Val Leu Pro Gln Gly
290                 295                 300

Trp Lys Gly Ser Pro Ala Ile Phe Gln Ala Ser Met Thr Lys Ile Leu
305                 310                 315                 320

Glu Pro Phe Arg Ala Lys Asn Pro Glu Ile Val Ile Tyr Gln Tyr Met
                325                 330                 335

Ala Ala Leu Tyr Val Gly Ser Asp Leu Glu Ile Gly Gln His Arg Ala
            340                 345                 350

Lys Ile Glu Glu Leu Arg Glu His Leu Leu Lys Trp Gly Phe Thr Thr
        355                 360                 365

Pro Asp Lys Lys His Gln Lys Glu Pro Pro Phe Leu Trp Met Gly Tyr
370                 375                 380

Glu Leu His Pro Asp Lys Trp Thr Val Gln Pro Ile Gln Leu Pro Glu
385                 390                 395                 400

Lys Asp Ser Trp Thr Val Asn Asp Ile Gln Lys Leu Val Gly Lys Leu
                405                 410                 415

Asn Trp Thr Ser Gln Ile Tyr Pro Gly Ile Lys Val Arg Gln Leu Cys
            420                 425                 430

Lys Leu Leu Arg Gly Thr Lys Ala Leu Thr Asp Ile Val Pro Leu Thr
        435                 440                 445

Glu Glu Ala Glu Leu Glu Leu Ala Glu Asn Arg Glu Ile Leu Lys Glu
450                 455                 460

Pro Val His Gly Val Tyr Tyr Asp Pro Ser Lys Asp Leu Ile Ala Glu 465 470 475 480

Ile Gln Lys Gln Gly Asp Asp Gln Trp Thr Tyr Gln Ile Tyr Gln Glu
485 490 495

Pro Phe Lys Asn Leu Lys Thr Gly Lys Tyr Ala Lys Arg Arg Thr Thr
500 505 510

His Thr Asn Asp Val Lys Gln Leu Thr Glu Ala Val Gln Lys Ile Ser
515 520 525

Leu Glu Ser Ile Val Thr Trp Gly Lys Thr Pro Lys Phe Arg Leu Pro
530 535 540

Ile Gln Lys Glu Thr Trp Glu Ile Trp Trp Thr Asp Tyr Trp Gln Ala
545 550 555 560

Thr Trp Ile Pro Glu Trp Glu Phe Val Asn Ser Gly Arg Phe Arg Ile
565 570 575

<210> SEQ ID NO 114
<211> LENGTH: 1404
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 114

Ala Thr Gly Thr Cys Thr Thr Cys Ala Ala Gly Thr Gly Thr Thr Thr
1 5 10 15

Ala Thr Gly Ala Gly Thr Cys Gly Ala Thr Cys Ala Thr Thr Cys Ala
20 25 30

Gly Ala Cys Ala Ala Ala Ala Gly Cys Thr Thr Cys Ala Gly Thr Cys
35 40 45

Thr Gly Gly Gly Gly Ala Thr Cys Ala Ala Cys Thr Gly Cys Ala Thr
50 55 60

Cys Thr Gly Gly Thr Ala Ala Ala Gly Cys Thr Gly Thr Thr Gly Thr
65 70 75 80

Ala Gly Ala Thr Thr Cys Thr Thr Ala Cys Thr Gly Gly Ala Thr Thr
85 90 95

Cys Ala Thr Gly Ala Ala Cys Thr Thr Gly Gly Thr Ala Cys Thr Gly
100 105 110

Gly Thr Thr Cys Thr Cys Cys Ala Cys Thr Ala Gly Thr Thr Cys Ala
115 120 125

Ala Ala Cys Cys Cys Ala Gly Cys Thr Gly Thr Ala Thr Thr Cys Thr
130 135 140

Gly Ala Thr Thr Cys Ala Ala Gly Ala Ala Gly Cys Ala Ala Ala Ala
145 150 155 160

Gly Thr Ala Gly Cys Thr Thr Thr Gly Gly Cys Thr Ala Thr Ala Cys
165 170 175

Thr Gly Cys Ala Ala Ala Gly Gly Thr Ala Gly Gly Gly Ala Ala Thr
180 185 190

Cys Thr Thr Cys Cys Cys Thr Gly Thr Gly Ala Gly Gly Ala Ala Gly
195 200 205

Ala Ala Gly Ala Ala Ala Thr Thr Cys Thr Thr Thr Cys Thr Cys Ala
210 215 220

Gly Cys Ala Thr Gly Thr Gly Thr Ala Thr Ala Thr Cys Cys Cys Thr
225 230 235 240

Ala Thr Thr Thr Thr Thr Gly Ala Thr Gly Ala Thr Gly Thr Thr Gly
245 250 255

Ala Thr Thr Thr Thr Ala Gly Cys Ala Thr Cys Ala Ala Thr Ala Thr

-continued

```
            260                 265                 270

Thr Gly Ala Thr Gly Ala Cys Thr Cys Thr Gly Thr Thr Cys Thr Gly
        275                 280                 285

Gly Cys Ala Cys Thr Gly Thr Cys Thr Gly Thr Thr Thr Gly Cys Thr
    290                 295                 300

Cys Cys Ala Ala Cys Ala Cys Ala Gly Thr Cys Ala Ala Thr Ala Cys
305                 310                 315                 320

Thr Ala Ala Cys Gly Gly Ala Gly Thr Gly Ala Ala Ala Cys Ala Thr
                325                 330                 335

Cys Ala Ala Gly Gly Thr Cys Ala Thr Thr Thr Gly Ala Ala Ala Gly
            340                 345                 350
Thr Thr Thr Thr Gly Thr Cys Thr Cys Cys Thr Gly Cys Thr Cys Ala
        355                 360                 365

Gly Cys Thr Cys Cys Ala Cys Thr Cys Thr Ala Thr Thr Gly Gly Ala
    370                 375                 380

Thr Cys Thr Ala Cys Cys Ala Thr Gly Ala Ala Cys Gly Gly Ala Thr
385                 390                 395                 400

Cys Thr Gly Ala Thr Ala Thr Thr Ala Cys Ala Gly Ala Cys Cys Gly
                405                 410                 415

Ala Thr Thr Cys Cys Ala Gly Cys Thr Cys Cys Ala Ala Gly Ala Ala
            420                 425                 430

Ala Ala Ala Gly Ala Thr Ala Thr Ala Ala Thr Thr Cys Cys Cys Ala
        435                 440                 445

Ala Thr Gly Ala Cys Ala Gly Gly Thr Ala Cys Ala Thr Thr Gly Ala
    450                 455                 460

Ala Gly Cys Thr Gly Thr Ala Ala Ala Cys Ala Ala Ala Gly Gly Cys
465                 470                 475                 480
Thr Cys Thr Thr Thr Gly Thr Cys Thr Thr Gly Thr Gly Thr Thr Ala
                485                 490                 495

Ala Ala Gly Ala Gly Cys Ala Thr Ala Cys Cys Thr Ala Thr Ala Ala
            500                 505                 510
Gly Gly Thr Cys Gly Ala Gly Ala Thr Gly Thr Gly Cys Thr Ala Cys
        515                 520                 525

Ala Ala Thr Cys Ala Ala Gly Cys Thr Thr Thr Ala Gly Gly Cys Ala
    530                 535                 540

Ala Ala Gly Thr Gly Ala Ala Thr Gly Thr Thr Cys Thr Ala Thr Cys
545                 550                 555                 560

Cys Cys Cys Thr Ala Ala Cys Ala Gly Ala Ala Ala Thr Gly Thr Cys
                565                 570                 575

Cys Ala Thr Gly Ala Ala Thr Gly Gly Cys Thr Gly Thr Ala Cys Ala
            580                 585                 590

Gly Thr Thr Thr Cys Ala Ala Gly Cys Cys Ala Ala Ala Thr Thr Thr
        595                 600                 605

Cys Ala Ala Thr Cys Ala Ala Gly Thr Thr Gly Ala Ala Ala Gly Cys
    610                 615                 620

Ala Ala Cys Ala Ala Cys Ala Gly Ala Ala Cys Thr Gly Thr Ala Ala
625                 630                 635                 640

Ala Thr Thr Cys Thr Cys Thr Thr Gly Cys Ala Gly Thr Gly Ala Ala
                645                 650                 655

Ala Thr Cys Thr Cys Thr Gly Cys Thr Cys Ala Thr Gly Thr Cys Ala
            660                 665                 670

Gly Cys Ala Gly Gly Ala Ala Ala Thr Ala Ala Cys Ala Thr Cys Ala
        675                 680                 685
```

-continued

```
Thr Gly Cys Cys Thr Ala Ala Cys Thr Cys Thr Cys Ala Gly Gly Cys
    690                 695                 700

Thr Thr Thr Thr Gly Thr Cys Ala Ala Ala Gly Cys Thr Thr Cys Cys
705                 710                 715                 720

Ala Cys Thr Gly Ala Thr Thr Cys Thr Cys Ala Thr Thr Thr Cys Ala
                725                 730                 735

Ala Gly Cys Thr Gly Ala Gly Cys Cys Thr Cys Thr Gly Gly Cys Thr
            740                 745                 750

Ala Ala Gly Ala Gly Thr Thr Cys Cys Ala Ala Ala Gly Gly Thr Thr
        755                 760                 765

Thr Thr Gly Ala Ala Gly Cys Ala Gly Ala Thr Thr Thr Cys Cys Ala
    770                 775                 780

Thr Thr Cys Ala Gly Ala Ala Ala Thr Thr Gly Thr Thr Cys Ala Ala
785                 790                 795                 800

Ala Gly Thr Thr Gly Cys Ala Gly Gly Ala Gly Ala Thr Gly Ala Ala
                805                 810                 815

Ala Cys Thr Ala Ala Cys Ala Ala Ala Ala Cys Ala Thr Thr Thr Thr
            820                 825                 830

Ala Thr Thr Thr Ala Thr Cys Thr Ala Thr Thr Gly Cys Thr Thr Gly
        835                 840                 845

Cys Ala Thr Thr Cys Cys Ala Ala Ala Cys Cys Ala Thr Ala Ala Cys
    850                 855                 860

Ala Gly Thr Gly Thr Thr Gly Ala Gly Ala Cys Ala Gly Cys Thr Thr
865                 870                 875                 880

Thr Ala Ala Ala Cys Ala Thr Thr Thr Cys Thr Gly Thr Thr Ala Thr
                885                 890                 895

Thr Thr Gly Cys Ala Ala Gly Cys Ala Thr Cys Ala Gly Cys Thr Cys
            900                 905                 910

Cys Cys Ala Ala Thr Cys Cys Gly Thr Ala Ala Ala Thr Thr Thr Ala
        915                 920                 925

Ala Ala Gly Cys Thr Cys Cys Thr Thr Thr Thr Gly Ala Ala Thr Thr
    930                 935                 940

Ala Thr Cys Ala Ala Thr Gly Ala Thr Gly Thr Thr Thr Thr Cys Thr
945                 950                 955                 960

Gly Ala Thr Thr Thr Ala Ala Ala Gly Gly Ala Gly Cys Cys Thr Thr
                965                 970                 975

Ala Cys Ala Ala Cys Ala Thr Thr Gly Thr Thr Cys Ala Thr Gly Ala
            980                 985                 990

Thr Cys Cys Thr Thr Cys Ala Thr  Ala Thr Cys Cys Thr  Cys Ala Gly
        995                 1000                1005

Ala Gly  Gly Ala Thr Thr Gly  Thr Thr Cys Ala Thr  Gly Cys Thr
    1010                1015                1020

Cys Thr  Gly Cys Thr Thr Gly  Ala Ala Ala Cys Thr  Cys Ala Cys
    1025                1030                1035

Ala Cys  Gly Thr Cys Thr Thr  Thr Thr Gly Cys Ala  Cys Ala Ala
    1040                1045                1050

Gly Thr  Thr Cys Thr Thr Thr  Gly Cys Ala Ala Cys  Ala Ala Cys
    1055                1060                1065

Thr Thr  Gly Cys Ala Ala Gly  Ala Ala Gly Ala Cys  Gly Thr Gly
    1070                1075                1080

Ala Thr  Cys Ala Thr Cys Thr  Ala Cys Ala Cys Thr  Thr Thr Gly
    1085                1090                1095
```

```
Ala Ala Cys Ala Ala Cys Thr Ala Thr Gly Ala Gly Cys Thr Ala
    1100                1105                1110
Ala Cys Thr Cys Cys Thr Gly Gly Ala Ala Gly Thr Thr Ala
    1115                1120                1125
Gly Ala Thr Cys Thr Ala Gly Gly Thr Gly Ala Ala Ala Gly Ala
    1130                1135                1140
Ala Cys Cys Thr Thr Ala Ala Thr Thr Ala Cys Ala Gly Thr
    1145                1150                1155
Gly Ala Ala Gly Ala Thr Gly Thr Cys Thr Gly Cys Ala Ala Ala
    1160                1165                1170
Ala Gly Gly Ala Ala Ala Thr Ala Thr Thr Thr Cys Cys Thr Cys
    1175                1180                1185
Thr Cys Ala Ala Ala Ala Cys Ala Cys Thr Thr Gly Ala Ala
    1190                1195                1200
Thr Gly Thr Cys Thr Thr Cys Cys Ala Thr Cys Thr Ala Ala Cys
    1205                1210                1215
Ala Cys Ala Cys Ala Ala Cys Thr Ala Thr Gly Thr Cys Thr
    1220                1225                1230
Thr Ala Cys Thr Thr Ala Gly Ala Cys Ala Gly Cys Ala Thr Cys
    1235                1240                1245
Cys Ala Ala Ala Thr Cys Cys Cys Thr Thr Cys Cys Thr Gly Gly
    1250                1255                1260
Ala Ala Gly Ala Thr Ala Gly Ala Cys Thr Thr Thr Gly Cys Thr
    1265                1270                1275
Ala Gly Gly Gly Gly Ala Gly Ala Ala Ala Thr Thr Ala Ala Ala
    1280                1285                1290
Ala Thr Thr Thr Cys Thr Cys Ala Cys Ala Ala Thr Cys Thr
    1295                1300                1305
Gly Thr Thr Thr Cys Ala Gly Thr Thr Gly Cys Ala Ala Ala Ala
    1310                1315                1320
Thr Cys Thr Thr Thr Gly Thr Thr Ala Ala Ala Gly Cys Thr Thr
    1325                1330                1335
Gly Ala Thr Thr Thr Ala Ala Gly Thr Gly Gly Gly Ala Thr Cys
    1340                1345                1350
Ala Ala Ala Ala Ala Gly Ala Ala Ala Gly Ala Ala Thr Cys Thr
    1355                1360                1365
Ala Ala Gly Ala Thr Thr Thr Cys Gly Gly Ala Ala Gly Cys Ala
    1370                1375                1380
Thr Gly Thr Gly Cys Thr Thr Cys Ala Gly Gly Ala Thr Cys Ala
    1385                1390                1395
Ala Ala Ala Thr Ala Ala
    1400

<210> SEQ ID NO 115
<211> LENGTH: 467
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 115

Met Ser Ser Ser Val Tyr Glu Ser Ile Ile Gln Thr Lys Ala Ser Val
1               5                   10                  15

Trp Gly Ser Thr Ala Ser Gly Lys Ala Val Val Asp Ser Tyr Trp Ile
            20                  25                  30
```

-continued

His Glu Leu Gly Thr Gly Ser Pro Leu Val Gln Thr Gln Leu Tyr Ser
            35                  40                  45

Asp Ser Arg Ser Lys Ser Ser Phe Gly Tyr Thr Ala Lys Val Gly Asn
 50                  55                  60

Leu Pro Cys Glu Glu Glu Ile Leu Ser Gln His Val Tyr Ile Pro
 65                  70                  75                  80

Ile Phe Asp Asp Val Asp Phe Ser Ile Asn Ile Asp Asp Ser Val Leu
                    85                  90                  95

Ala Leu Ser Val Cys Ser Asn Thr Val Asn Thr Asn Gly Val Lys His
                100                 105                 110

Gln Gly His Leu Lys Val Leu Ser Pro Ala Gln Leu His Ser Ile Gly
                115                 120                 125

Ser Thr Met Asn Gly Ser Asp Ile Thr Asp Arg Phe Gln Leu Gln Glu
            130                 135                 140

Lys Asp Ile Ile Pro Asn Asp Arg Tyr Ile Glu Ala Val Asn Lys Gly
145                 150                 155                 160

Ser Leu Ser Cys Val Lys Glu His Thr Tyr Lys Val Glu Met Cys Tyr
                165                 170                 175

Asn Gln Ala Leu Gly Lys Val Asn Val Leu Ser Pro Asn Arg Asn Val
                180                 185                 190

His Glu Trp Leu Tyr Ser Phe Lys Pro Asn Phe Asn Gln Val Glu Ser
            195                 200                 205

Asn Asn Arg Thr Val Asn Ser Leu Ala Val Lys Ser Leu Leu Met Ser
        210                 215                 220

Ala Gly Asn Asn Ile Met Pro Asn Ser Gln Ala Phe Val Lys Ala Ser
225                 230                 235                 240

Thr Asp Ser His Phe Lys Leu Ser Leu Trp Leu Arg Val Pro Lys Val
                245                 250                 255

Leu Lys Gln Ile Ser Ile Gln Lys Leu Phe Lys Val Ala Gly Asp Glu
                260                 265                 270

Thr Asn Lys Thr Phe Tyr Leu Ser Ile Ala Cys Ile Pro Asn His Asn
            275                 280                 285

Ser Val Glu Thr Ala Leu Asn Ile Ser Val Ile Cys Lys His Gln Leu
        290                 295                 300

Pro Ile Arg Lys Phe Lys Ala Pro Phe Glu Leu Ser Met Met Phe Ser
305                 310                 315                 320

Asp Leu Lys Glu Pro Tyr Asn Ile Val His Asp Pro Ser Tyr Pro Gln
                325                 330                 335

Arg Ile Val His Ala Leu Leu Glu Thr His Thr Ser Phe Ala Gln Val
            340                 345                 350

Leu Cys Asn Asn Leu Gln Glu Asp Val Ile Ile Tyr Thr Leu Asn Asn
        355                 360                 365

Tyr Glu Leu Thr Pro Gly Lys Leu Asp Leu Gly Glu Arg Thr Leu Asn
    370                 375                 380

Tyr Ser Glu Asp Val Cys Lys Arg Lys Tyr Phe Leu Ser Lys Thr Leu
385                 390                 395                 400

Glu Cys Leu Pro Ser Asn Thr Gln Thr Met Ser Tyr Leu Asp Ser Ile
                405                 410                 415

Gln Ile Pro Ser Trp Lys Ile Asp Phe Ala Arg Gly Glu Ile Lys Ile
            420                 425                 430

Ser Pro Gln Ser Val Ser Val Ala Lys Ser Leu Leu Lys Leu Asp Leu
        435                 440                 445

Ser Gly Ile Lys Lys Lys Glu Ser Lys Ile Ser Glu Ala Cys Ala Ser

Gly Ser Lys
465

<210> SEQ ID NO 116
<211> LENGTH: 9
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 116

Ala Met Gln Met Leu Lys Asp Thr Ile
1               5

<210> SEQ ID NO 117
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 117

Asn Pro Pro Ile Pro Val Gly Asp Ile Tyr Lys Arg Trp Ile Ile Gly
1               5                   10                  15

Leu Asn Lys

<210> SEQ ID NO 118
<211> LENGTH: 20
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 118

Phe Arg Asp Tyr Val Asp Arg Phe Phe Lys Thr Leu Arg Ala Glu Gln
1               5                   10                  15

Ala Thr Gln Glu
            20

<210> SEQ ID NO 119
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 119

Pro Lys Val Lys Gln Trp Pro Leu Thr Glu Val Lys Ile Lys Ala Leu
1               5                   10                  15

Thr Ala Ile

<210> SEQ ID NO 120
<211> LENGTH: 11
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 120

Val Tyr Tyr Asp Pro Ser Lys Asp Leu Ile Ala
1               5                   10

<210> SEQ ID NO 121

```
<211> LENGTH: 9
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 121

Thr Ile His Asp Ile Ile Leu Glu Cys
1               5

<210> SEQ ID NO 122
<211> LENGTH: 10
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 122

Phe Ala Phe Arg Asp Leu Cys Ile Val Tyr
1               5                   10

<210> SEQ ID NO 123
<211> LENGTH: 10
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 123

Tyr Met Leu Asp Leu Gln Pro Glu Thr Thr
1               5                   10

<210> SEQ ID NO 124
<211> LENGTH: 9
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 124

Leu Glu Asp Leu Leu Met Gly Thr Leu
1               5

<210> SEQ ID NO 125
<211> LENGTH: 9
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 125

Asp Leu Tyr Cys Tyr Glu Gln Leu Asn
1               5

<210> SEQ ID NO 126
<211> LENGTH: 462
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 126
cccgccgcca ccatgcacgg cgacaccccc accctgcacg agtacatgct ggacctgcag    60
cccgagacca ccgacctgta ctgcatctgc agccagaaac ccaagtgcga cagcaccctg   120
cggctgtgcg tgcagagcac ccacgtggac atccggaccc tggaggacct gctgatgggc   180
```

| | |
|---|---:|
| accctgggca tcgtgtgccc ctacgagcag ctgaacgaca gcagcgagga ggaggatgag | 240 |
| atcgacggcc ccgccggcca ggctgagccc gaccgggccc actacaacat cgtgaccttc | 300 |
| tgctgccaac cagagacaac tgatctctac tgttatgagc aattaaatga cagctcagag | 360 |
| cattacaata ttgtaacctt tgttgcaag tgtgactcta cgcttcggtt gtgcatgggc | 420 |
| acactaggaa ttgtgtgccc catctgttct cagaaaccat aa | 462 |

<210> SEQ ID NO 127
<211> LENGTH: 4912
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 127

| | |
|---|---:|
| gacggatcgg gagatctccc gatcccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag cttgaccga caattgcatg aagaatctgc | 180 |
| ttaggggttag gcgttttgcg ctgcttcgcg atgtacgggc cagatatacg cgttttgaga | 240 |
| tttctgtcgc cgactaaatt catgtcgcgc gatagtggtg tttatcgccg atagagatgg | 300 |
| cgatattgga aaaatcgata tttgaaaata tggcatattg aaaatgtcgc cgatgtgagt | 360 |
| ttctgtgtaa ctgatatcgc catttttcca aaagtgattt ttgggcatac gcgatatctg | 420 |
| gcgatagcgc ttatatcgtt tacgggggat ggcgatagac gactttggtg acttgggcga | 480 |
| ttctgtgtgt cgcaaatatc gcagtttcga taggtgac agacgatatg aggctatatc | 540 |
| gccgatagag gcgacatcaa gctggcacat ggccaatgca tatcgatcta tacattgaat | 600 |
| caatattggc cattagccat attattcatt ggttatatag cataaatcaa tattggctat | 660 |
| tggccattgc atacgttgta tccatatcat aatatgtaca tttatattgg ctcatgtcca | 720 |
| acattaccgc catgttgaca ttgattattg actagttatt aatagtaatc aattacgggg | 780 |
| tcattagttc atagcccata tatggagttc cgcgttacat aacttacggt aaatggcccg | 840 |
| cctggctgac cgcccaacga cccccgccca ttgacgtcaa taatgacgta tgttcccata | 900 |
| gtaacgccaa tagggactt ccattgacgt caatgggtgg agtatttacg gtaaactgcc | 960 |
| cacttggcag tacatcaagt gtatcatatg ccaagtacgc ccctattga cgtcaatgac | 1020 |
| ggtaaatggc ccgcctggca ttatgcccag tacatgacct tatgggactt tcctacttgg | 1080 |
| cagtacatct acgtattagt catcgctatt accatggtga tgcggttttg gcagtacatc | 1140 |
| aatgggcgtg gatagcggtt tgactcacgg ggatttccaa gtctccaccc cattgacgtc | 1200 |
| aatgggagtt tgttttggca ccaaaatcaa cgggactttc caaaatgtcg taacaactcc | 1260 |
| gccccattga cgcaaatggg cggtaggcgt gtacggtggg aggtctatat aagcagagct | 1320 |
| cgtttagtga accgtcagat cgcctggaga cgccatccac gctgttttga cctccataga | 1380 |
| agacaccggg accgatccag cctccgcggc cgggaacggt gcattggaac gcggattccc | 1440 |
| cgtgccaaga gtgacgtaag taccgcctat agagtctata ggcccacccc cttggcttct | 1500 |
| tatgcatgct atactgtttt tggcttgggg tctatacacc cccgcttcct catgttatag | 1560 |
| gtgatggtat agcttagcct ataggtgtgg gttattgacc attattgacc actcccctat | 1620 |
| tggtgacgat actttccatt actaatccat aacatggctc tttgccacaa ctctctttat | 1680 |
| tggctatatg ccaatacact gtccttcaga gactgacacg gactctgtat ttttacagga | 1740 |
| tggggtctca tttattattt acaaattcac atatacaaca ccaccgtccc cagtgcccgc | 1800 |

```
agtttttatt aaacataacg tgggatctcc acgcgaatct cgggtacgtg ttccggacat    1860
gggctcttct ccggtagcgg cggagcttct acatccgagc cctgctccca tgcctccagc    1920
gactcatggt cgctcggcag ctccttgctc ctaacagtgg aggccagact taggcacagc    1980
acgatgccca ccaccaccag tgtgccgcac aaggccgtgg cggtagggta tgtgtctgaa    2040
aatgagctcg gggagcgggc ttgcaccgct gacgcatttg aagacttaa ggcagcggca     2100 gaagaagatg caggcagctg agttgttgtg ttctgataag agtcagaggt aactcccgtt    2160
gcggtgctgt taacggtgga gggcagtgta gtctgagcag tactcgttgc tgccgcgcgc    2220
gccaccagac ataatagctg acagactaac agactgttcc tttccatggg tcttttctgc    2280
agtcaccgtc cttgacacga agcttggtac cgagctcgga tccactagta acggccgcca    2340
gtgtgctgga attctgcaga tatccatcac actggcggcc gctcgagcat gcatctagag    2400
ggccctattc tatagtgtca cctaaatgct agagctcgct gatcagcctc gactgtgcct    2460
tctagttgcc agccatctgt tgtttgcccc tcccccgtgc cttccttgac cctggaaggt    2520
gccactccca ctgtcctttc ctaataaaat gaggaaattg catcgcattg tctgagtagg    2580
tgtcattcta ttctgggggg tggggtgggg caggacagca aggggagga ttgggaagac     2640 aatagcaggc atgctgggga tgcggtgggc tctatggctt ctgaggcgga aagaaccagc    2700
tggggctcga gggggatcg atcccgtcga cctcgagagc ttggcgtaat catggtcata    2760
gctgtttcct gtgtgaaatt gttatccgct cacaattcca cacaacatac gagccggaag    2820
cataaagtgt aaagcctggg gtgcctaatg agtgagctaa ctcacattaa ttgcgttgcg    2880
ctcactgccc gctttccagt cgggaaacct gtcgtgccag ctgcattaat gaatcggcca    2940
acgcgcgggg agaggcggtt tgcgtattgg gcgctcttcc gcttcctcgc tcactgactc    3000
gctgcgctcg gtcgttcggc tgcggcgagc ggtatcagct cactcaaagg cggtaatacg    3060
gttatccaca gaatcagggg ataacgcagg aaagaacatg tgagcaaaag gccagcaaaa    3120
ggccaggaac cgtaaaaagg ccgcgttgct ggcgtttttc cataggctcc gcccccctga    3180
cgagcatcac aaaaatcgac gctcaagtca gaggtggcga aacccgacag gactataaag    3240
ataccaggcg tttccccctg gaagctccct cgtgcgctct cctgttccga ccctgccgct    3300
taccggatac ctgtccgcct ttctcccttc gggaagcgtg gcgctttctc aatgctcacg    3360
ctgtaggtat ctcagttcgg tgtaggtcgt tcgctccaag ctgggctgtg tgcacgaacc    3420
ccccgttcag cccgaccgct gcgccttatc cggtaactat cgtcttgagt ccaacccggt    3480
aagacacgac ttatcgccac tggcagcagc cactggtaac aggattagca gagcgaggta    3540
tgtaggcggt gctacagagt tcttgaagtg gtggcctaac tacggctaca ctagaaggac    3600
agtatttggt atctgcgctc tgctgaagcc agttaccttc ggaaaaagag ttggtagctc    3660
ttgatccggc aaacaaacca ccgctggtag cggtggtttt tttgtttgca agcagcagat    3720
tacgcgcaga aaaaaggat ctcaagaaga tcctttgatc ttttctacgg gtctgacgc     3780 tcagtggaac gaaaactcac gttaagggat tttggtcatg agattatcaa aaaggatctt    3840
cacctagatc cttttaaatt aaaaatgaag ttttaaatca atctaaagta tatatgagta    3900
aacttggtct gacagttacc aatgcttaat cagtgaggca cctatctcag cgatctgtct    3960
atttcgttca tccatagttg cctgactccc cgtcgtgtag ataactacga tacgggaggg    4020
cttaccatct ggccccagtg ctgcaatgat accgcgagac ccacgctcac cggctccaga    4080
tttatcagca ataaaccagc cagccggaag ggccgagcgc agaagtggtc ctgcaacttt    4140
```

-continued

```
atccgcctcc atccagtcta ttaattgttg ccgggaagct agagtaagta gttcgccagt    4200
taatagtttg cgcaacgttg ttgccattgc tacaggcatc gtggtgtcac gctcgtcgtt    4260
tggtatggct tcattcagct ccggttccca acgatcaagg cgagttacat gatcccccat    4320
gttgtgcaaa aaagcggtta gctccttcgg tcctccgatc gttgtcagaa gtaagttggc    4380
cgcagtgtta tcactcatgg ttatggcagc actgcataat tctcttactg tcatgccatc    4440
cgtaagatgc ttttctgtga ctggtgagta ctcaaccaag tcattctgag aatagtgtat    4500
gcggcgaccg agttgctctt gcccggcgtc aatacgggat aataccgcgc cacatagcag    4560
aactttaaaa gtgctcatca ttggaaaacg ttcttcgggg cgaaaactct caaggatctt    4620
accgctgttg agatccagtt cgatgtaacc cactcgtgca cccaactgat cttcagcatc    4680
ttttactttc accagcgttt ctgggtgagc aaaaacagga aggcaaaatg ccgcaaaaaa    4740
gggaataagg gcgacacgga aatgttgaat actcatactc ttcctttttc aatattattg    4800
aagcatttat cagggttatt gtctcatgag cggatacata tttgaatgta tttagaaaaa    4860
taaacaaata ggggttccgc gcacatttcc ccgaaaagtg ccacctgacg tc            4912
```

<210> SEQ ID NO 128
<211> LENGTH: 386
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 128

```
Met Gly Ser Ile Gly Ala Ala Ser Met Glu Phe Cys Phe Asp Val Phe
  1               5                  10                  15

Lys Glu Leu Lys Val His His Ala Asn Glu Asn Ile Phe Tyr Cys Pro
             20                  25                  30

Ile Ala Ile Met Ser Ala Leu Ala Met Val Tyr Leu Gly Ala Lys Asp
         35                  40                  45

Ser Thr Arg Thr Gln Ile Asn Lys Val Val Arg Phe Asp Lys Leu Pro
     50                  55                  60

Gly Phe Gly Asp Ser Ile Glu Ala Gln Cys Gly Thr Ser Val Asn Val
 65                  70                  75                  80

His Ser Ser Leu Arg Asp Ile Leu Asn Gln Ile Thr Lys Pro Asn Asp
                 85                  90                  95

Val Tyr Ser Phe Ser Leu Ala Ser Arg Leu Tyr Ala Glu Glu Arg Tyr
            100                 105                 110

Pro Ile Leu Pro Glu Tyr Leu Gln Cys Val Lys Glu Leu Tyr Arg Gly
        115                 120                 125

Gly Leu Glu Pro Ile Asn Phe Gln Thr Ala Ala Asp Gln Ala Arg Glu
    130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Thr Phe Lys Asp Glu
            180                 185                 190

Asp Thr Gln Ala Met Pro Phe Arg Val Thr Glu Gln Glu Ser Lys Pro
        195                 200                 205

Val Gln Met Met Tyr Gln Ile Gly Leu Phe Arg Val Ala Ser Met Ala
    210                 215                 220

Ser Glu Lys Met Lys Ile Leu Glu Leu Pro Phe Ala Ser Gly Thr Met
```

```
                225                 230                 235                 240
Ser Met Leu Val Leu Leu Pro Asp Glu Val Ser Gly Leu Glu Gln Leu
                    245                 250                 255

Glu Ser Ile Ile Asn Phe Glu Lys Leu Thr Glu Trp Thr Ser Ser Asn
                260                 265                 270

Val Met Glu Glu Arg Lys Ile Lys Val Tyr Leu Pro Arg Met Lys Met
                275                 280                 285

Glu Glu Lys Tyr Asn Leu Thr Ser Val Leu Met Ala Met Gly Ile Thr
            290                 295                 300

Asp Val Phe Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
                325                 330                 335

Glu Ala Gly Arg Glu Val Val Gly Ser Ala Glu Ala Gly Val Asp Ala
                340                 345                 350

Ala Ser Val Ser Glu Glu Phe Arg Ala Asp His Pro Phe Leu Phe Cys
            355                 360                 365

Ile Lys His Ile Ala Thr Asn Ala Val Leu Phe Phe Gly Arg Cys Val
            370                 375                 380

Ser Pro
385

<210> SEQ ID NO 129
<211> LENGTH: 807
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 129

Ala Thr Gly Ala Gly Gly Gly Thr Gly Thr Thr Gly Cys Thr Cys Gly
1               5                   10                  15

Thr Thr Gly Cys Cys Cys Thr Cys Gly Cys Thr Cys Thr Cys Cys Thr
                20                  25                  30

Gly Gly Cys Thr Cys Thr Cys Gly Cys Thr Gly Cys Gly Ala Gly Cys
            35                  40                  45

Gly Cys Cys Ala Cys Cys Thr Cys Cys Ala Cys Gly Cys Ala Thr Ala
    50                  55                  60

Cys Ala Ala Gly Cys Gly Gly Cys Gly Gly Cys Thr Gly Cys Gly Gly
65                  70                  75                  80

Cys Thr Gly Cys Cys Ala Gly Cys Cys Ala Cys Cys Gly Cys Cys Gly
                85                  90                  95

Cys Cys Gly Gly Thr Thr Cys Ala Thr Cys Thr Ala Cys Cys Gly Cys
                100                 105                 110

Cys Gly Cys Cys Gly Gly Thr Gly Cys Ala Thr Cys Thr Gly Cys Cys
            115                 120                 125

Ala Cys Cys Thr Cys Cys Gly Thr Thr Cys Ala Cys Cys Thr Gly Gly
                130                 135                 140

Cys Cys Ala Cys Cys Thr Cys Cys Gly Gly Thr Gly Cys Ala Thr Cys
145                 150                 155                 160

Thr Cys Cys Cys Ala Cys Cys Gly Cys Cys Gly Gly Thr Cys Cys Ala
                    165                 170                 175

Cys Cys Thr Gly Cys Cys Gly Cys Cys Gly Cys Cys Gly Gly Thr Cys
                180                 185                 190

Cys Ala Cys Cys Thr Gly Cys Cys Ala Cys Cys Gly Cys Cys Gly Gly
```

-continued

```
        195                 200                 205

Thr Cys Cys Ala Thr Gly Thr Gly Cys Cys Gly Cys Cys Gly Cys Cys
    210                 215                 220
Gly Gly Thr Thr Cys Ala Thr Cys Thr Gly Cys Cys Gly Cys Cys Gly
225                 230                 235                 240
Cys Cys Ala Cys Cys Ala Thr Gly Cys Cys Ala Cys Thr Ala Cys Cys
                245                 250                 255
Cys Thr Ala Cys Thr Cys Ala Ala Cys Cys Gly Cys Cys Cys Cys Gly
            260                 265                 270
Gly Cys Cys Thr Cys Ala Gly Cys Cys Thr Cys Ala Thr Cys Cys Cys
        275                 280                 285

Cys Ala Gly Cys Cys Ala Cys Ala Cys Cys Cys Ala Thr Gly Cys Cys
    290                 295                 300

Cys Gly Thr Gly Cys Cys Ala Ala Cys Ala Gly Cys Cys Gly Cys Ala
305                 310                 315                 320

Thr Cys Cys Ala Ala Gly Cys Cys Cys Gly Thr Gly Cys Cys Ala Gly
                325                 330                 335

Ala Cys Cys Ala Thr Gly Gly Ala Cys Gly Ala Cys Gly Ala Thr Gly
            340                 345                 350

Ala Thr Ala Ala Gly Ala Thr Gly Cys Ala Cys Gly Gly Cys Gly Ala
        355                 360                 365

Cys Ala Cys Cys Cys Cys Cys Ala Cys Cys Cys Thr Gly Cys Ala Cys
    370                 375                 380

Gly Ala Gly Thr Ala Cys Ala Thr Gly Cys Thr Gly Gly Ala Cys Cys
385                 390                 395                 400

Thr Gly Cys Ala Gly Cys Cys Cys Gly Ala Gly Ala Cys Cys Ala Cys
                405                 410                 415

Cys Gly Ala Cys Cys Thr Gly Thr Ala Cys Thr Gly Cys Ala Thr Cys
            420                 425                 430

Thr Gly Cys Ala Gly Cys Cys Ala Gly Ala Ala Ala Cys Cys Cys Ala
        435                 440                 445

Ala Gly Thr Gly Cys Gly Ala Cys Ala Gly Cys Ala Cys Cys Cys Thr
    450                 455                 460

Gly Cys Gly Gly Cys Thr Gly Thr Gly Cys Gly Thr Gly Cys Ala Gly
465                 470                 475                 480

Ala Gly Cys Ala Cys Cys Cys Ala Cys Gly Thr Gly Gly Ala Cys Ala
                485                 490                 495

Thr Cys Cys Gly Gly Ala Cys Cys Cys Thr Gly Gly Ala Gly Gly Ala
            500                 505                 510

Cys Cys Thr Gly Cys Thr Gly Ala Thr Gly Gly Gly Cys Ala Cys Cys
        515                 520                 525

Cys Thr Gly Gly Gly Cys Ala Thr Cys Gly Thr Gly Thr Gly Cys Cys
    530                 535                 540

Cys Cys Thr Ala Cys Gly Ala Gly Cys Ala Gly Cys Thr Gly Ala Ala
545                 550                 555                 560

Cys Gly Ala Cys Ala Gly Cys Ala Gly Cys Gly Ala Gly Gly Ala Gly
                565                 570                 575

Gly Ala Gly Gly Ala Thr Gly Ala Gly Ala Thr Cys Gly Ala Cys Gly
            580                 585                 590

Gly Cys Cys Cys Cys Gly Cys Cys Gly Gly Cys Cys Ala Gly Gly Cys
        595                 600                 605

Thr Gly Ala Gly Cys Cys Cys Gly Ala Cys Cys Gly Gly Gly Cys Cys
    610                 615                 620
```

-continued

```
Cys Ala Cys Thr Ala Cys Ala Ala Cys Ala Thr Cys Gly Thr Gly Ala
625                 630                 635                 640

Cys Cys Thr Thr Cys Thr Gly Cys Thr Gly Cys Cys Ala Ala Cys Cys
                645                 650                 655

Ala Gly Ala Gly Ala Cys Ala Ala Cys Thr Gly Ala Thr Cys Thr Cys
            660                 665                 670

Thr Ala Cys Thr Gly Thr Thr Ala Thr Gly Ala Gly Cys Ala Ala Thr
        675                 680                 685

Thr Ala Ala Ala Thr Gly Ala Cys Ala Gly Cys Thr Cys Ala Gly Ala
    690                 695                 700

Gly Cys Ala Thr Thr Ala Cys Ala Ala Thr Ala Thr Thr Gly Thr Ala
705                 710                 715                 720

Ala Cys Cys Thr Thr Thr Thr Gly Thr Thr Gly Cys Ala Ala Gly Thr
                725                 730                 735

Gly Thr Gly Ala Cys Thr Cys Thr Ala Cys Gly Cys Thr Thr Cys Gly
            740                 745                 750

Gly Thr Thr Gly Thr Gly Cys Ala Thr Gly Gly Gly Cys Ala Cys Ala
        755                 760                 765

Cys Thr Ala Gly Gly Ala Ala Thr Thr Gly Thr Gly Thr Gly Cys Cys
    770                 775                 780

Cys Cys Ala Thr Cys Thr Gly Thr Thr Cys Thr Cys Ala Gly Ala Ala
785                 790                 795                 800

Ala Cys Cys Ala Thr Ala Ala
                805
```